(12) United States Patent
Gorman et al.

(10) Patent No.: US 6,348,327 B1
(45) Date of Patent: Feb. 19, 2002

(54) NON-ENDOCRINE ANIMAL HOST CELLS CAPABLE OF EXPRESSING VARIANT PROINSULIN AND PROCESSING THE SAME TO FORM ACTIVE, MATURE INSULIN AND METHODS OF CULTURING SUCH CELLS

(75) Inventors: Cornelia M. Gorman; Debyra J. Groskreutz, both of San Francisco, CA (US)

(73) Assignee: Genentech, Inc., S. San Francisco, CA (US)

( * ) Notice: Subject to any disclaimer, the term of this patent is extended or adjusted under 35 U.S.C. 154(b) by 0 days.

(21) Appl. No.: 08/026,143

(22) Filed: Mar. 1, 1993

Related U.S. Application Data

(63) Continuation-in-part of application No. PCT/US92/10621, filed on Dec. 4, 1992, which is a continuation-in-part of application No. 07/887,265, filed on May 22, 1992, now abandoned, which is a continuation-in-part of application No. 07/803,631, filed on Dec. 6, 1991, now abandoned.

(51) Int. Cl.$^7$ .......................... C12P 21/02; C12N 15/63; C12N 5/10

(52) U.S. Cl. .................. 435/69.1; 435/320.1; 435/325

(58) Field of Search .................. 435/6, 69.1, 69.4, 435/240.2, 320.1, 325; 536/23.1, 23.2, 23.4, 23.5, 23.51, 23.52, 23.53, 23.7; 530/397, 399

(56) References Cited

U.S. PATENT DOCUMENTS

| | | | |
|---|---|---|---|
| 4,267,101 A | | 5/1981 | Bigazzi |
| 4,396,601 A | | 8/1983 | Salser et al. |
| 4,399,216 A | * | 8/1983 | Axel et al. |
| 4,431,740 A | * | 2/1984 | Bell et al. |
| H245 H | * | 4/1987 | Bahl |
| 4,792,602 A | * | 12/1988 | Narang et al. |
| 4,914,026 A | * | 4/1990 | Brake et al. |
| 4,970,154 A | | 11/1990 | Chang |
| 5,077,204 A | | 12/1991 | Brake et al. |
| 5,104,652 A | | 4/1992 | Moughton et al. |
| 5,298,422 A | * | 3/1994 | Schwartz et al. |
| 5,304,473 A | * | 4/1994 | Belagaje et al. |
| 5,427,940 A | | 6/1995 | Newgard |
| 5,460,950 A | * | 10/1995 | Barr et al. |

FOREIGN PATENT DOCUMENTS

| | | |
|---|---|---|
| AU | 616201 | 5/1989 |
| EP | 068375 | 1/1983 |
| EP | 101309 | 2/1984 |
| EP | 112149 | 6/1984 |
| EP | 220689 | 5/1987 |
| EP | 253314 | 1/1988 |
| EP | 307247 A2 | 3/1989 |
| EP | 0 307 247 * | 3/1989 |
| EP | 319944 | 6/1989 |
| EP | 324274 | 7/1989 |
| EP | 327377 | 8/1989 |
| WO | WO 90/06997 | 6/1990 |
| WO | WO 90/15863 | 12/1990 |
| WO | WO 91/02540 | 3/1991 |
| WO | WO 91/06314 | 5/1991 |
| WO | WO 91/12329 | 8/1991 |
| WO | WO 91/15580 | 10/1991 |
| WO | WO 91/18988 | 12/1991 |
| WO | 9221756 * | 12/1992 |
| WO | WO 92/21756 | 12/1992 |
| WO | WO 92/21979 | 12/1992 |
| WO | WO 93/11247 | 6/1993 |

OTHER PUBLICATIONS

Schwartz et al., *PNAS*, vol. 84, pp. 6408–6411, 1987.*
Davidson et al, "Intraorganellar calcium and pH control proinsulin clearage . . . ", *Nature* 333:93–96 (May 1988).*
Thorens et al, "Cloning and Functional Expression in Bacteria of a Novel Glucose Transporter . . . ", *Cell* 55: 281–290 (Oct. 1988).*
Permutt et al, "Cloning and Functional Expression of a human pancreatic islet glucose–transporter cDNA", *PNAS* 86: 8688–8692 (Nov. 1989).*
Thomas et al, "KexZ–like endoproteases PC2 and PC3 . . . " *PNAS* 88: 5297–5301 (Jun. 1991).*
Barr, "Mammalian Subtilisins:The Long–Sought Dibasic Processing Endoproteases", *Cell* 66: 1–3 (Jul. 1991).*
Hatsuzawa et al, "Structure and Expression of Mouse Furin . . . " *J. Biol. Chem.* 265(36):22075–22078 (Dec. 1990).*
Thomas et al, "Yeast KEXZ Endopeptidase Correctly Cleaves a Neuroendocrine Prohormone . . . ", *Science* 241:226–230 (Jul. 1988).*
Wim J.M. van de Ven (1990) Molecular Biology Reports 14:265–275.*
Newgard et al. (1990) Biochem. Soc. Trans 18(5) : pp 851–853.*
Hsiao–Ping et al. (1983) Cell : vol. 35, pp 531–538.*
Hughes et al. (Jan., 1992) PNAS vol. 89. pp 688–692.*
Hughes et al., "Engineering of glucose–stimulated insulin secretion and biosynthesis in non–islet cells", *Proc. Natl. Acad Sci.*, 89(2): 688–692 (1992).
Marriot et al., "Prohormone convertase–1 will process pro-relaxin, a member of the insulin family of hormones", *Molecular Endocrinology*, 6(9): 1441–1449 (1992).
Thorne et al., "Expression and Processing of Mouse Proopiomelanocortin in Bovine Adrenal Chromaffin Cells" *Journal of Biological Chemistry* 266(21):13607–13615 (1991).
Chance *Diabetes* 21 (Suppl. 2):461–467 (1972).

(List continued on next page.)

*Primary Examiner*—Gary L. Kunz
*Assistant Examiner*—Stephen Gucker
(74) *Attorney, Agent, or Firm*—Merchant & Gould P.C.

(57) ABSTRACT

Provided are animal host cells not naturally capable of forming secretory granules and that produce active, mature insulin by expression of a variant proinsulin containing a non-naturally occurring cleavage site and enzymatic cleavage of the non-naturally occurring cleavage site in the host cells. Further provided are methods of culturing such cells.

24 Claims, 15 Drawing Sheets

OTHER PUBLICATIONS

Groskreutz et al., *Journal of Biological Chemistry* 269:6241–6245 (1994).

Katsoyannis et al., *Biochemistry* 6:2635–2642 (1967).

Seidah et al., "cDNA sequence of two distinct pituitary proteins homologous to kex2 and furin gene products: tissue–specific mRNAs encoding candidates for pro–hormone processing proteinases", *DNA and Cell Biology*, 9(6):415–424 (1990).

Davidson et al., "Intraorganellar calcium and pH control proinsulin cleavage in the pancreatic B cell via two distinct site–specific endopeptidases", *Nature*, 533: 93–96 (1988).

Loh et al., "Purification and characterization of a Paired Basic Residue–specific Pro–opiomelanocortin Converting Enzyme from Bovine Pituitary Intermediate Lobe Secretory Vesicles", *J. Biol Chem.*, 280(12): 7194–7205 (1985).

Thorne et al., "Expression and Processing of Mouse Pro–opiomelanocortin in Bovine Adrenal Chromaffin Cells". *J. Biol Chem.*, 266(21): 13607–13615 (1991).

Thorne et al., "An in vivo characterization of the cleavage site specificity of the insulin cell prohormone processing enzymes", *J. Biol Chem.*, 265(15): 8436–8443 (1990).

Brennan et al., "The Processing of Human Proinsulin and Chicken Proalbumin by Rat Hepatic Vesicles Suggests a Convertase Specific for X–Y–Arg–Arg or Arg–X–Y–Arg Sequences", *J. Biol Chem.*, 266(32): 21504–21508 (1991).

Docherty et al., "Proinsulin Endopeptidase Substrate Specificities Defined by Site–directed Mutagenesis of Proinsulin", *J. Biol Chem.*, 264(31): 18335–18339 (1989).

watanabe et al., "Sequence Requirements for Precursor Cleavage within the Constitutive Secretory Pathway", *J. Biol Chem.*, 267(12): 8270–8274 (1992).

Noel et al., "Investigation of the Structural Requirements for Peptide Precursor Processing in AtT–20 Cells Using Site–Directed Mutagenesis of Proadrenocorticotropin/Endorphin", *Molecular Endocrinology*, 6(3): 404–413 (1991).

Gross et al., "Deletion of a highly conserved tetrapeptide sequence of the proinsulin connecting peptide (C–peptide) inhibits proinsulin to insulin conversion by transfected pituitary corticotroph (AtT20) cells", *J. Biol Chem.*, 264(36): 21486–21490 (1989).

Bloomquist et al., "Prohormone–converting enzymes: Regulation and evaluation of function using antisense RNA", *Molecular Endocrinology*, 5(12): 2014–2024 (1991).

Dickerson et al., "Cell–type specific post–translational processing of peptides by different pituitary cell lines", *Endocrinology* 127(1): 133–140 (1990).

Benjannet et al., "PC1 and PC2 are proprotein converlases capable of cleaving proopiomelanocortin at dinstinct pairs of basic residues", *Proc. Natl. Acad. Sci USA*, 88: 3564–3568 (1991).

Korner et al., "Prohormone processing in *Xenopus oocytes*: Characterization of cleavage signals and cleavage enzymes", *Proc. Natl. Acad. Sci USA*, 88: 11393–11397 (1991).

Steiner, Donald F., "Prohormone convertases revealed at last", *Current Biology*, 1(6): 375–377 (1991).

Keifer et al., "Identification of a Second Human Subtilisin–Like Protease Gene in the fes/fps Region of Chromosome 15", *DNA and Cell Bioloby*, 10(10): 757–769 (1991).

Brennan et al. "Specificity of yeast kex2 protease for variant human proalbumins is identical to the in vivo specificity of the hepatic proalbumin convertase", *J Biol Chem.*, 265(35): 21494–21497 (1990).

Christie et al., "Identification of kex2–related Proteases in Chromaffin Granules by Partial Amino Acid Sequence Analysis", *J. Biol Chem.*, 266(24): 15679–15683 (1991).

Lindberg and Thomas, "Cleavage of Proenkephalin by a Chromaffin Granule Processing Enzyme", *Endocrinology*, 126(1): 480–487 (1990).

Fuller, Robret et al., "Intracellular targeting and structural conservation of a prohormone–processing endoprotease", *Science*, 246: 482–486 (1989).

Paul et al., "Cell–dependent posttranslational processing and secretion of recombinant mouse renin–2", *American Physiological Society*, E224–E229 (1992).

Rouille et al., "Evidence for distinct dibasic processing endopeptidases with Lys–Arg and Arg–Arg specificities in neurohypophysial secretory granules", *Biochem. Biophys. Res. Comm.*, 183(1): 128–137 (1992).

Naganama et al., "Sequence requirements for prohormone processing in mouse pituitary AtT–20 cells. Analysis using proteins as model substrates", *Eur. J. Biochem.* 187: 135–140 (1991).

Noel et al., "Expression of porcine pro–opiomelanocortin cDNA in heterologous monkey kidney cells", *J. Bio Chem.*, 282(4): 1876–1881 (1987).

Barr, Philip J., "Mammalian subtilisins: the long–sought dibasic processing endoproteases", *Cell*, 88: 1–3 (1991).

Moore et al., "Expressing a human Proinsulin cDNA in a Mouse ACTH–Secreting Cell. Intracellular Storage, Proteolytic Processing, and Secretion on Stimulation", *Cell*, 35(Part 1): 531–538 (1983).

Yoshimasa et al., "Effects of amino acid replacements within the tetrabasic cleavage site on the processing of the human insulin receptor precursor expressed in Chinese hamster ovary cells", *J. Biol. Chem.*, 286(28): 17230–17237 (1990).

Wise et al., "Expression of a human proprotein processing enzyme: correct cleavage of the von willebrand factor precursor at a paired basic amino acid site", *Proc. Natl. Acad. Sci. USA*, 87: 9378–9382 (1990).

Nakayama et al., "Identification of the Fourth Member of the Mammalian Endoprotease Family Homologoous to the Yeast Kex2 Protease", *J. Biol Chem.*, 267(8): 5897–5900 (1992).

Shennan et al., "Site–directed Mutagenesis and Expression of PC2 in Microinjected *Xenopus oocytes*", *J. Bio Chem.*, 266(35): 24011–24017 (1991).

Shennan et al., "Characterization of PC2, a mammalian Kex2 homologue, following expression of the cDNA in microinjected *Xenopus oocytes*", *FEBS* 284(2): 277–280 (1991).

Thomas, L. et al., "Kex2–like endoproteases PC2 and PC3 accurately cleave a model prohormone in mammalian cells: evidence for a common core of neuroendocrine processing enzymes", *Proc. Natl. Acad. Sci. USA*, 88: 5297–5301 (1991).

Smeekens, S, and Steiner, D., et al., "Identification of a human insulinoma cDNA enccoding a novel mammalian protein structurally related to the yeast dibasic processing protease kex2", *J. Biol Chem.*, 265(8): 2997–3000 (1990).

Seidah et al., "Cloning and primary sequence of a mouse candidate prohormone convertase PC1 homologous to PC2, furin, and kex2: distinct chromosomal localization and messenger RNA distribution in brain and pituitary compared to PC2", *Molecular Endocrinology*, 5(1): 111–122 (1991).

Nakayama et al., "Cloning and Functional Expression of a Novel Endoprotease Involved in Prohormone Processing at Dibasic Sites", *J. Biochem.*, 109(6): 803–806 (1991).

Zhu et al., "Kex2–dependent processing of yeast $K_1$ killer preprotoxin includes cleavage at ProArg–44", *Molecular Microbiol.*, 8(4): 511–520 (1992).

Brenner et al., "Structural and enzymatic characterization of a purified prohormone–processing enzyme: Secreted, soluble Kex2 protease", *Proc. Natl. Acad. Sci. USA* 86: 922–926 (1992).

Germain et al., "The yeast kex2–processing endoprotease is active in the Golgi apparatus of transfected NIH 3T3 fibroblasts", *Molecular Endocrinology*, 4(10): 1572–1579 (1990).

Thomas et al., "Yeast kEx2 endopeptidase correctly cleaves a neuroendocrine prohormone in mammalian cells", *Science* 241: 226–230 (1988).

Hosaka et al., "Arg–X–Lys/Arg–Arg Motif as a Signal for Precursor Cleavage Catalyzed by Furin within the Constitutive Secretory Pathway", *J. Biol. Chem.*, 265(19): 12127–12130 (1991).

Mains, R. E. et al., "Cellular and molecular aspects of peptide hormone biosynthesis", Frontiers in *Neuroendocrinology*, 11(1): 52–89 (1990).

Matsuzawa et al., "Structure and expression of mouse furin, a yeast Kex2–related protease", J. Biol. Chem., 265(36): 22075–22078 (1990).

Misumi et al. "Functional expression of furin demonstrating its intracellular localization and endoprotease activity for processing of proalbumin and complement Pro–C3", *J. Biol. Chem.*, 266(25): 16954–16959 (1991).

van de Ven et al., "Furin is a subtilisin–like proprotein processing enzyme in higher eukaryotes", *Molecular Biol. Reports*, 14: 265–275 (1990).

Barr, P. J. et al., "cDNA and gene structure for a human subtilisin–like protease with cleavage specificity for paired basic amino acid residues", *DNA and Cell Biology*, 10(5): 319–328 (1991).

Bresnahan, P. A. et al., "Human fur gene encodes a yeast kex2–like endoprotease that cleaves pro–β–NGF in vivo", *J. Cell Biology*, 111(6.Pt 2): 2851–2859 (1990).

van den Ouweland et al., "Structural homology between the human fur gene product and the subtilisin–like protease encoded by yeast KEX2", *Nucleic Acids Res.*, 18(3): 664 (1990).

Bathurst IC et al., "Yeast kex2 protease has the properties of a human proalbumin converting enzyme", *Science* 235: 238–250 (1986).

Chung K–N et al., "Molecular sorting in the secretory pathway", *Science* 243: 192–197 (1989).

Docherty K, et al., "Post–translational proteolysis in polypeptide hormone biosynthesis", *Annu Rev Physiol* 44: 625–638 (1982).

Douglass J. et al., "Polyprotein gene expression: Generation of diversity of neuroendocrine peptides", *Annu Rev Biochem*, 53: 665–715 (1984).

Foster DC, et al., "Endoproteolytic processing of the human protein C precursor by the yeast kex2 endopeptidase coexpressed in mammalian cells", *Biochemistry* 30: 367–372 (1991).

Fricker LD, et al., "Identification of the pH–dependent membrane anchor of carboxypeptidase E (E 3.4.17.10)", *J. Biol Chem.* 265(5): 2476–2482 (1990).

Frohman MA, et al., "Rapid production of full–length cDNAs from rare transcripts: amplification using a single gene specific oligonucleotide primer", *Proc. Natl. Acad. Sci. USA* 85:8998–9002 (1998).

Fuller RS et al., "Yeast prohormone processing enzyme (KEx2 gene product) is a $Ca^{2-}$–dependent serine protease", *Proc Natl Acad Sci USA* 86:1434–1438 (1989).

Gorman CM, et al., "Transient production of proteins using an adenovirus transformed cell line", *DNA Prot Eng Tech* 2:3–10 (1990).

Gumbiner B, et at., "Two distinct intracellular pathways transport secretory and membrane glycoproteins to the surface of pituitary tumour cells", *Cell* 28:51–59 (1982).

Mansell DJ, et al., "Expression of the human relaxin h1 gene in the decidua, trophoblast and prostate", *J Clin Endocrinol Metabol* 72:899–904 (1991).

Mudson P, John M. et al., "Relaxin gene expression in human ovaries and the predicted structure of a human preprorelaxin by analysis of cDNA clones", *EMBO J* 3(10)2333–2339 (1984).

Haley et al., "Porcine Relaxin: Molecular Cloning and cDNA Structure", *DNA*, 1(2): 155–162 (1982).

Julius D et al., "Yeast α factor is sprocessed from a larger precursor polypeptide: the essential role of a membrane–bound dipeptidyl aminopeptidase", *Cell* 32:839 852 (1983).

Julius D et al., "Isolation of the putative structural gene for the lysine–arginine–cleaving endopeptidase required for processing of yeast prepro–α–factor", *Cell* 37:1075–1089 (1984).

Kunkel TA et al., Rapid and efficient site–specific mutagenesis without phenotypic selection:, *Methods Enzymol* 154:367–383 (1987).

Lee CC et al.,"Generation of cDNA probes directed by amino acid sequence: cloning of urate oxidase", *Science* 238:1288–1291 (1988).

Loh YP et al., Proteolysis in neuropeptide processing and other neural functions:, *Annu Rev Neurosci* 7:189–222 (1984).

Moore H–P et al., "Chloroquine diverts ACTH from a regulated to a constitutive pathway in AtT–20 cells", *Nature* 302:434–436 (1983).

Nishi M et al., "Conservation of the sequence of islet amyloid polypeptide in five mammals is consistent with its putative role as an islet hormone", *Proc Natl Acad Sci USA* 86:5738–5742 (1989).

Redding K et al., "Immunolocalization of kex2 protease identifies a putative late Golgi compartment in the yeast *Saccharomyces cerevisiae*", *J Cell Biol* 113(3):527–538 (1991).

Sherwood DD, "Relaxin", Knobil E, Neill J (eds) *The Physiology of Reproduction*, Raven Press, New York pp 585 673 (1988).

Smeekens SP et al., "Identification of a cDNA encoding a second putative prohormone coonvertase related to PC2 in AtT–20 cells and islets of Langerhans", *Proc Natl Acad Sci USA* 88:340–344 (1991).

Stults JT et al. "Structural Characterization by mass spectrometry of native and recombinant human relaxin", *Biomed Environ Mass Spectrom* 18:655–664 (1991).

Zollinger L et al., "Intracellular proteolytic processing of proopiomelanocortin in heterologous COS–1 cells by the yeast KEX2 endoprotease", *Biochem Cell Biol* 88:635–640 (1990).

Angeletti, RH et al., "Amino acid sequences of mouse 5S nerve growth factor. II. Isolation and characterization of the thermolytic and peptic peptides and the complete covalent structure," *Biochemistry* 12(1):100–115 (1973).

Benore–Parsons, M et al., "Substrate phosphorylation an inhibit proteolysis by trypsin–like enzymes", *Arch. Biochem. Biophys.* 272(2):274–280 (1989).

Berger, EA et al., "Evidence for pro–β–nerve growth factor, a biosynthetic precursor to β–nerve growth factor", *Proc Natl Acad Sci USA* 74(9):3647–3651 (1977).

Cohen, S., "Purification of a nerve–growth promoting protein from the mouse salivary gland and its neuro–cytotoxic antiserum", *Proc Natl Acad Sci USA* 46:302–311 (1960).

Ernfors, P et al., "Molecular cloning and neurotrophic activities of a protein with structural similarities to nerve growth factor: developmental and topographical expression in the brain", *Proc Natl Acad Sci USA* 87:5454–5458 (1990).

Gray, AM et al., "Requirement for activin A and transforming growth factor–β1 pro–regions in homodimer assembly", *Science* 247:1328–1330 (1990).

Hohn, A et al., "Identification and characterization of a novel member of the nerve growth factor/brain–derived neurotrophic factor family", *Nature* 344:339–341 (1990).

Jones, KR et al., "Molecular cloning of a human gene that is a member of the nerve growth factor family", *Proc Natl Acad Sci USA* 87:8060–8064 (1990).

Leibrock, J et al., "Molecular cloning and expression of brain–derived neurotrophic factor", *Nature* 341:149–152 (1989).

Levi–Montalcini et al., "Destruction of the sympathetic ganglia in mammals by an antiserum to a nerve–growth protein", *Proc Natl Acad Sci USA* 46:384–391 (1960).

Maisonpierre, PC et al., "Neurotrophin–3: a neurotrophic factor related to NGF and BDNF", *Science* 247:1446–1451 (1990).

Pan, LC et al., "The propeptide of rat bone γ carboxyglutamic acid protein shares homology with other vitamin K–dependent protein precursors", *Proc Natl Acad Sci USA* 82:6109–6113 (1985).

Powell, SK, et al., "Efficient targeting to storage granules of human proinsulins with altered propeptide domain", *J. Cell Biol.* 106:1843–1851 (1988).

Rosenthal, A et al., "Primary structure and biological activity of a novel neurotrophic factor", *Neuron* 4:767–773 (1990).

Saiki, RK et al., "Enzymatic amplification of β–globin genomic sequences and restriction site analysis for diagnosis of Sickle Cell Anemia", *Science* 236:1350–135 (1985).

Scott, J et al., "Isolation and nucleotide sequence of a cDNA encoding the precursor of mouse nerve growth factor". *Nature* 302:538–540 (1983).

Selby, MJ et al., "Cobra nerve growth factor: structure and evolutionary comparison", *J. Neurosci. Res.* 18:293–298 (1987).

Sevarino, KA et al., "Amino–terminal sequences of prosomatostatin direct intracellular targeting but not processing specificity", *Cell* 57:11–19 (1989).

Steiner, DF "Proteolytic processing of secretory proteins", Schmitt et al., eds. *Molecular Genetic Neuroscience*, New York: Raven Press: 149–159 (1982).

Wise, RJ et al., "The propeptide of von willebrand factor independently mediates the assembly of von Willebrand multimers", *Cell* 52:229–236 (1988).

Johnson, I. S., "Human insulin from recombinant DNA technology", *Science*, 218:632–637 (1983).

Selden et al., "Regulation of human insulin gene expression in transgenic mice", *Nature* 321:525–528 (1986).

Thorens et al., "Molecular physiology of glucose transporters", *Diabetes Care* 13(3):209–218 (1990).

Bell et al., "Molecular Biology of Mammalian Glucose Transporters", *Diabetes Care*, 13(3):198–208 (1990).

Cuif et al., "Elements Responsible for Hormonal Control and Tissue Specificity of L–Type Pyruvate Kinase Gene Expression in Transgenic Mice", *Mol. and Cell. Biology*, 12(11):4852–61 (1992).

Carroll et al., "A mutant human proinsulin is secreted from islets of Langerhans in increase amounts via an unregulated pathway", *Proc Natl Acad Sci USA* 85:8943–8947 (1988).

Quinn et al., "Intracellular Transport and Sorting of Mutant Human Proinsulins that Fail to Form Hexamers", *Journal of Cell Biology*, 113:987–996 (1991).

Rinderknecht, et al., "The Amino Acid Sequence of Human Insulin–like Growth Factor 1 and Its Structural Homology with Proinsulin", *Journal of Biological Chemistry* 263(8);2769–2776 (1987).

Rinderknecht, et al., "Primary structure of human insulinlike growth factor II", *FEBS Letters* 88(2):283–286 (1978).

Jansen, et al., "Sequence of cDNA encoding human insulin-like growth factor I precursor", *Nature* 308:609–611 (1984).

Bell, et al., "Sequence of a cDNA clone encoding human preproinsulin–like growth factor II", *Nature*, 310:775–777 (1984).

Jansen, et al., "Nucleotide sequences of cDNAs encoding precursors of human insulin–like growth factor II (IGF–II) and an IGF–II variant", *FEBS Letters* 178(2):243–246 (1985).

Felgner et al., "Gene therapeutics", *Nature*, 348:351–352 (1991).

Waldman, "Targeted homologous recombination mammalian cells", *Critical Reviews in Oncology/Hematology* 12:49–64 (1992).

Reid et al., *Guide to Electroporation and Electrofusion*, Chang et al., editor, Academic Press 209–225 (1992).

Chang, et al., "High efficiency gene transfection by electroporation using a radio–frequency electric field", *Biochimica et Biophysica Acta*, 1992(2):153–160 (1991).

Barsoum, "Laboratory Methods Introduction of Stable High–Copy–Number DNA into Chinese Hamster Ovary Cells by Electroporation", *DNA and Cell Biology* 8(4):293–300 (1990).

Wang et al., "pH–sensitive immunoliposomes mediate target–cell–specific delivery and controlled expression of a foreign gene in mouse", *Proc Natl Acad Sci USA* 84:7851–7855 (1987).

Kaneda et al., "Increased Expression of DNA Cointroduced with Nuclear Protein in Adult Rat Liver", *Science*, 243:375–378 (1989).

Ono et al., "Plasmid DNAs directly injected into mouse brain with lipofectin can be incorporated and expressed by brain cells", *Neurosci Lett.*, 117:259–263 (1990).

Erlich et al., "Recent Advances in the Polymerse Chain Reaction", *Science*, 252:1643–1651 (1991).

Sures, et al., "Nucleotide sequence of human preproinsulin complementary DNA", *Science* 208:57–59 1980).

Tani et al., "Human Liver Type Pyruvate Kinase: cDNA Cloning and Chromosomal Assignment", *Biochem. Biophys. Res. Commun.*, 143(2):431–438 (1987).

Miller et al., "Expression of a Retrovirus Encoding Human HPRT in Mice", *Science*, 225:630–632 (1984).

Miller et al., Redesign of Retrovirus Packaging Cell Lines to Avoid Recombination Leading to Helper Virus Production:, *Mol. Cell. Biol.*, 8(8):2895–2902 (1986).

Dhawan et al., "Systemic delivery of human growth hormone by injection of genetically engineered myoblasts", *Science* 264:1509–1512 (1991).

Yaffe et al., "Serial passaging and differentiation of Myogenic cells isolated from dystrophic mouse muscle", *Nature*, 270:725–727 (1977).

Blau et al., "Plasticity of the Differentiated State", *Science*, 230:758–766 (1985).

Stewart et al., "Transgenic Mouse Models for Insulin Dependent Diabetes: Mechanisms of βCell Damage", *Cytokine Interactions and Their Control*, 93–104 (1991).

\* cited by examiner

FIG. 1A

```
TCTAGATCTA GCTGGTGTGT CTCTGATCTT GCTTCTTTTC TCCCAGCCCT  50

TCCTACTTGT GTGAGAACAA GGTTTTGAGC CATGGAGCAA AGAGGTTGGA  100

CTCTGCAGTG TACTGCTTTC GCCTTCTTTT GCGTTTGGTG TGCACTAAGC  150

AGTGTAAAAG CAAAGAGGCA GTTTGTTAAT GAATGGGCGG CGGAGATCCC  200

CGGAGGGCAA GAAGCTGCCT CTGCCATCGC CGAAGAACTG GGTATGACC  250

TTTTGGGTCA GATTGGATCA CTTGAAAATC ACTATTTATT CAAACACAAA  300

AGCCATCCTC GGAGGTCCCG AAGAAGCGCT CTTCATATCA CTAAGAGGTT  350

ATCTGATGAT GATCGTGTGA CGTGGGCTGA ACAACAGTAT GAAAAGAGA  400

GAAGTAAACG TTCAGTTCAA AAAGACTCAG CATTGGATCT CTTCAATGAT  450

CCAATGTGGA ATCAGCAGTG GTACTTGCAA GATACCAGAA TGACTGCAGC  500

TCTGCCCAAG CTGGACCTTC ATGTAATACC TGTTTGGGAA AAGGGTATTA  550

CTGGCAAAGG AGTTGTTATT ACTGTACTGG ATGATGGCTT GGAGTGGAAT  600

CACACAGACA TTTATGCCAA TTATGATCCA GAGGCTAGCT ATGATTTTAA  650

CGATAATGAT CATGATCCAT TTCCCCGATA TGATCTCACA AATGAAAACA  700

AACATGGAAC AAGATGTGCA GGTGAAATTG CCATGCAAGC AAATAATCAC  750

AAGTGTGGGG TTGGAGTTGC ATATAATTCC AAAGTTGGAG GCATAAGAAT  800
```

FIG. IB

```
GCTGGATGGC ATTGTAACTG ATGCCATTGA GGCTAGTTCA ATTGGATTCA 850

ACCCTGGCCA TGTGGATATT TACAGTGCAA GCTGGGCCC TAATGATGAT 900

GGAAAAACTG TGGAGGGGCC TGGCAGACTA GCCCAGAAGG CATTTGAATA 950

TGGTGTCAAA CAGGGGAGAC AAGGGAAAGG CTCCATCTTT GTCTGGGCTT 1000

CAGGGAATGG GGGTCGTCAG GGAGATAACT GTGACTGTGA TGGCTACACA 1050

GACAGCATTT ACACCATCTC TATCAGCAGT GCCTCCAGC AAGGCCTGTC 1100

ACCTTGGTAT GCAGAGAAGT GTTCTTCCAC ATTGGCTACC TCCTACAGCA 1150

GTGGTGATTA CACAGACCAG CGAATAACAA GCGCTGACCT GCACAATGAC 1200

TGCACAGAGA CCCACACAGG CACCTCGGCT TCAGCACCCC TGGCTGCTGG 1250

TATCTTTGCT CTGGCCTTGG AGGCAAACCC AAATCTTACC TGGAGAGATA 1300

TGCAGCATCT GGTTGTCTGG ACCTCTGAGT ACGACCCATT GGCCAGTAAC 1350

CCAGGTTGGA AAAAGAATGG GGCAGGCTTG ATGGTGAACA GCCGATTTGG 1400

ATTTGGCTTG CTAAATGCCA AAGCTCTGGT GGATTTGGCT GATCCTCGGA 1450

CCTGGAGAAA TGTGCCTGAG AAGAAAGAAT GTGTTGTAAA AGACAATAAC 1500

TTTGAGCCTA GAGCCCTGAA AGCTAATGGA GAAGTAATTG TTGAAATCCC 1550

AACAAGAGCT TGTGAAGGAC AAGAAAATGC TATCAAGTCT CTGGAACATG 1600

TGCAATTTGA AGCAACAATT GAATATTCTC GTAGAGGAGA CCTTCATGTC 1650
```

FIG. IC

```
ACACTCACTT CTGCTGTTGG AACCAGCACT GTACTGTTGG CTGAAAGGGA 1700

AAGAGATACA TCCCCCAATG GCTTTAAGAA TTGGGACTTC ATGTCTGTTC 1750

ATACATGGGG AGAGAATCCT GTAGGCACCT GGACATTGAA AATTACAGAC 1800

ATGTCTGGAA GAATGCAAAA TGAAGGAAGG ATTGTGAACT GGAAGTTGAT 1850

TTTGCATGG ACATCTTCTC AACCAGAGCA CATGAAGCAG CCCCGTGTGT 1900

ACACATCCTA CAATACAGTC CAGAATGACA GGAGAGGAGT GGAAAAGATG 1950

CCTGGTACCC AAAAACTCCA GCAGCAGCAA TGTGGAGGGT AGAAGGGATG 2050

AGCAGGTACA AGGAACTCCT TCAAAGGCCA TGCTGCGACT CCTACAAAGT 2100

GCTTTTAGCA AGAATGCACT TTCAAAACAA TCACCAAAGA AGTCTCCAAG 2150

TGCAAAGCTC AGCATCCCTT ATGAAAGTTT CTATGAAGCC TTGGAAAAGC 2200

TTAACAAGCC CTCCAAGCTT GAAGGCTCTG AAGACAGTCT GTACAGTGAC 2250

TATGTTGATG TATTCTATAA CACAAAACCT TATAAGCATA GAGATGACAG 2300

GCTGCTGCAA GCTCTCATGG ACATCCTAAA TGAGGAGAAT TAAAATAAGG 2350

AGCTC 2355
```

FIG. 2A

```
TCTAGATGCA TCTTCCCTCT TCGTCCCCTG CTCCACCACC CTGCGCGCCT  50

CACAGCCCCG CTTTTCACTC CCAAAGAAGG ATGGAGGGCG GTTGTGGATC  100

CCAGTGGAAG GCGGCCGGGT TCCTCTTCTG TGTGATGGTT TTTGCGTCTG  150

CCGAGAGACC CGTCTTCACG AATCATTTTC TTGTGGAGTT GCATAAAGAC  200

GGAGAGGAAG AGGCTCGCCA AGTTGCAGCA GAACACGGCT TTGGAGTCCG  250

AAAGCTCCCC TTTGCAGAAG GCCTGTATCA CTTTTATCAC AATGGGCTTG  300

CAAAGGCCAA AAGAAGACGC AGCCTACACC ATAAGCGGCA GCTAGAGAGA  350

GACCCCAGGA TAAAGATGGC GCTGCAACAA GAAGGATTTG ACCGTAAAAA  400

GAGAGGGTAC AGGGACATCA ATGAGATTGA CATCAACATG AATGATCCTC  450

TCTTTACAAA GCAATGGTAC CTGTTCAACA CTGGGCAAGC CGATGGAACT  500

CCTGGGCTAG ACTTGAACGT GGCCGAAGCC TGGGAGCTGG GATACACAGG  550

AAAAGGAGTG ACCATTGGAA TTATGGATGA TGGAATTGAC TATCTCCACC  600

CAGACCTGGC CTACAACTAC AACGCTGATG CAAGTTATGA CTTCAGCAGC  650

AATGACCCCT ACCCATACCC TCGATACACA GATGACTGGT TCAACAGCCA  700

TGGAACTAGG TGTGCAGGAG AAGTTTCTGC TGCAGCCAGC AACAATATCT  750

GTGGAGTCGG CGTAGCATAC AACTCCAAGG TGGCAGGGAT CCGGATGCTG  800

GACCAGCCCT TTATGACAGA CATCATCGAA GCCTCCTCCA TCAGCCACAT  850
```

FIG. 2B

```
GCCTCAACTG ATCGACATCT ACAGTGCAAG CTGGGGCCCC ACAGACAATG  900

GGAAGACGGT TGATGGGCCC CGAGAGCTCA CACTCCAGGC CATGGCTGAT  950

GGCGTGAACA AGGGCCGTGG GGGCAAAGGC AGCATCTATG TGTGGGCCTC 1000

TGGGGACGGT GGCAGCTACG ATGACTGCAA CTGTGACGGC TATGCTTCAA 1050

GCATGTGGAC CATCTCCATC AACTCAGCCA TCAATGATGG CAGGACTGCC 1100

TTGTATGATG AGAGTTGCTC TTCCACCTTA GCATCCACCT TCAGCAATGG 1150

GAGGAAGAGG AATCCTGAGG CTGGTGTGGC TACCACAGAC TTGTATGGCA 1200

ACTGTACTCT GAGACACTCT GGGACATCTG CAGCTGCTCC GGAGGCAGCT 1250

GGCGTGTTTG CATTAGCTTT GGAGGCTAAC CTGGATCTGA CCTGGAGAGA 1300

CATGCAACAT CTGACTGTGC TCACCTCCAA GCGGAACCAG CTTCATGATG 1350

AGGTTCATCA GTGGCGACGG AATGGGGTTG GCCTGGAATT TAATCACCTC 1400

TTTGGCTACG GAGTCCTTGA TGCAGGTGCC ATGGTGAAAA TGGCTAAAGA 1450

CTGGAAAACT GTTCCGGAGA GATTCCATTG TGTGGGAGGC TCTGTGCAGA 1500

ACCCTGAAAA AATACCACCC ACCGGCAAGC TGGTACTGAC CCTCAAAACA 1550

AATGCATGTG AGGGGAAGGA AAACTTCGTC CGCTACCTGG AGCACGTCCA 1600

AGCTGTCATC ACAGTCAACG CGACCAGGAG AGGAGACCTG AACATCAACA 1650
```

FIG. 2C

```
TGACCTCCCC AATGGGCACC AAGTCCATTT TGCTGAGCCG GCGTCCCAGA 1700

GACGACGACT CCAAGGTGGG CTTTGACAAG TGGCCTTTCA TGACCACCCA 1750

CACCTGGGGG GAGGATGCCC GAGGGACCTG GACCCTGGAG CTGGGGTTTG 1800

TGGGCAGTGC ACCACAGAAG GGGTTGCTGA AGGAATGGAC CCTGATGCTT 1850

CACGGCACAC AGAGCGCCCC ATACATCGAT CAGGTGGTGA GGGATTACCA 1900

GTCTAAGCTG GCCATGTCCA AGAAGCAGGA GCTGGAGGAA GAGCTGGATG 1950

AGGCTGTGGA GAGAAGCCTG CAAAGTATCC TGAGAAAGAA CTAGGGCCAC 2000

GCTTCCGAAT TC 2012
```

FIG. 3A

| | | | | | | | | | | | | | | |
|---|---|---|---|---|---|---|---|---|---|---|---|---|---|---|
| Met | Glu | Gln | Arg | Gly | Trp | Thr | Leu | Gln | Cys | Thr | Ala | Phe | Ala | Phe |
| 1 | | | | 5 | | | | | 10 | | | | | 15 |
| Phe | Cys | Val | Trp | Cys | Ala | Leu | Ser | Ser | Val | Lys | Ala | Lys | Arg | Gln |
| | | | | 20 | | | | | 25 | | | | | 30 |
| Phe | Val | Asn | Glu | Trp | Ala | Ala | Glu | Ile | Pro | Gly | Gly | Gln | Glu | Ala |
| | | | | 35 | | | | | 40 | | | | | 45 |
| Ala | Ser | Ala | Ile | Ala | Glu | Glu | Leu | Gly | Tyr | Asp | Leu | Leu | Gly | Gln |
| | | | | 50 | | | | | 55 | | | | | 60 |
| Ile | Gly | Ser | Leu | Glu | Asn | His | Tyr | Leu | Phe | Lys | His | Lys | Ser | His |
| | | | | 65 | | | | | 70 | | | | | 75 |
| Pro | Arg | Arg | Ser | Arg | Arg | Ser | Ala | Leu | His | Ile | Thr | Lys | Arg | Leu |
| | | | | 80 | | | | | 85 | | | | | 90 |
| Ser | Asp | Asp | Asp | Arg | Val | Thr | Trp | Ala | Glu | Gln | Gln | Tyr | Glu | Lys |
| | | | | 95 | | | | | 100 | | | | | 105 |
| Glu | Arg | Ser | Lys | Arg | Ser | Val | Gln | Lys | Asp | Ser | Ala | Leu | Asp | Leu |
| | | | | 110 | | | | | 115 | | | | | 120 |
| Phe | Asn | Asp | Pro | Met | Trp | Asn | Gln | Gln | Trp | Tyr | Leu | Gln | Asp | Thr |
| | | | | 125 | | | | | 130 | | | | | 135 |
| Arg | Met | Thr | Ala | Ala | Leu | Pro | Lys | Leu | Asp | Leu | His | Val | Ile | Pro |
| | | | | 140 | | | | | 145 | | | | | 150 |
| Val | Trp | Glu | Lys | Gly | Ile | Thr | Gly | Lys | Gly | Val | Val | Ile | Thr | Val |
| | | | | 155 | | | | | 160 | | | | | 165 |
| Leu | Asp | Asp | Gly | Leu | Glu | Trp | Asn | His | Thr | Asp | Ile | Tyr | Ala | Asn |
| | | | | 170 | | | | | 175 | | | | | 180 |
| Tyr | Asp | Pro | Glu | Ala | Ser | Tyr | Asp | Phe | Asn | Asp | Asn | Asp | His | Asp |
| | | | | 185 | | | | | 190 | | | | | 195 |
| Pro | Phe | Pro | Arg | Tyr | Asp | Leu | Thr | Asn | Glu | Asn | Lys | His | Gly | Thr |
| | | | | 200 | | | | | 205 | | | | | 210 |
| Arg | Cys | Ala | Gly | Glu | Ile | Ala | Met | Gln | Ala | Asn | Asn | His | Lys | Cys |
| | | | | 215 | | | | | 220 | | | | | 225 |
| Gly | Val | Gly | Val | Ala | Tyr | Asn | Ser | Lys | Val | Gly | Gly | Ile | Arg | Met |
| | | | | 230 | | | | | 235 | | | | | 240 |

FIG. 3B

```
Leu Asp Gly Ile Val Thr Asp Ala Ile Glu Ala Ser Ser Ile Gly
            245             250                     255
Phe Asn Pro Gly His Val Asp Ile Tyr Ser Ala Ser Trp Gly Pro
            260             265                     270
Asn Asp Asp Gly Lys Thr Val Glu Gly Pro Gly Arg Leu Ala Gln
            275             280                     285
Lys Ala Phe Glu Tyr Gly Val Lys Gln Gly Arg Gln Gly Lys Gly
            290             295                     300
Ser Ile Phe Val Trp Ala Ser Gly Asn Gly Gly Arg Gln Gly Asp
            305             310                     315
Asn Cys Asp Cys Asp Gly Tyr Thr Asp Ser Ile Tyr Thr Ile Ser
            320             325                     330
Ile Ser Ser Ala Ser Gln Gln Gly Leu Ser Pro Trp Tyr Ala Glu
            335             340                     345
Lys Cys Ser Ser Thr Leu Ala Thr Ser Tyr Ser Ser Gly Asp Tyr
            350             355                     360
Thr Asp Gln Arg Ile Thr Ser Ala Asp Leu His Asn Asp Cys Thr
            365             370                     375
Glu Thr His Thr Gly Thr Ser Ala Ser Ala Pro Leu Ala Ala Gly
            380             385                     390
Ile Phe Ala Leu Ala Leu Glu Ala Asn Pro Asn Leu Thr Trp Arg
            395             400                     405
Asp Met Gln His Leu Val Val Trp Thr Ser Glu Tyr Asp Pro Leu
            410             415                     420
Ala Ser Asn Pro Gly Trp Lys Lys Asn Gly Ala Gly Leu Met Val
            425             430                     435
Asn Ser Arg Phe Gly Phe Gly Leu Leu Asn Ala Lys Ala Leu Val
            440             445                     450
Asp Leu Ala Asp Pro Arg Thr Trp Arg Asn Val Pro Glu Lys Lys
            455             460                     465
Glu Cys Val Val Lys Asp Asn Asn Phe Glu Pro Arg Ala Leu Lys
            470             475                     480
```

FIG. 3C

```
Ala Asn Gly Glu Val Ile Val Glu Ile Pro Thr Arg Ala Cys Glu
             485             490                 495
Gly Gln Glu Asn Ala Ile Lys Ser Leu Glu His Val Gln Phe Glu
             500             505                 510
Ala Thr Ile Glu Tyr Ser Arg Arg Gly Asp Leu His Val Thr Leu
             515             520                 525
Thr Ser Ala Val Gly Thr Ser Thr Val Leu Leu Ala Glu Arg Glu
             530             535                 540
Arg Asp Thr Ser Pro Asn Gly Phe Lys Asn Trp Asp Phe Met Ser
             545             550                 555
Val His Thr Trp Gly Glu Asn Pro Val Gly Thr Trp Thr Leu Lys
             560             565                 570
Ile Thr Asp Met Ser Gly Arg Met Gln Asn Glu Gly Arg Ile Val
             575             580                 585
Asn Trp Lys Leu Ile Leu His Gly Thr Ser Ser Gln Pro Glu His
             590             595                 600
Met Lys Gln Pro Arg Val Tyr Thr Ser Tyr Asn Thr Val Gln Asn
             605             610                 615
Asp Arg Arg Gly Val Glu Lys Met Val Asn Val Val Glu Lys Arg
             620             625                 630
Pro Thr Gln Lys Ser Leu Asn Gly Asn Leu Leu Val Pro Lys Asn
             635             640                 645
Ser Ser Ser Ser Asn Val Glu Gly Arg Arg Asp Glu Gln Val Gln
             650             655                 660
Gly Thr Pro Ser Lys Ala Met Leu Arg Leu Leu Gln Ser Ala Phe
             665             670                 675
```

FIG. 3D

Ser Lys Asn Ala Leu Ser Lys Gln Ser Pro Lys Lys Ser Pro Ser
                680                 685                 690

Ala Lys Leu Ser Ile Pro Tyr Glu Ser Phe Tyr Glu Ala Leu Glu
                695                 700                 705

Lys Leu Asn Lys Pro Ser Lys Leu Glu Gly Ser Glu Asp Ser Leu
                710                 715                 720

Tyr Ser Asp Tyr Val Asp Val Phe Tyr Asn Thr Lys Pro Tyr Lys
                725                 730                 735

His Arg Asp Asp Arg Leu Leu Gln Ala Leu Met Asp Ile Leu Asn
                740                 745                 750

Glu Glu Asn
753

FIG. 4A

```
Met Glu Gly Gly Cys Gly Ser Gln Trp Lys Ala Ala Gly Phe Leu
 1               5                  10                  15

Phe Cys Val Met Val Phe Ala Ser Ala Glu Arg Pro Val Phe Thr
                20                  25                  30

Asn His Phe Leu Val Glu Leu His Lys Asp Gly Glu Glu Glu Ala
                35                  40                  45

Arg Gln Val Ala Ala Glu His Gly Phe Gly Val Arg Lys Leu Pro
                50                  55                  60

Phe Ala Glu Gly Leu Tyr His Phe Tyr His Asn Gly Leu Ala Lys
                65                  70                  75

Ala Lys Arg Arg Arg Ser Leu His His Lys Arg Gln Leu Glu Arg
                80                  85                  90

Asp Pro Arg Ile Lys Met Ala Leu Gln Gln Glu Gly Phe Asp Arg
                95                 100                 105

Lys Lys Arg Gly Tyr Arg Asp Ile Asn Glu Ile Asp Ile Asn Met
               110                 115                 120

Asn Asp Pro Leu Phe Thr Lys Gln Trp Tyr Leu Phe Asn Thr Gly
               125                 130                 135

Gln Ala Asp Gly Thr Pro Gly Leu Asp Leu Asn Val Ala Glu Ala
               140                 145                 150

Trp Glu Leu Gly Tyr Thr Gly Lys Gly Val Thr Ile Gly Ile Met
               155                 160                 165
```

FIG. 4B

```
Asp Asp Gly Ile Asp Tyr Leu His Pro Asp Leu Ala Tyr Asn Tyr
            170                 175                 180

Asn Ala Asp Ala Ser Tyr Asp Phe Ser Asn Asp Pro Tyr Pro
            185                 190                 195

Tyr Pro Arg Tyr Thr Asp Asp Trp Phe Asn Ser His Gly Thr Arg
            200                 205                 210

Cys Ala Gly Glu Val Ser Ala Ala Ala Ser Asn Asn Ile Cys Gly
            215                 220                 225

Val Gly Val Ala Tyr Asn Ser Lys Val Ala Gly Ile Arg Met Leu
            230                 235                 240

Asp Gln Pro Phe Met Thr Asp Ile Ile Glu Ala Ser Ser Ile Ser
            245                 250                 255

His Met Pro Gln Leu Ile Asp Ile Tyr Ser Ala Ser Trp Gly Pro
            260                 265                 270

Thr Asp Asn Gly Lys Thr Val Asp Gly Pro Arg Glu Leu Thr Leu
            275                 280                 285

Gln Ala Met Ala Asp Gly Val Asn Lys Gly Arg Gly Gly Lys Gly
            290                 295                 300

Ser Ile Tyr Val Trp Ala Ser Gly Asp Gly Gly Ser Tyr Asp Asp
            305                 310                 315

Cys Asn Cys Asp Gly Tyr Ala Ser Ser Met Trp Thr Ile Ser Ile
            320                 325                 330
```

FIG. 4C

Asn Ser Ala Ile Asn Asp Gly Arg Thr Ala Leu Tyr Asp Glu Ser
                    335                 340                 345

Cys Ser Ser Thr Leu Ala Ser Thr Phe Ser Asn Gly Arg Lys Arg
                    350                 355                 360

Asn Pro Glu Ala Gly Val Ala Thr Thr Asp Leu Tyr Gly Asn Cys
                    365                 370                 375

Thr Leu Arg His Ser Gly Thr Ser Ala Ala Ala Pro Glu Ala Ala
                    380                 385                 390

Gly Val Phe Ala Leu Ala Leu Glu Ala Asn Leu Asp Leu Thr Trp
                    395                 400                 405

Arg Asp Met Gln His Leu Thr Val Leu Thr Ser Lys Arg Asn Gln
                    410                 415                 420

Leu His Asp Glu Val His Gln Trp Arg Arg Asn Gly Val Gly Leu
                    425                 430                 435

Glu Phe Asn His Leu Phe Gly Tyr Gly Val Leu Asp Ala Gly Ala
                    440                 445                 450

Met Val Lys Met Ala Lys Asp Trp Lys Thr Val Pro Glu Arg Phe
                    455                 460                 465

His Cys Val Gly Gly Ser Val Gln Asn Pro Glu Lys Ile Pro Pro
                    470                 475                 480

Thr Gly Lys Leu Val Leu Thr Leu Lys Thr Asn Ala Cys Glu Gly
                    485                 490                 495

FIG. 4D

Lys Glu Asn Phe Val Arg Tyr Leu Glu His Val Gln Ala Val Ile
                500                 505             510

Thr Val Asn Ala Thr Arg Arg Gly Asp Leu Asn Ile Asn Met Thr
                515                 520             525

Ser Pro Met Gly Thr Lys Ser Ile Leu Leu Ser Arg Arg Pro Arg
                530                 535             540

Asp Asp Ser Lys Val Gly Phe Asp Lys Trp Pro Phe Met Thr Val
                545                 550             555

Thr His Thr Trp Gly Glu Asp Ala Arg Gly Thr Trp Thr Leu Glu
                560                 565             570

Leu Gly Phe Val Gly Ser Ala Pro Gln Lys Gly Leu Leu Lys Glu
                575                 580             585

Trp Thr Leu Met Leu His Gly Thr Gln Ser Ala Pro Tyr Ile Asp
                590                 595             600

Gln Val Val Arg Asp Tyr Gln Ser Lys Leu Ala Met Ser Lys Lys
                605                 610             615

Gln Glu Leu Glu Glu Leu Asp Glu Ala Val Glu Ala Val Ser Leu
                620                 625             630

Gln Ser Ile Leu Arg Lys Asn
                635     637

FIG. 5
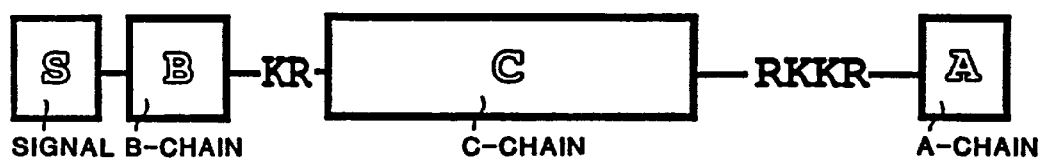
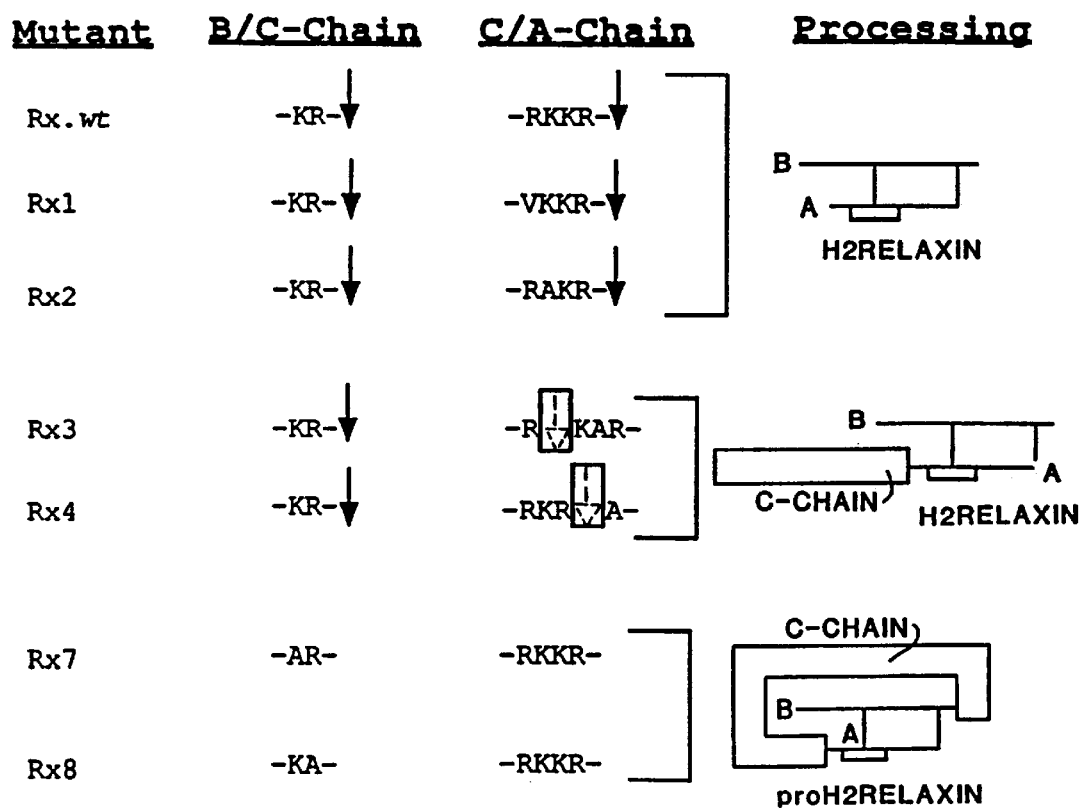

NON-ENDOCRINE ANIMAL HOST CELLS CAPABLE OF EXPRESSING VARIANT PROINSULIN AND PROCESSING THE SAME TO FORM ACTIVE, MATURE INSULIN AND METHODS OF CULTURING SUCH CELLS

CROSS REFERENCE TO RELATED APPLICATION

This is a continuation-in-part of International Application No. PCT/US92/10621 filed Dec. 4, 1992, now inactive, which is a continuation-in-part of application U.S. Ser. No. 07/887,265 filed May 22, 1992, now abandoned, which is a continuation-in-part of application U.S. Ser. No. 07/803,631 filed Dec. 6, 1991, now abandoned, to which applications priority is claimed under 35 U.S.C. §§120 and 365.

BACKGROUND OF THE INVENTION

1. Field of the Invention

This invention relates to host cells expressing one or more prohormone convertase enzymes and the production of a biologically active polypeptide from these cells. The invention further relates to polypeptide precursor variants having endoprotease cleavage sites which are processed by the host cell.

2. Description of Related Art

Most, if not all proteinaceous hormones are synthesized as relatively large precursor molecules, prohormones, that are biologically inactive (reviewed in Docherty and Steiner 1982; Loh et al. 1984; Mains et al. 1980). Maturation of the prohormone to its active form often requires endoproteolytic cleavage at paired or multiple basic amino acid residues to liberate the active component from the inactive portion of the precursor molecule. Until recently, almost nothing was known concerning the identity of the proteins responsible for this important stage in processing: the prohormone convertase (PC) enzymes.

Not every kind of cell has the capacity to correctly convert a prohormone to its active mature form through these specific cleavages. For some classes of prohormone this processing is apparently limited to those cells that contain both constitutive and regulated pathways of protein secretion (Gumbiner and Kelly 1982). Cells having both constitutive and regulated pathways of protein secretion are located almost exclusively in the specialized hormone-producing tissues of the endocrine and neuroendocrine systems.

An example of a family of hormones that is processed during regulated secretion is the insulin family of hormones. This family includes insulin, the insulin-like growth factors IGF-I and IGF-II, and relaxin. In their native environment, all members of this family are synthesized as precursor molecules that require processing to yield active hormone.

When heterologously expressed in cells having only a constitutive pathway of protein secretion, most hormone precursors, such as human preproinsulin, are secreted in an unprocessed prohormone form (Gumbiner and Kelly 1982). Experimental manipulation of mouse AtT-20 cells that disrupted the regulated secretory pathway of those cells has been observed to redirect the polyhormone precursor proopiomelanocortin (POMC) into the constitutive secretory pathway. In that case, POMC was no longer subjected to processing and was found to be secreted from the cell as the intact precursor (Moore et al. 1983). These observations suggest that there is a class of processing enzymes that function only in the regulated pathway of protein secretion; this pathway is apparently limited to certain highly-specialized cell types.

The POMC protein is a prohormone that is subject to differential processing. Expression of mature POMC derivatives is highly tissue-specific; alternate processed forms of the same prohormone precursor are produced in different regions of the brain (Douglass et al. 1984). The enzyme(s) and control mechanisms involved in the generation of this diversity are unknown. The possibility exists that there are tissue-specific enzymes that recognize unique amino acid sites on the prohormone substrate, or alternatively, that only one enzyme is responsible for the endoproteolytic cleavage and is itself under tight metabolic control, with each tissue providing a characteristic intracellular environment that is associated with cleavage at a specific subset of residue pairs.

Until recently, the only known eukaryotic prohormone processing enzyme was the KEX2 gene product of the yeast *Saccharomyces cerevisiae* (Jullius et al. 1983 and 1984; Fuller et al. 1989a.) The kex2 protein is a serine protease related to the subtilisin family of enzymes and has a preference for specific pairs of basic amino acids on its native hormone precursor substrates (pro-a-factor mating type pheromone and the pro-killer toxin). Kex2 shows maximum enzymatic activity at neutral pH with a strict requirement for the presence of calcium (Julius et al. 1984; Fuller et al. 1989a). It is membrane-bound and the mature, active form of the enzyme is localized in the post-Golgi compartment of the yeast cell (Fuller et al. 1989b; Redding et al. 1991). It can effectively serve as a substitute convertase for bona fide mammalian PC enzymes when heterologously expressed in otherwise processing-deficient cells by its demonstrated ability to correctly process certain mammalian prohormones: Nerve growth factor, bNGF, in BSC-40 cells (Bresnahan et al. 1990); protein C in baby hamster kidney BHK cells (Foster et al. 1991); POMC both in BSC-40 cells (Thomas et al. 1988) and in COS-1 cells (Zollinger et al. 1990)]. Kex2 was shown to have a highly similar if not identical substrate specificity to the authentic human proalbumin convertase in vitro (Bathurst et al. 1986; Brennan et al. 1990). When heterologously expressed in mammalian cells kex2 will home to the post-Golgi compartment, where it is apparently fully active (Germain, et al. 1990). These observations have led to speculation that this yeast protein must be both functionally and structurally similar to an authentic mammalian convertase. A search began for the elusive mammalian counterparts of kex2 based upon structural homologies.

KEX2 and Fur Hydrophobic Anchor

The Kex2 endoprotease has two hydrophobic regions located at the N-terminal side and C-terminal side. The C-terminal hydrophobic transmembrane anchor is responsible for the anchoring of the Kex2 to a Golgi body of a yeast cell. Deletion of this C-terminal hydrophobic anchor renders the Kex2 endoprotease soluble while still maintaining substrate specificity (EPO PUB No.0327377).

An inspection of genetic data bases identified a potential mammalian homologue of kex2 that shared many features of the active site domain of the kex2 protein: the fur gene product of human liver, furin (Fuller et al. 1989b). Furin was subsequently cloned and successfully expressed in processing-deficient cells: cotransfection of furin with pro-von Willebrand factor in COS-1 cells (van den Ven et al. 1990; Wise et al. 1990) and with pro-bNGF in African green monkey kidney epithelial BSC-40 cells (Bresnahan et al. 1990) resulted in correct processing of the precursor substrates.

However, when furin and a prohormone, prorenin, have been coexpressed in mammalian cells, no processing has been observed (Hatsuzawa, et al *The Journal of Biological Chemistry* Vol 265 [1990]).

Furin also shared with kex2 a requirement for calcium ions, displayed maximum activity at a neutral pH, and, like kex2, was shown to be a membrane-bound protein in the post-Golgi compartment (Bresnahan et al. 1990). However, because furin does not seem to be capable of efficiently processing certain hormone precursors such as prorenin, and its mRNA message is apparently expressed in most if not all mammalian cells (Hatsuzawa et al. 1990), the furin protease may play a role in an essential "housekeeping" function in that it could be responsible for many of the basic amino acid site cleavages occurring in the constitutive secretory pathway of the cell. These functions could be general, or more confined to specific cell-types with the constitutive pathway-dependent processing of growth factors like bNGF.

Because furin does not appear to be directly involved in the endoproteolytic processing of prohormones in endocrine-like tissues, there must be other mammalian proteins both functionally and structurally similar to furin and yeast kex2 that serve as the authentic prohormone convertases: PC proteins that share distinctive homologies in their active sites. This search for structural homology has recently lead to the discovery of more PC proteins.

By using the technique of "Mixed Oligonucleotides Primed Amplification of cDNA" (MOPAC, Innis 1990), Smeekens and Steiner (1990) were able to use the conservation of amino acid sequence surrounding the active sites of both bacterial subtilisin and the yeast kex2 protease to amplify a putative prohormone convertase cDNA from human insulinoma. This PC cDNA, termed mPC2, showed an exceptional degree of homology to the yeast kex2 protease. In similar experiments Seidah and colleagues identified another member of the subtilisin family of proteases, termed, mPC1 (Seidah, et al 1991).

The distribution of PC1 and PC2 has so far been observed to be confined to neuroendocrine-derived tissues (Seidah et al. 1990; Seidah et al. 1991; Smeekens et al. 1991), suggesting that these proteins may be candidates for the authentic convertases resident in the regulated secretory pathways of these tissues. The substrate specificities of PC1 and PC2 for defined pairs of dibasic amino acids at the prohormone cleavage sites do not appear to be identical (Benjannet et al. 1991; Thomas et al. 1991), nor do they share the same pattern of tissue distribution in the brain (Seidah et al. 1991). This implies that different classes of prohormones may require unique PC enzymes, and that both PC1 and PC2 may be members of a family of specific processing enzymes employed by the endocrine system to generate the diversity of hormones required throughout the entire organism.

Precursor processing

The biosynthetic process begins with the synthesis of the precursor (prepropeptide) on the rough endoplasmic reticulum (RER). The signal peptide (pre-portion) is clipped off as the proprotein is transported into the cisternae of the RER where protein folding, di-sulfide bond formation and asparagine-linked glycosylation occur (FIG. 1). The precursor is then translocated to the Golgi apparatus where more complex glycosylation and phosphorylation occur. Within the Golgi of some cells, proteins are sorted by an unknown mechanism into two groups: those that will be constitutively secreted and those that undergo regulated secretion. The constitutively secreted proteins will enter vesicles and be transported to their target continually without the need for any specific stimulus. Proteins undergoing regulated secretion are transported to secretory vesicles and will be released only when an adequate stimulus is provided. Within the secretory vesicles the excision of bioactive peptides from the larger inactive protein precursors occurs. Two steps involved in this process are endoproteolytic cleaveage usually at the carboxyl side of paired basic amino acids (e.g. lys-arg, arg-arg) and exoproteolytic cleavage of flanking basic amino acids by carboxyl- and/or aminopeptidases (reviewed in Mains et al. 1990.).

Many proteins, including NGF (Berger and Shooter 1977), are first synthesized as larger precursor proteins. The function of the precursor is still not well understood. One possible role of the precursor is to aid in protein folding (Steiner 1982, Selby et al. 1987, Wise et al. 1988). The precursor may also direct the protein to the proper location or pathway within the cell as is suggested by Sevarino and colleagues (1989), though this is not the case with the connecting peptide of insulin (Powell et al. 1988, Gross et al. 1990). Additionally, the precursor has been shown to have roles in gamma carboxylation of glutamic acid residues (Pan and Price 1985, Furie and Furie 1988), and regulation of the coordinate synthesis of multiple mature peptides from a single precursor polypeptide eg., POMC. (For review, see Douglass et al. 1984).

Relaxin

In the present invention, prorelaxin is used as a typical hormone precursor. The relaxin is first synthesized as a preprohormone precursor which undergoes specific processing to form the mature two-chain, dilsulfide-linked active relaxin. A major part of this processing requires endoproteolytic cleavage at specific pairs of basic amino acid residues. This specific processing does not occur when the precursor is heterologously expressed in cells containing only the constitutive pathway of protein secretion. Mature human relaxin in an ovarian hormonal peptide of approximately 6000 daltons in molecular weight known to be responsible for remodeling the reproductive tract before parturition, thus facilitating the birth process. Hisaw, F. L., *Proc. Soc. Exp. Biol. Med.,* 23:61–663 (1926); Schwabe, C. et al., *Biochem. Biophys. Res. Comm.,* 75: 503–570 (1977); James, R. et al., *Nature,* 267: 544–546 (1977). This protein appears to modulate the restructuring of connective tissues in target organs to obtain the required changes in organ structure during pregnancy and parturition. Some of the important roles for relaxin as a pregnancy hormone include inhibition of premature labor and cervical ripening at parturition. While predominantly a hormone of pregnancy, relaxin has also been detected in the non-pregnant female as well as in the male. Bryant-Greenwood, G. D., *Endocrine Reviews,* 3: 62–90 (1982) and Weiss, G., *Ann. Rev. Physiol.,* 46: 43–52 (1984).

Relaxin consists of two polypeptide chains, referred to as A and B, joined by dusulfide bonds with an intra-chain disulfide loop in the A-chain in a manner analogous to that of insulin. Two human genes (H1 and H2) for human relaxin have been identified, and only H2 is expressed in the ovary. Porcine relaxin, the sequence of which has also been determined, has been used in human clinical trials for ripening of the cervix and induction of labor. MacLennan et al., *Obstetrics & Gynecology,* 68: 598 (1986).

European Pat. Publ. No. 86,649 published Aug. 24, 1983 discloses how to prepare procine preprorelaxin, porcine prorelaxin, and porcine relaxin. Australian Pat. No. 561,670 issued Aug. 26, 1987, European Pat. Publ. No. 68,375 published Jan. 5, 1983, and Haley et al., DNA, 1: 155–162 (1982) disclose how to prepare porcine relaxin. European Pat. Publ. Nos. 101,309 published Feb. 22, 1984 and 112, 149 published Jun. 27, 1984 respectively disclose the molecular cloning and characterization of a gene sequence coding for human relaxin and human H2-relaxin and analogs thereof. U.S. Pat. No. 4,267,101 issued May 12, 1981 discloses a process for obtaining human relaxin from fetal membranes.

Nerve Growth Factor

Nerve growth factor (NGF), required for sympathetic and sensory neuron survival (Levi-Montalcini and Booker 1960, Gorin and Johnson 1979), is the most well characterized neurotrophic factor in part due to the exceptionally high levels synthesized in the male mouse submaxillary gland. It was from this source that NGF was purified (Cohen 1960) and its complete amino acid sequence determined (Angeletti 1973). Using this information, Scott and colleagues (1983) identified and cloned the mouse NGF gene by screening a mouse submaxillary gland cDNA library using a probe constructed for a hexapeptide based on the least degenerate codons contained within the NGF sequence. Molecular cloning, using the polymerase chain reaction (PCR) (Saiki et al. 1985, Mullis et al. 1986), has recently revealed that NGF is a member of a family of neurotrophic factors that also includes BDNF (Leibrock et al. 1989) and NT-3 (Hohn et al. 1990, Rosenthal et al. 1990, Maisonpierre et al. 1990a, Ernfors et al. 1990, Jones and Reichardt 1990).

NGF, BDNF and NT-3 are all translated as preproproteins that require endoproteolytic cleavage in order to be active. There is an extensive amount of homology (>50%) between the mature portions of NGF, BDNF, and NT3. However, the homologies of the precursor portions are much lower (~20%). The efficiency of processing of the three neurotrophic factors, from their inactive pro-form to the active factor, vary substantially with different cell types.

Insulin

Insulin is a polypeptide hormone which is produced in the beta cells of the islets of Langerhans situated in the pancreas of all vertebrates. Insulin is secreted directly into the bloodstream where it regulates carbohydrate metabolism, influences the synthesis of protein and of RNA, and the formation and storage of neutral lipids, *The Merck Index,* 10th edition, 1983 Insulin promotes anabolic processes and inhibits catabolic ones in muscle, liver and adipose tissue. The structure of human insulin was disclosed in Nature 187,483 (1960). Prior to the discovery of recombinant DNA technology, the major source of insulin for human consumption was the pancreases of slaughtered animals. Human insulin was among the first commercial health care products produced by recombinant technology. A review of the research, development, and recombinant production of human insulin is in *Science* 219, 632–637 (1983).

Glucose regulation of insulin responsiveness

Circulating insulin levels are regulated by several small molecules including glucose, amino acids, fatty acids and certain pharmacological agents. (Selden, et al., Nature vol. 321 pg 525–528 [1986]). When ambient glucose is detected by the a and b cells of pancreatic islets, they consequently secrete either glucagon, which stimulates glucose release from liver, or insulin, which induces glucose storage in liver and stimulates glucose uptake by muscle and adipocytes. (Thorens et al, Diabetic Care, vol. 13, no. 3, pgs. 209–218 [1990]).

Glucose stimulates de novo insulin biosynthesis by increasing transcription, mRNA stability, translation, and protein processing. Glucose also rapidly stimulates the release of pre-stored insulin. While glucose and non-glucose secretagogues may ultimately work through the same pathway, the biochemical events leading from changes in the levels in a particular fuel to insulin secretion are initially diverse. In the case of glucose, transport into the b-cell and metabolism are absolute requirements for insulin secretion. (WO 92/21756, published Dec. 10, 1992).

The cellular uptake of glucose is accomplished by membrane-associated carrier proteins that bind and transfer it across the lipid bilayer. Two classes of glucose carriers have been identified in mammalian cells, the Na+-glucose cotransporter and the facilitative glucose transporter (GLUT). Five members of the GLUT family have been identified: GLUT 1, expressed in erythrocytes; GLUT 2, expressed in liver; GLUT 3, expressed in brain; GLUT 4, expressed in muscle and fat cells; and GLUT 5, expressed in small intestine. (Bell et al., Diabetes Care, vol. 13, no. 3, pg. 198–208 [1990]). GLUT 2 is unique among the five member family of glucose transporters in that it has a higher Km and Vmax for glucose. (WO 92/21756, published Dec. 10, 1992).

GLUT 2 and the phosphorylating enzyme, glucokinase have been implicated in the control of glucose metabolism in islet b cells. Glucokinase is the high Km and high Vmax counterpart of GLUT 2 among the family of hexokinases. GLUT 2 and glucokinase have been hypothesized to be the glucose sensing apparatus that modulates insulin secretion in response to changes in circulating glucose concentrations by regulating glycolytic flux. (WO 92/21756, published Dec. 10, 1992).

Hexokinase performs the same function as glucokinase (glucose phosphorylation) but does so at much lower glucose concentrations (hexokinase has a Km for glucose of approximately 0.05 mM versus a 8 mM for glucokinase).

Cuif et al., (Mol Cell Biol 12 (11) p4852–61 [1992]), report identification of a glucose-response element of an enzyme, L-type pyruvate, in transgenic mice. Cuif et al., Supra indicate that the proximal region between −183 and +11 bp confers tissue-specificity and contains all the information necessary for the dietary and hormonal control of the L-PK gene expression in vivo, and further identify distal sequences that modulate transcriptional activity in a tissue specific manner.

In addition to its role in vivo, insulin is also useful in recombinant cell culture. Insulin is an example of a polypeptide factor important for mammalian cell culture proliferation and anabolism. Some cell cultures produce endogenous insulin and some do not; cell cultures which rely on added insulin are problematic because insulin is unstable in some cultures. European publication number, 0307247A2, published Mar. 3, 1989, describes the introduction of nucleic acid encoding insulin into a mammalian host cell to eliminate the need for adding exogenous insulin.

Insulin is synthesized as a larger precursor protein, proinsulin. Proinsulin is a single polypeptide chain containing a sequence of about thirty residues that is absent from mature insulin. Proinsulin, like prorelaxin, has a B-C-A chain structure. The C or connecting peptide joins the carboxyl end of the B chain and the amino terminus of the A chain of the future insulin molecule *Biochemistry 3rd edition,* pg. 995 (1988). The mature insulin is generated by cleavage of the C peptide at dibasic residues Arg(31)-Arg (32) and Lys(64)-Arg(65). Two distinct processing enzymes have been defined which are specific for their respective dibasic cleavage sites in proinsulin; type I is substrate specific for the BC junction, while type II is specific for the CA junction (Weiss, Biochemistry 29, 1990).

Naturally occurring mutations in the human insulin gene have been reported by Steiner et al. (*Diabetes Care* vol. 13, no. 6 pg. 600–609 [1990]). Members of a family with hyperproinsulinemia have a substitution of insulin B chain residue 10, a histidine, with aspartic acid resulting in a proinsulin that is reported to exhibit altered subcellular sorting behavior. In patients having hyperproinsulinemia, a significant proportion of the newly synthesized Asp-10 proinsulin is secreted from the islets in an unprocessed form via an unregulated or constitutive protein secretory pathway (Steiner et al. *PNAS USA*, vol. 85, pg. 8943–8947 [1988]) and (Quinn et al. *The J. Cell Bio,* vol. 113, pg. 987–996 [1991]). Others have shown that insulin containing this B10 H>D mutation results in a more active form of insulin with increased binding to the insulin receptor (Schwartz, et al. *PNAS USA* vol. 84, pp. 6408–6411 [1987]; Brange et al. *Nature* vol 333 pg 679–682 [1988]; Shoelson et al. vol. *Biochem.* vol. 31 pg 1757–1767 [1992]). Brems et al. (*Protein Engineering* vol. 5 no. 6 pg 519–525 [1992]) report that the replacement of B-chain residue 10, a histidine, with aspartic acid increased the stability of the insulin. Wild-type human insulin exhibits subunit interactions and forms dimers; dimeric insulin binds to $Zn^{2+}$ to form hexamers. The histidine residue at position B10 in insulin is involved in co-ordinating zinc ions and it has been reported by Quinn et al. Supra, that the human insulin mutant, B10 histidine to aspartic acid, allows formation of dimers of human proinsulin but not hexamers.

Insulin Like Growth Factor I and II (IGF-I and IGF-II)

Insulin-like growth factors, or IGFs, by definition are polypeptides with insulin-like structural and biologic properties which are not neutralized by the presence of excess anti-insulin antibodies. (*Endocrinology and Metabolism* 2nd ed. [1987]). The complete amino acid sequences of IGF-I and IGF-II have been determined (Rinderknecht, et al *Journal of Biological Chemistry* 253 pg. 2769 [1978]; Rinderknecht et al *FEBS Letters* 89, 283 [1978]). They are both single-chain polypeptides with three disulfide bridges and a sequence identity of 49 and 47 percent respectively, to human insulin A and B chains. The connecting peptide or C region is considerably shorter than the one of proinsulin and does not show any significant homology to it. The IGF-I peptide is not cleaved during the processing to the mature molecule. In addition, IGF-I contains a short, 8 amino-acid, carboxyterminal extension peptide, termed the D domain, for which no homologous region exists in insulin (Foyt, H. L., *Insulin-Like Growth Factors: Molecular and Cellular Aspects* [1991])

Both IGF-I and IGF-II are derived from precursors by proteolytic processing (Jansen et al *Nature* 306, 609 [1984]; Bell, et al *Nature* 310, 775 [1984]; Jansen et al *FEBS letters* 179, 243 [1985].

There exists a need for a method of producing polypeptides from their polypeptide precursors in cell culture. It is therefore an object of the present invention to provide host cells that express active prohormone convertases that cleave polypeptide precursors to polypeptides. It is also an object of the present invention to provide a method for the production of a desired polypeptide in cell culture in a manner that results in the proper processing and glycosylation of the desired polypeptide. A related objective of the present invention is the production of polypeptide hormones, such as insulin, relaxin, and IGF-I.

A further object of the present invention relates to providing polypeptide precursor mutants having prohormone convertase cleavage sites for processing by the host cell.

There also exists a need to eliminate problems associated with supplying necessary polypeptide factors (e.g. insulin or transferrin) for the maintenance and growth of recombinant host cells. This need is particularly evident in the use of mammalian cell culture in the production of commercial polypeptides such as pharmaceutical products. It is therefore an object of the present invention to provide mammalian cell cultures that express prohormone convertases that enable processing of polypeptide factor precursors to polypeptide factors needed for mammalian cell culture proliferation and anabolism. It is an object of the present invention to produce polypeptide factors using host cells expressing prohormone convertases.

These and other objects of the invention will be apparent to the ordinary artisan upon consideration of the specification as a whole.

SUMMARY OF THE INVENTION

The present invention describes a method for the production of a desired polypeptide in host cells expressing a prohormone convertase. In one embodiment the desired polypeptide is a prohormone processed to active hormone. In another embodiment, the desired polypeptide is any polypeptide factor needed for cell growth or anabolism. In some embodiments, the invention provides polypeptide factor mutants comprising as cleavage site recognizable by a host cell enzyme, such as a prohormone convertase. In a preferred embodiment, a prohormone convertase precursor is provided which is modified to have a host cell cleavage site allowing for processing of the prohormone convertase precursor to active enzyme in the host cell.

In one embodiment the host cell constitutively expresses a prohormone convertase. In another embodiment, the host cell is stably transformed with a prohormone convertase.

In one aspect of the present invention the production of a heterologous polypeptide factor, such as insulin or transferrin, in a polypeptide factor-depending host cell is accomplished by a) introducing into the polypeptide factor-dependent host cell nucleic acid encoding a heterologous polypeptide factor precursor comprising a cleavage site recognizable by a host cell enzyme and wherein said host cell is dependent on the cleavage product of said polypeptide factor precursor; and b) culturing said host cell under conditions wherein the polypeptide factor precursor is cleaved at said cleavage site by the host cell enzyme, thereby producing said polypeptide factor.

In another aspect of the present invention the production of a desired polypeptide in a host cell expressing a prohormone convertase is accomplished by a) introducing into the host cell nucleic acid encoding a desired polypeptide; and b) culturing said host cell under conditions wherein said desired polypeptide is expressed. Preferably the desired polypeptide is a polypeptide hormone and may be any polypeptide hormone. Preferably, it may be any polypeptide hormone comprised of two or more polypeptide chains. Among the preferred two-chain hormones are insulin, relaxin, and insulin-like growth factors I or II. Among the preferred prohormones are proinsulin, prorelaxin, and precursors of insulin-like growth factors I or II. The prohormone may be a prohormone mutant modified to contain one or more prohormone convertase cleavage sites. The prohormone or prohormone mutant may be processed by the prohormone convertase in an in vivo or in vitro manner.

The method of producing polypeptide hormones may be further accomplished by inserting into a prohormone, a prohormone convertase cleavage site that facilitates processing by a prohormone convertase. The preferred hormone is a mammalian polypeptide hormone comprised of two or more polypeptide chains, for example insulin, relaxin, insulin-like growth factor I or insulin like growth factor II.

In another aspect, the method may be practiced using cells transformed to contain a prohormone convertase fused to a hydrophobic transmembrane Golgi anchor, such as that from kex2 or furin.

The present invention discloses nucleic acid (a) encoding murine prohormone convertases 1 and 2, (b) mutants of prohormone convertase that contain inserted convertase cleavage sites, and (c) mutants of prohormone convertase that contain hydrophobic anchor domains, or heterologous pre and prepro sequences from other processed polypeptides. Also disclosed are vectors containing such nucleic acid and cells expressing such nucleic acid. Methods of effecting transformation and methods of providing transformed mammalian cells are disclosed.

BRIEF DESCRIPTION OF THE FIGURES

FIGS. 1A–1C AtT20 murine prohormone convertease 1 cDNA (SEQ ID NO:1)

FIGS. 2A–2C AtT20 murine prohormone convertase 2 cDNA (SEQ ID NO:2)

FIGS. 3A–3D Murine PC1 amino acid (SEQ ID NO:3)

FIGS. 4A–4D Murine PC2 amino acid (SEQ ID NO:4)

FIG. 5 Relaxin dibasic cleavage site mutants

DESCRIPTION OF THE PREFERRED EMBODIMENTS

Definitions

The term "desired polypeptide" refers to any polypeptide intended to be produced in a host cell, but which the host cell either normally does not produce or produces in small amounts, and which is not normally necessary for the continued existence of the cell. Desired polypeptides include a polypeptide having as few as about five amino acids as well as much larger proteins such as factor VIII (2332 amino acids). Desired polypeptides also include any molecule having a pre- or prepro-amino acid sequence, as well as amino acid or glycosylation variants (including natural alleles) capable of exhibiting a biological activity in common with the desired protein. Preferably the polypeptide is heterologous to the host cell in which it is made and is a human polypeptide. Preferred polypeptides are those that have pharmaceutical utility, such as: growth hormones, including human growth hormone, des-N-methionyl human growth hormone, and bovine growth hormone; parathyroid hormone; thyroid stimulating hormone; thyroxine; insulin; follicle stimulating hormone; calcitonin; leutinizing hormone; glucagon; factor VIII; bombesin; factor IX, thrombin; hemopoietic growth factor; tumor necrosis factor-alpha and -beta; relaxin mouse gonadotropin-associated peptide; tissue factor protein; inhibin; activin; vascular endothelial growth factor; thrombopoietin; rheumatoid factors; nerve growth factor such as NGF-b; platelet-derived growth factor; fibroblast growth factor such as aFGF and bFGF; epidermal growth factor; transforming growth factor (TGF) such as TGF-alpha and TFG-beta; insulin-like growth factor-I and -II; erythropoietin; osteoinductive factor; an interferon such as interferon-alpha, -beta, and -gamma; nerve growth factor (NGF), BNDF, and NT-3; colony stimulating factors (CSFs), e.g., M-CSF, GM-CSF, and G-CSF; interleukins (ILs), e.g., IL-1, IL-2, IL-3, IL-4, etc.; decay accelerating factor; atrial natriuretic peptides A, B or C; and fragments of any of the above-listed polypeptides. In addition, one or more predetermined amino acid residues in the polypeptide may be substituted, inserted, or deleted, for example, to produce products with improved biological properties, or to vary expression levels, such as adding or deleting a dibasic amino acid site susceptible to cleavage by host cell enzymes. Some of the desired polypeptides falling within this present invention may optionally possess covalent or non-covalent modifications of features of a naturally occurring molecule, for example, glycosylation modifications.

"Desired polypeptide precursor mutant" refers to a desired polypeptide precursor comprising a non-naturally occurring enzyme cleavage site as well as a desired polypeptide precursor mutant optionally having amino acid substitutions, deletions, and/or insertions at certain other positions provided that the final construct possesses the desired activity. The desired polypeptide precursor mutants of the present invention also include those mutants wherein glycosylation or other features of a naturally occurring molecule have been modified covalently or non-covalently provided that the final mutant construction possesses the desired activity.

As used herein, "polypeptide factor," refers to any protein necessary for the survival or growth of a host cell in culture. The polypeptide factor may be a hormone, growth factor, peptide hormone, autocrine factor, transport protein, oncogene/proto-oncogene and the like. Examples of polypeptide factors that are hormones are, for example, insulin, follicle stimulating hormone (FSH), calcitonin, leutinizing hormone (LH), glucagon, parathyroid hormone (PTH), thyroid stimulating hormone (TSH), thyroid releasing hormone (TRH), and growth hormone. Additional examples of polypeptide factors are the transport proteins, such as, transferrin, serum albumin, ceruloplasm, low density lipoprotein (LDL) and high density lipoprotein (HDL). Some polypeptide factors, often are described as autocrine because, in some instances, the cells they are secreted from can respond to the secreted factor; example of such factors are interleukin-2, epidermal growth factor (EGF), fibroblast growth factor (FGF); thrombin, nerve growth factor, hemopoietic growth factor and granulocyte-macrophage colony stimulating factor (GM-CSF). Yet other examples of polypeptide factors are peptides resulting from the expression of certain oncogenes/proto-oncogenes. The proteins encoded by these proto-oncogenes encompassed by the polypeptide factors of this invention are growth factors, transducing proteins and membrane receptors. Examples of a growth factor is PDGF (b subunit) encoded by the sis oncogene. Examples of peripheral membrane proteins are the truncated cell surface receptor for EGF encoded by erb-B, the cell surface receptor for M-CSF/CSF-1 encoded by fms and the receptors encoded by neu and ros. An example of a transducing protein is tyrosine kinase at the inner surface of the plasma-membrane encoded by abl. While these polypeptide factors are typically not added to a culture medium, they may be substituted for another polypeptide factor. The definition of polypeptide factor includes amino acid mutants which maintain the functional characteristics of the polypeptide factor. These mutants may comprise one or more amino acid differences in the overall sequence and may be prepared by deletions, substitutions, and/or insertions of one or more amino acids in the overall sequence. Through the use of recombinant DNA technology polypeptide factor mutants may be prepared by altering the underlying DNA. All such variations or alterations in the structure of a polypeptide factor mutant is included within the scope of this invention so long as the functional activity is maintained.

"Polypeptide factor precursor mutant" refers to a polypeptide factor precursor comprising a non-naturally occurring enzyme cleavage site.

"Polypeptide factor-depending host cell" refers to a host cell requiring one or more polypeptide factors in the culture medium for growth or survival. The polypeptide factor(s) for a particular host cell is determined using general methods known to the ordinarily skilled artisan. Elimination of the polypeptide factor from the medium may result in death of the cell or in inhibited growth.

"Heterologous polypeptide factor" is defined as a polypeptide factor not naturally occurring in the host cell.

A "heterologous" element is defined herein to mean foreign to the cell, or (unless otherwise specified) homologous to the cell but in a position within the host cell in which the element is ordinarily not found. An "endogenous" element is defined herein to mean naturally occurring in the cell. An "endogenous host cell enzyme is defined to mean an enzyme which is endogenous to the cell.

"Prohormone" refers to a hormone precursor.

"Prohormone convertase" enzymes are specialized proteinases having conserved active site domains which are substrate specific and cleave exclusively at certain sets of basic residues, preferably Lys-Arg, Arg-Arg, Lys-Lys and Arg-Lys. This type of proteinase is responsible for processing large precursor proteins, such as prorelaxin, to their biologically active form. In the present invention prohormone convertase is used to refer to mammalian PC1 and PC2, furin, and includes mammalian, yeast, or any prohormone convertase that is biologically active as described above. The yeast enzyme, Kex2, is specifically excluded from the definition of prohormone convertase enzymes. In the present invention "prohormone convertase cleavage site" refers to a cleavage site recognized by a prohormone convertase.

"Basic residue" refers to amino acids in which the R groups have a net positive charge at pH 7.0, for example: Lysine, Arginine, Histidine, "Dibasic cleavage site" contains two amino acids with basic charges on their side chains that are specifically cleaved by ]prohormone convertases, the preferred amino acids are Lys-Arg, Arg-Arg, Lys-Lys and Arg-Lys.

"Kex2" refers to a Saccharomyces yeast endoprotease which specifically processes a mating type factor and a killer factor. Kex2 contains an amino terminal catalytic domain followed by a cysteine-rich region, a transmembrane domain, and a short cytoplasmic tail.

"Furin" refers to a protein encoded by the gene fur which has homology to the Kex2 protein and is involved in processing of protein precursors. Furin is expressed constitutively in most cell types including CHO, HepG2, PC12, BHK and in most tissue. Furin mediates basic cleavages which occur in the Golgi, and has a preference for cleaving Lys-Arg residues. Like Kex2, human furin contains an amino terminal catalytic domain followed by a cysteine-rich region, a transmembrane domain, and a short cytoplasmic tail.

"Mammalian PC1 (mPC1)" refers to the sequence identified in FIG. 4, and all mammalian prohormone convertases having equal to or greater than 95% homology to the sequence in FIG. 4.

"Mammalian PC2 (mPC2)" refers to the sequence identified in FIG. 5 and all mammalian prohormone convertases having equal to or greater than 95% homology to the sequence in FIG. 5.

A "cleavage site recognizable by a host cell enzyme" refers to the cleavage site of an enzyme naturally occurring in a host cell. The preferred naturally occurring enzyme of the present invention is a prohormone convertase.

"Prohormone convertase precursor mutant" refers to a prohormone convertase precursor comprising a non-naturally occurring enzyme cleavage site as well as desired polypeptide precursor mutants optionally having substitutions, deletions, and/or insertions at certain other positions provided that the final construct possesses the desired activity.

"Precursor" means a form of the protein which may be converted into the desired protein by processing. It may be a natural pro-form or prepro-form of the protein, or a synthetic pro-form wherein a gene coding for the desired protein is preceded by a heterologous signal, or leader sequence, and such as constructs which are routinely produced in vitro.

An "isolated" polypeptide means polypeptide which has been identified and separated and/or recovered from a component of its natural environment. Contaminant components of its natural environment are materials which would interfere with diagnostic or therapeutic uses for the polypeptide, and may include proteins, hormones, and other substances. In some embodiments, the polypeptide will be purified (1) to greater than 95% by weight of protein as determined by the Lowry method, and most preferably more than 99% by weight, (2) to a degree sufficient to obtain at least 15 residues of N-Terminal or internal amino acid sequence by use of a spinning cup sequenator, or (3) to homogeneity by SDS-PAGE using Coomassie blue or, preferably, silver stain. This definition specifically includes polypeptides present in situ in a host cell wherein the host cell in its native form lacks the polypeptide. Ordinarily, however, isolated polypeptide will be prepared by at least one purification step. In preferred embodiments, isolated prohormone convertase is utilized.

"Nucleic acid" refers to a nucleotide sequence comprising a series of nucleic acids in a 5' to 3' phosphate diester linkage that may be either an RNA or a DNA sequence. If DNA, the nucleotide sequence is either single or double stranded. Polypeptide-encoding nucleic acid is RNA or DNA that encodes a biologically or antigenically active polypeptide, is complementary to nucleic acid sequence encoding such polypeptide, or hybridizes to nucleic acid sequence encoding such polypeptide and remains stably bound to it under stringent conditions.

Nucleic acid encoding a prohormone convertase and/or desired protein is introduced into a host animal cell or cells, tissue, organ, organism, or pathological lesion, for the purpose of modulating gene expression and/or function of the gene product, i.e. for the purpose of gene therapy. For example, Nucleic acid encoding prohormone convertase(s) and/or desired protein may be introduced into animal germ cell lines as well as animal somatic cell lines.

Nucleic acid introduced into the host animal may or may not be methylated. The selection of a suitable technique for methylation of nucleic acid is deemed to be within the scope of those skilled in the art (Kessler et al., *Gene* vol. 92 pg. 1–248 [1990]) and (Doefler, *Biol Chem Hoppe Seyler* vol. 3721 no. 8. pg. 557–564 [1991]).

"Isolated" polypeptide nucleic acid is a nucleic acid that is identified and separated from at least one contaminant nucleic acid with which it is ordinarily associated in the natural source of the nuclic acid. Isolated nucleic acid is other than in the form or setting in which it is found in nature. Isolated prohormone convertase nucleic acid therefore distinguishes prohormone convertase nucleic acid as its exists in natural cells. However, isolated prohormone convertase nucleic acid includes prohormone convertase in ordinarily prohormone convertase-expressing cells where the nucleic acid is, for example, in a chromosomal location different from that of natural cells.

"Hydrophobic transmembrane anchor" is the hydrophobic region of enzymes localized in the golgi, RER or other cellular membranes which facilitates localization of the enzyme in that region and reduces the loss of enzyme from the cell, specifically illustrating such anchors are the kex2 and furin transmembrane anchors.

The term "mutant" as used herein is defined as a molecule in which the amino acid sequence, glycosylation, or other feature of a naturally occurring molecule has been modified covalently or noncovalently and is intended to include variants. Some of the variants falling within this invention possess amino acid substitutions or additions of a host cell enzyme cleavage sites and optionally also substitutions, deletions, and/or insertions at certain other positions provided that the final construct possesses the desired activity.

The term "host cell" refers to those cells capable of growth in culture and capable of expressing a prohormone convertase, and/or a desired protein and/or a polypeptide factor(s). The host cells referred to in this disclosure encompass cells in in vitro culture as well as cells that are within a host animal. While the preferred host cells in in vitro culture of this invention are mammalian cells, other cells may be used. Some of the embodiments of this invention involve the use of a host cell enzyme which itself requires processing from a precursor to an active form; for those host cells, such as bacterial or yeast, that lack the enzyme required to process the host cell enzyme, such enzyme may be introduced into the host cell to facilitate practice of the methods of this invention.

Host cells that are within an animal refer to those host cells which have been introduced into an animal or are endogenous to that animal, and are capable of expressing a prohormone convertase, and/or a desired protein.

In the present invention, the cells used for introduction of nucleic acid encoding proteins of interest into the host animal may be host autologous cells, i.e. those derived from the host animal, or non-host autologous cells, not derived from the host animal. In certain embodiments of this invention, the cells used for introduction of the nuclic acid into the animal are non-host autologous, and the non-host autologous cells are preferably non-immunogenic and non-toxic to the host animal.

In the present invention a host cell is provided comprised of nucleic acid encoding variant proinsulin that is capable of secreting insulin in response to glucose. Any host cell showing hypersensitivity to glucose may be expressing high levels of hexokinase activity and these cells will need to be modified by recombinant nucleic acid techniques to remove or reduce the hexokinase activity as described in WO 92/21756, published Dec. 10, 1992. Such monitoring and modification of hexokinase activity is routine within the field to which this invention pertains.

The host cell of the present invention may be comprised of nucleic acid encoding polypeptide precursor variants having prohormone convertase cleavage sites for processing by naturally occurring or non-naturally occurring host cell processing enzymes.

As used herein, the term "engineered" cell is intended to refer to a cell into which a desired nucleic acid, such as a nucleic acid encoding a variant proinsulin, has been introduced. Engineered cells are distinguished from naturally occurring cells which do not contain introduced nucleic acid. Nucleic acid of the present invention includes nucleic acid obtained from a natural source, chemically synthesized, or produced by techniques of recombinant technology. Engineered cells encoding recombinant proteins of the present invention will be derived from cells lacking the ability to form secretory granules. Illustrative of cell types lacking the ability to form secretory granules and possessing constitutive protein secretory pathway are fibroblasts, macrophages, epithelial cells, and lymphocytes.

Techniques available to introduce nuclic acid into animal host cells include: infection of the host cell with a virus, such as a replication defective virus, in particular a retroviral vector, comprised of nucleic acid encoding the protein of interest (for example see WO91/12329 published August 22, 1991); the use of direct injection techniques wherein the nucleic acid, in the form of cDNA or genomic DNA, may be associated with liposomes or liposome complexes and directly injected into the animal host cell (Felgner et al. *Nature* vol. 349 pg. 351–352 [1991])); stable integration of the introduced nucleic acid into the host animal genome through homologous recombination techniques (Waldman, *Crit Rev Oncol/Hemat* vol. 12, pg 49–64 [1992]); and introduction of nucleic acid into the host animal cell through electroporation (Reid et al., *Guide to Electroporation and Electrofusion,* Chang et al., editor, Academic Press, pub. pg 209–225 [1992]) and (Chang, et al., *Biochimica et Biophysica Acta,* vol. 1092, no. 2 pg. 153–169 [1991]).

Representative examples of suitable viruses that can be modified to modulate gene expression and/or function of the gene product include: Harvey Sarcoma virus; Rous Sarcoma virus, MPSV, Moloney murine leukemia virus, and nucleic acid viruses, such as adenovirus. In employing the suitable viral vector, steps should be taken to eliminate and/or minimize the chances for replication of the virus. Various techniques are know in the art for providing helper cells that produce viral vector particles that are essentially free of replicating virus. A replication defective virus is one which lacks one or more of the replication genes, gag (group-specific antigen), pol (polymerase), or env (envelope) protein encoding genes. (Markowitz, et al., *Journal of Virology,* vol. 62., no. 4, pgs. 1120–1124 [1988]; Watanabe, et al., *Molecular and Cellular Biology,* vol. 3, nol. 12, pgs. 2241–2249 [1983] Danos et al., *PNAS* vol. 85, pgs. 6460–6464 [1988] and Bosselman, et al. *Molecular and Cellular Biology* vol. 7, no. 5 pgs. 1797–1806 [1987]).

The selection of a suitable technique for introduction of nucleic acid into host cells is deemed to be routine for those ordinarily skilled in the art from the teachings herein.

Selection of host or engineered cells producing proteins of interest is through means deemed to be within the scope of those skilled in the art and includes for example, use of marker genes, such as antibiotics, detection of introduced nucleic acid through methods of recombinant technology (Sanbrook, et al., *Molecular Cloning—A Laboratory Manual,* 2nd. publisher, Cold Spring Harbor: Cold Spring Harbor Laboratory Press [1988]); use of antibiotics to detect production of desired proteins (Sanbrook et al., Supra); and the testing of engineering cells comprised of nucleic acid encoding proteins of interest in animal model systems (Barr et al., *Science* vol. 254, pg. 1507–1509 [1991]).

The host cell of the present invention is preferrably one that lacks the ability to form secretory granules and has a constitutive pathway of protein secretion. In the practice of the present invention, the selected host cell may comprise nucleic acid encoding a facilitative glucose transporter (GLUT) and glucokinase naturally occurring in the host cell or non-naturally occurring in the host cell, i.e. introduced into the cell through recombinant techniques known in the art. The host cell of the present invention will possess the ability to express a prohormone convertase and/or a desired protein. In the practice of the present invention, nucleic acid encoding the prohormone converase may be naturally occurring in the cell or it may be non-naturally occurring, i.e. introduced into the cell through techniques known in the art.

The expressions "cell," and "cell culture" are used interchangeably and all such designations include progeny and ancestors. It is also understood that all progeny may not be precisely identical in DNA content, due to deliberate or inadvertent mutations. Mutant progeny that have the same function or biological activity as screened for in the cell are included. Where distinct designations are intended, it will be clear from the context.

"Transfection" refers to the taking up of an expression vector by a host cell whether or not any coding sequences are in fact expressed. Numerous methods of transfection are known to the ordinary skilled artisan for example, $CaPO_4$ and electroporation. Successful transfection is generally recognized when any indication of the operation of this vector occurs within the host cell.

"Transformation" means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., *Gene,* 23: 315 (1983) and WO 89/05859 published Jun. 29, 1989. For mammalian cells without such cell walls, the calcium phosphate precipitation method described in sections 16.30–16.37 of Sambrook et al, supra, is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.,* 130: 946 (1977) and Hsiao et al., *Proc. Natl. Acad. Sci. (USA),* 76: 3829 (1979). However, other methods for introducing DNA into cells such as by nuclear injection, electroporation, or by protoplast fusion may also be used.

"Stably transformed host cell" refers to a cell wherein the inserted nucleic acid is present either integrated in the host cell or extrachromosomally, and wherein the inserted nucleic acid is continuously produced by the cell for about two weeks after insertion of nucleic acid. General aspects of mammalian cell host system transformations have been described by Axel in U.S. Pat. No. 4,399,216 issued Aug. 16, 1983.

The term "medium" refers to the aqueous environment in which the mammalian cells are grown in culture. The medium comprises the physiochemical, nutritional, and hormonal environment. Traditionally the medium has been formulated by the addition of nutritional and growth factors necessary for growth or survival. "Serum-free medium" refers to a medium lacking serum. The hormones, growth factors, transport proteins, peptide hormones and the like typically found in serum which are necessary for the survival or growth of particular cells in culture are typically added as a supplement to serum-free medium. A "defined medium" refers to a medium comprising nutritional and hormonal requirements necessary for the survival and growth of the cells in culture such that the components of the medium are known. A defined medium provided by the method of the instant invention establishes a local environment for a particular host cell that may differ from the general environment of the medium. Cells in serum-free medium generally require insulin and transferrin for optimal growth. These two factors should be tested first when determining what factors a given cell requires. Most cell lines require one or more of the growth factors. These include epidermal growth factor (EGF), fibroblast growth factor (FGF), insulin-like growth factors I and II (IGF-I, IGF-II), nerve growth factor (NGF), etc. Other classes of factors which may be necessary include: transport and binding proteins (e.g., ceruloplasmin, high and low density lipoprotein [HDL, LDL], albumin); and hormones.

"Stringent conditions" are those hybridization conditions that (1) employ low ionic strength and high temperature for washing, for example, 0.015 N NaCl/0.0015 M sodium citrate/0/1% $NaDodSo_4$ at 50° C.; (2) employ during hybridization a denaturing agent such as formamide, for example, 50% (vol/vol) formamide with 0.1% bovine serum albumin/0/1% Ficoll/0/1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS, and 10% dextran sulfate at 42 C, with washes at 42 C in 0.2 x SSC and 0.1% SDS.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., *Nucleic Acids Res.,* 9: 6103–6114 (1981),and Goeddel et al., *Nucleic Acids Res.,* 8: 4057 (1980).

"Polymerase chain reaction," or "PCR," as used herein generally refers to a procedure wherein minute amounts of a specific piece of nucleic acid, RNA and/or DNA, are amplified as described in U.S. Pat. No. 4,683,195 issued Jul. 28, 1987. Generally, sequence information from the ends of the region of interest or beyond needs to be available, such that oligennucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant, Biol.,* 51: 263 (1987); Erlich, ed., *PCR Technology,* (Stockton Press, N.Y. 1989). As used herein, PCR is considered to be one, but not the only, example of a nucleic acid polymerase reaction method for amplifying a nucleic acid test sample, comprising the use of a known nucleic acid as a primer and utilizing a nucleic acid polymerase to amplify or generate a specific piece of nucleic acid.

"Oligonucleotide-mediated mutagenesis" refers to a method for preparing substitution, deletion, and insertion mutants of prohormone convertase 1 or 2 encoding DNA. This technique is well known in the art as described by Adelman et al., *DNA,* 2: 183 (1983). Briefly, the prohormone convertase 1 or 2 DNA is altered by hybridizing an oligonucleotide encoding the desired mutation to a DNA template, where the template is the single-stranded form of a plasmid or bacteriophage containing the unaltered or native DNA sequence of the prohormone convertase 1 or 2. After hybridization, a DNA polymerase is used to synthesize an entire second complementary strand of the template that will thus incorporate the oligonucleotide primer, and will code for one selected alteration in the prohormone convertase 1 or 2. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., (Proc. Natl. Acad. Sci. USA, 75: 5785 [1978]).

"Glycosylation" refers to the post-translational modification process of adding a series of sugar residues to proteins to produce glycoproteins. Glycosylation can occur in the cryosol, the endoplasmic reticulum, or the Golgi apparatus of mammalian cells.

"pRK5" and "pRK7" are expression vectors used to transform mammalian cells. The construction of expression vector pRK5 was described in European Patent Application 0307247A2, published Mar. 15, 1989. The pRK7 vector was described in European Patent Application 278,776 published Aug. 17, 1988.

"Regulated protein secretory pathway" refers to the cellular pathway for exocytosis which is regulated over short periods of time by physiological stimuli, such as cyclic AMP. This pathway is not required for cell viability and is only present in specialized secretory cells such as endocrine and exocrine cells.

"Constitutive protein secretory pathway" refers to the unregulated cellular pathway which is found in cells such as macrophages and fibroblasts.

"Human insulin" refers to a protein exhibiting a biological activity in common with naturally occurring human insulin. Human insulin biological activity includes promoting glucose utilization, protein synthesis, and the formation and storage of neutral lipids. "Human proinsulin" is defined to be a molecule containing the B, C and A chain amino acid sequence and includes amino acid variants that maintain the functional characteristics of insulin discussed above. These variants may comprise one or more amino acid differences in the overall sequence and may be prepared by deletions, substitutions, and/or insertions of one or more amino acids in the overall sequence. Through the use of techniques common in the field, human proinsulin mutants may be prepared by altering the protein itself or the nucleic acid encoding the protein. All such variations or alterations in the structure of human proinsulin resulting in human proinsulin variants are included within the scope of this invention so long as the functional activity of proinsulin is maintained.

"Human relaxin" denotes a functional protein capable of exhibiting a biological activity. Human relaxin biological activity is defined as any of 1) immunological cross-reactivity with at least one epitope of human relaxin or 2) the possession of a least one hormonal function in common with human relaxin. "Human prorelaxin" is defined to be a molecule containing the B, C, and A chain amino acid sequence and includes amino acid variants which maintain the functional characteristics discussed above. These variants may comprise one or more amino acid differences in the overall sequence and may be prepared by deletions, substitutions, and/or insertions of one or more amino acids in the overall sequence. Through the use of recombinant DNA technology human prorelaxin mutants may be prepared by altering the underlying DNA. All such variations or alterations in the structure of human prorelaxin resulting in human prorelaxin variants are included within the scope of this invention so long as the functional activity is maintained.

As used herein, "IGF-I" refers to IGF-I from any species, including bovine, ovine, porcine, equine, and preferably human, in naturally occurring-sequence or in variant form, or from any source, whether natural, synthetic, or recombinant. Variants may comprise one or more amino acid differences in the overall sequence and may be prepared by deletions, substitutions, and/or insertions of one or more amino acids in the overall sequence. All such variations or alterations in the structure of IFG-I resulting in human prorelaxin variants are included within the scope of this invention so long as the functional activity is maintained.

An insulin responsive disorder is defined as being any disorder characterized by symptoms which can prevented or treated by treatment with insulin alone or insulin in combination with other therapeutics.

The nucleic acid sequences encoding the variant proinsulin cell processing enzymes, desired polypeptides and the other genes of interest of this invention are desirably incorporated into a host cell in more than one copy. Nucleic acid is introduced at levels of approximately 5 to 10 $\mu$g DNA/cell. Although this amount of nucleic acid may be boosted, for example by 10 or 20 times the above amount, or by any amount sufficient to yield the desired result.

This invention also encompasses the introduction of nucleic acid into a cell or tissue of an animal either in vitro, in vivo or ex vivo. In some instances, the nucleic acid is intended to replace (or act in place of) a functionally deficient endogenous gene or to confer on the host the ability to produce a therapeutic polypeptide such as insulin. Methods for introducing nucleic acid into such or tissues include methods for in vitro introduction of nucleic acid such as the insertion of naked DNA or RNA (such as by injection of the nucleic acid into a tissue), the reintroduction into a tissue of a cell modified ex vivo to transcribe and express heterologous or variant nucleic acid, the provision of nucleic acid in liposomes or other carrier, the use of a vector such as a virus, retrovirus, phage, plasmid etc., or techniques such as elecytoporation. Methods of electroporation in vitro are disclosed in Barsoum, DNA and *Cells Biology*, 9 (4):293–300 (1990). Electroporation may be used in vivo, for example by injecting the desired nuclear acid into a tissue and then applying current—by electrodes or other suitable equipment—to the target tissue. Other known methods for the introduction of nucleic acid into cells or tissues are suitable for the practice of this invention.

Transgenic animals which transcribe and express heterologous nucleic acid are encompassed by this invention. Such animals have produced by transfecting germ cells, somatic cells, or embryos with heterologous nucleic acid according to the methods of this invention, including using endogenous sequences for homologous recombination and introduction of heterologous sequences. The modified cells/embryos are suitably implanted and allowed to mature into or stably integrate into adult animals containing the heterologous DNA. A reproducible percentage of such animals transcribe and express the heterologous nucleic acid as protein which can be identified in tissues including blood or serum. Methods for making transgenic animals are described in U.S. Pat. No. 4,396,601.

The formulation and mode of administration for in vitro use will be determined by the experimental criteria as described above. Aqueous formulations that are compatible with the culture or perfusion medium will normally be used.

Nucleic acid for introduction to tissues or cells in vivo or ex vivo, and modified cells/tissue for parenteral administration may be formulated in a unit dosage injectable form (solution, suspension, emulsion) in association with a pharmaceutically acceptable parenteral carrier. Such carriers are inherently nontoxic, and non-therapeutic. Examples of such carriers are water, saline, Ringer's solution, dextrose solution, and 5% human serum albumin. Nonaqueous carriers such as fixed oils and ethyl oleate can also be used. Liposomes may be used as carriers. The carrier may contain minor amounts of additives such as substances that enhance isotonicity and chemical stability, e.g., buffers and preservatives.

The cells or tissues of this invention used in therapy are formulated and dosages established in a fashion consistent with good medical practice taking into account the disorder to be treated, the condition of the individual patient, the site of delivery of the cell or tissue, the method of administration and other factors known to practitioners. The cells or tissues are prepared for administration as described above.

A therapeutically effective amount of an engineered host cell or a plasmid producing a recombinant product is that amount of host cell or plasmid that is effective to prevent or treat symptoms of a disorder or responsive pathologic physiological condition. In certain embodiments of the present invention, the disorder may be an insulin responsive disorder treated or prevented through introduction of nucleic acid encoding a recombinant proinsulin into the host animal.

The amount of host cells administered to a subject will depend on the level of production of the desired proteins. In preferred embodiments, $1 \times 10^6$ to $1 \times 10^{10}$ cells will be administered daily, with each cell secreting preferably from 500 to 5000 ng per 106 cells per day of the desired protein.

The therapeutic amount of a plasmid producing a recombinant product of interest for administration to a subject will depend on levels of expression of the recombinant product by the plasmid. For most purposes, the range of plasmid DNA will be 1 mg to 1 mg of plasmid DNA with expression levels being in the range of 500 ng of recombinant product per 1 μg of DNA encoding recombinant product.

The route of administration of host cells or plasmids comprised of DNA encoding recombinant proteins of the present invention is illustrated by teachings herein and includes: viral infection with a suitable virus, retrovirus phage, etc., direct injection into a target cell or tissue of the host cell or plasmid of this invention in a suitable carrier as described in Wang et al., *PNAS* USA vol. 84, pg. 7851–7855 [1987], Kaneda, et al., *Science* vol. 243, pg. 375–378 [1989]. and Ono et al., *Neurosci Lett.* vol. 117, pg. 259–263 [1990]; implantation (typically intraperitoneally or subcutaneously) of engineered cells, as described in WO 92/21756, published Dec. 19, 1992; through homologous recombination as described in Waldman et al., supra; and through electroporation as described in Reid et al., supra or Barsoum, *DNA and Cell Biology* 9 (4):293–300 (1990).

Use of Prohormone Convertase in Mammalian Cell Culture

In the present invention, the host cells expressing a prohormone convertase may be used to express polypeptide factors needed for cell growth and anabolism.

Mammalian cells frequently require one or more hormones from each of the following groups: steroids, prostaglandins, growth factors, pituitary hormones, and polypeptide hormones. Most cell types require insulin to survive in serum-free media. (Sato, G. H. et al., in Growth of Cells in Hormonally Defined Media, [Cold Spring Harbor Press, N.Y., 1982]). In addition to the hormones, cells may require transport proteins such as transferrin (plasma iron transport protein), ceruloplasmin (a copper transport protein), and high density lipoprotein (a lipid carrier) to be added to cell media. The set of optimal hormones or transports proteins will vary for each cell type. Most of those hormones or transport proteins have been added exogenously or, in a rare case, a mutant cell line has been found which does not requires a particular factor.

Cellular proliferation has been studied to elaborate the events necessary to lead from quiescent growth arrest to the cellular commitment to proliferate. Various polypeptide factors have been found to be involved in that transformation. These transformed cells have been found to produce peptide growth factors in culture. (Kaplan, P. L. et al., PNAS 79:485–489 [1982]). The secretion from a cell of a factor to which that same cell can respond has been referred to as an "autocrine" system. Numerous factors have been described as autocrine: bombesin, interleukin-2 (Duprez, V. et al., PNAS 82:6932 [1985]); insulin, (Serrero, G. In Vitro Cellular & Dev. Biol. 21[9]:537 [1989]); transforming growth factor alpha (TGF-a), platelet-derived growth factor (PDGF); transforming growth factor-beta (TGF-b), (Sporn, M. B. & Roberts, A. B., Nature 313:745 [1985]); sarcoma growth factor (SGF), (Anzano, M. A. et al., PNAS 80:6264 [1983]); and, hemopoietic growth factor, granulocyte-macrophage colony stimulating factor (GM-CSF), (Lang, R. A. et al., Cell 43:531 [1985]). The methods of the present invention are suitable for cells expressing one or more prohormone convertases and further comprising nucleic acid encoding a polypeptide factor required for proliferation or for maintenance of cellular integrity. In the present invention the preferred polypeptide factor is insulin.

In the present invention, the host cells expressing a prohormone convertase may be used to express any desired polypeptide which requires processing from a precursor form. The cells of the present invention may be used in cell culture to produce any polypeptide of interest even those not requiring processing by a prohormone convertase.

In the present invention nucleic acid encoding a prohormone convertase may be introduced prior to the introduction of nucleic acid encoding a desired polypeptide or a polypeptide factor. In the present invention, nucleic acid encoding a prohormone convertase may be introduced simultaneously with nucleic acid encoding a desired polypeptide or a polypeptide factor wherein the nucleic acid may be on the same or separate vectors.

As described more fully herein, the present invention describes a method for the production of a heterologous polypeptide factor in a polypeptide factor-dependent host cell comprising a) introducing into the polypeptide factor-dependent host cell nucleic acid encoding a heterologous polypeptide factor precursor comprising a cleavage site recognizable by a host cell enzyme and wherein said host cell is dependent on the cleavage product of said polypeptide factor precursor; and b) culturing said host cell under conditions wherein the polypeptide factor precursor is cleaved at said cleavage site by the host cell enzyme, thereby producing said polypeptide factor. Optionally polypeptide factor is recovered.

The present invention further describes a method for the production of a desired polypeptide in a host cell expressing a prohormone convertase comprising a) introducing into the host cell expressing said prohormone convertase nucleic acid encoding a desired polypeptide; and b) culturing said host cell under conditions wherein said desired polypeptide is expressed. Optionally the desired polypeptide is recovered.

For any of the cleavage events described herein, additional host cell enzyme or heterologous enzyme is added to the host cell as desired.

The present invention discloses nucleic acid encoding a polypeptide factor precursor mutant comprising an prohormone convertase cleavage site. Another aspect of the present invention is a nucleic acid encoding a prohormone convertase that is joined to nucleic acid encoding a hydrophobic transmembrane anchor. This joined nucleic acid directs the synthesis of a polypeptide fusion product wherein the catalytically active prohormone convertase is covalently attached to a hydrophobic transmembrane anchor. Among the preferred hydrophobic transmembrane anchors are the KEX2 hydrophobic transmembrane anchor and the furin hydrophobic transmembrane anchor.

The present invention also provides for a prohormone convertase precursor mutant having nucleic acid encoding a prohormone convertease cleavage site.

The present invention further provides for host cells having nucleic acid encoding a polypeptide factor precursor mutant comprising a prohormone convertase cleavage site.

The nucleic acid and methods disclosed herein are suitable for use for expression in a wide range of host cell lines. Mammalian cells are the preferred host cell for expressing prohormone convertases. The host cell of the present invention may be a mammalian cell that does not normally express detectable amounts of prohormone convertase. In addition, the mammalian cell of the present invention may be a mammalian cell that produces levels of prohormone convertase that are insufficient to process the desired polypeptide precursor to desired polypeptide. Transformation of such cells by nucleic acid encoding a prohormone convertase results in an increase in prohormone convertase sufficient to process desired polypeptide precursor to polypeptide.

Isolation of Nucleic Acid

The nucleic acid encoding the prohormone, convertase, or other polypeptide of interest may be obtained from any cDNA library prepared from tissue or cells believed to possess the polypeptide mRNA and to express it at a detectable level. The desired gene may also be obtained from a genomic library.

Libraries are screened with probes designed to identify the gene of interest or the protein encoded by it. For cDNA expression libraries, suitable probes include monoclonal or polyclonal antibodies that recognize and specifically bind to the desired polypeptide; oligonucleotides of about 20–80 bases in length that encode known or suspected portions of the polypeptide of interest's cDNA from the same or different species; and/or complementary or homologous cDNAs or fragments thereof that encode the same or a similar gene. Appropriate probes for screening genomic DNA libraries include, but are not limited to, oligonucleotides; cDNAs or fragments thereof that encode the same or a similar gene; and/or homologous genomic DNAs or fragments thereof. Screening the cDNA or genomic library with the selected probe may be conducted using standard procedures as described in chapters 1014 12 of Sambrook et al., supra.

An alternative means to isolate the gene encoding the polypeptide of interest is to use polymerase chain reaction (PRC) methodology as described in section 14 of Sambrook et al., supra. This method requires the use of oligonucleotide probes that will hybridize to the gene of interest. Strategies for selection of oligonucleotides are described below.

Another alternative method for obtaining the gene of interest is to chemically synthesize it using one of the methods described in Engels et al. (Agnew. Chem. Int. Ed. Engl., 28: 716–734 [1989]). These methods include triester, phosphite, phosphoramidite and H-Phosphonate methods. PCR and other autoprimer methods, and olignoucleotide syntheses on solid supports. These methods may be used if the entire nucleic acid sequence of the gene is known, or the sequence of the nucleic acid complementary to the coding strand is available, or alternatively, if the target amino acid sequence is known, one may infer potential nucleic acid sequences using known and preferred coding residues for each amino acid residue.

A preferred method of practicing this invention is to use carefully selected oligonucleotide sequences to screen cDNA libraries from various tissues, depending on the source of the gene or polypeptide of interest.

The oligonucleotide sequences selected as probes should be of sufficient length and sufficiently unambiguous that false positives are minimized. The actual nucleotide sequence(s) is usually based on conserved or highly homologous nucleotide sequences or regions of other polypeptides homologous to the polypeptide of interest. The oligonucleotides may be degenerate at one or more positions. The use of degenerate oligonucleotides may be of particular importance where a library is screened from a species in which preferential codon usage in that species is not known. The oligonucleotide must be labeled such that it can be detected upon hybridization to DNA in the library being screened. The preferred method of labelling is to use 32-P labeled ATP with polynucleotide kinase, as is well known in the art, to radiolabel the oligonucleotide. However, other methods may be used to label the oligonucleotide, including, but not limited to, biotinylation or enzyme labeling.

Of particular interest is prohormone convertase nucleic acid that encodes a full-length polypeptide. In some preferred embodiments, the nucleic acid sequence includes the prohormone convertase signal sequence. Nucleic acid having all the protein coding sequence is obtained by screening selected cDNA or genomic libraries, and, if necessary, using conventional primer extension procedures as described in section 7.79 of Sambrook et al., supra, to detect precursors and processing intermediates of mRNA that may not have been reverse-transcribed into cDNA.

In preferred embodiments of this invention DNA hybridization probes are used to identify noval prohormone convertase candidate enzyme message in cell lines containing regulated secretary pathways. The murine pituitary tumor cell line AtT-20 is suitable because it is neuroendocrine-derived, and secretes ACTH. It would therefore be expected to contain processing enzymes involved in the conversion of the prohormone proopiomelanocortin (POMC) precursor to mature ACTH, a process which requires cleavage at specific pairs of basic amino acids in the prohormone substrate.

Candidate cDNAs expressed in the AtT-20 cells may be amplified by the MOPAC precedure (Innis 1990) using degenerate primer sequences based on those of Smeekens and Steiner (1990). In particularly preferred embodiments, two PC-like cDNAs are amplified and cloned from the AtT-20 cells; mPC2 (greater than 95% homologous to the human PC2 of Smeekens and Steiner) and second sequence similar to mPC2, termed mPC1.

Construction of polypeptide mutants

Amino acid sequence variants of the prohormone convertase, polypeptide factor, desired polypeptide or other polypeptide of interest are prepared by introducing appropriate nucleotide changes into the encoding DNA, or by in vitro synthesis of the desired polypeptide. Such variants include, for example, delations from, or insertions or substitutions of, residues within the amino acid sequence for the polypeptide of interest. Any combination of deletion, insertion, and substitution can be made to arrive at the final construct, provided that the final construct possesses the desired characteristics. The amino acid changes also may alter post-translational processes of the polypeptide, such as changing the number or position of glycosylation sites, altering the membrane anchoring characteristics, and/or altering the intra-cellular location of the polypeptide by inserting, deleting, or otherwise affecting the leader sequence of the naturally occurring polypeptide of interest.

In designing amino acid sequence polypeptide variants, the location of the mutation site and the nature of the mutation will method of labeling is to use 32-P labeled ATP with polynucleotide kinase, as is well known in the art, to radiolabel the oligonucleotide. However, other methods may be used to label the oligonucleotide, including, but not limited to, biotinylation or enzyme labeling, substituting first with conservative amino acid choices and then with more radical selections depending upon the results achieved, (2) deleting the target residue, or (3) inserting residues of the same or a different class adjacent to the located site, or combinations of options 1–3.

There are two principal variables in the construction of amino acid sequence variants: the location of the mutation site and the nature of the mutation. In general, the location and nature of the mutation chosen will depend upon the characteristic to be modified.

Amino acid sequence deletions generally range from about 1 to 30 residues, more preferably about 1 to 10 residues, and typically are contiguous. Deletions may be introduced into regions of low homology between the polypeptide of interest and other polypeptides to modify the activity of the polypeptide of interest. Deletions from the polypeptide of interest in areas of substantial homology with any other polypeptide will be more likely to modify the biological activity of the polypeptide of interest more significantly. The number of consecutive deletions will be selected so as to preserve the tertiary structure of polypeptide of interest in the affected domain, e.g., beta-pleated sheet or alpha helix.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the sequence of the polypeptide of interest) may range generally from about 1 to 10 residues, more preferably 1 to 5, most preferably 1 to 3. An example of a terminal insertion is an N-terminal methionyl residue, an artifact of the direct expression of a polypeptide in bacterial recombinant cell culture.

Other insertional variants of the polypeptide of interest include the fusion to the N- or C-terminus of the polypeptide of immunogenic polypeptides, e.g., bacterial polypeptides such as beta-lactamase or an enzyme encoded by the *E. coli* trp locus, or yeast protein, and C-terminal fusions with proteins having a long half-life such as immunoglobulin constant regions (or other immunoglobulin regions), albumin, or ferritin, as described in WO 89/02922 published Apr. 6, 1989.

Another group of variants are amino acid substitution variants. These variants have at least one amino acid residue in the polypeptide of interest removed and a different residue inserted in its place. The sites of greatest interest for substitutional mutagenesis include sites identified as the active site(s) of the polypeptide of interest, and sites where the amino acids found in homologous polypeptides from various species are substantially different in terms of side-chain bulk, charge, and/or hydrophobicity.

DNA encoding amino acid sequence variants of the beta-8 integrin subunit is prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the beta-8 integrin subunit. These techniques may utilized beta-8 integrin subunit nucleic acid (DNA or RNA), or nucleic acid complementary to the beta-8 integrin subunit nucleic acid. In the present invention, the site-directed mutagenesis method of Kunkel, *Methods of Enzymology* 154:367–383, 1987 are particularly preferred.

Another method for preparing the prohormone convertase mutants of this invention are preferably constructed by mutating the nucleic acid sequences that encode of the native prohormone convertase. Generally, particular regions or sites of the nucleic acid will be targeted for mutagenesis, and thus the general methodology employed to accomplish this is termed site-directed mutagenesis. In the present invention the preferred method of site-directed mutagenesis is by the method of Kunkel (*Methods of Enzymology* 154:367–382, 1987).

Another method for preparing mutants of this invention is by oligo-mediated mutagenesis. Oligonucleotide-mediated mutagenesis is a preferred method for preparing substitution, deletion, and insertion mutants of prohormone convertase 1 or 2 encoding DNA. This technique is well known in the art as described by Adelman et al., *DNA*, 2: 183 (1983). Briefly, the prohormone convertase 1 or 2 DNA is altered by hybridizing an oligonucleotide encoding the desired mutation to a DNA template, where the template is the single-stranded form of a plasmid or bacteriophage containing the unaltered or naturally occurring DNA sequence of the prohormone convertease 1 or 2. After hybridization, a DNA polymerase is used to synthesize an entire second complementary strand of the template that will thus incorporate the oligonucleotide primer, and will code for the selected alteration in the prohormone convertase 1 or 2.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA*, 75: 5765 [1978]).

PCR mutagenesis is also suitable for making amino acid mutants. While the following discussion herein may refer to DNA, it is understood that the technique also finds application with RNA. The PCR technique refers to the procedure outlined in *Genetic Engineering* Vol 12 pp 115–137, [1990] by Arnheim; *Analytical Chemistry*, vol 62 pp 1202–1214 [1990] by Gibbs; and *Science* vol 252 pp. 1643–1651 [1991] by Gelfand.

Mutants Affecting Polpeptide precursor processing

One aspect of the present invention is a polypeptide factor precursor mutant containing modification within the nucleic acid encoding pre-pro or pro sequence which optimizes the precursor processing by the prohormone convertase. Cells vary widely in their processing capability, and consequently, in the prohormone maturation products that are ultimately secreted from them. This difference in processing of polypeptide factor precursor mutants could be the result of several factors: (a) the precursor sequence itself could influence the accessibility of the prohormone convertase to the cleavage site, (b) each specific pattern could represent a distinctly different processing enzyme, (c) there could be a limited number of prohormone convertases that exhibit specificity due to their location (microenvironment) or relative abundance within the cell, (d) similar precursors could be modified in the various cell types influencing their accessibility to the prohormone convertase.

In the present invention, one preferred polypeptide factor precursor mutant is a human proinsulin mutant having a prohormone convertase cleavage site wherein the cleavage site is processed in the constitutive pathway of the host cell. The preferred proinsulin variant is one comprising a residue substitution for naturally occurring residues in the Type I and/or Type III cleavage sites as outlined.

Proinsulin residue Lys 29 is substituted with any of a residue selected from the group of Arg, His, Cys, Met, Phe, Tyr, Trp, Pro, Gly, Ala, Val, Ile, Leu, Ser. Thr, Asp, Glu, Gln, Asn, and most preferably Arg.

Proinsulin residue Arg 31 is substituted with any of a residue selected from the group of Lys, His, Cys, Met, Phe, Tyr, Trp, Pro, Gly, Ala, Val, Ile, Leu, Ser, Thr, Asp. Glu, Gln, Asn, and most preferably Lys.

Proinsulin residue Leu 62 is substituted with any of a residue selected from the group of Arg, His, Cys, Met, Phe, Tyr, Trp, Pro, Gly, Ala, Val, Ile, Lys, Ser, Thr, Asp, Glu, Gln, Asn, and most preferably Lys or Arg.

Site-directed mutagenesis by the method of Kunkel (Kunkel 1987) is a preferred method for preparing substitution, deletion, and insertion variants of polypeptide precursors.

A preferred mammalian prophormone convertase 1 (mPC1) precursor mutant comprises a residue substitution for naturally occurring residues in the prohormone convertase cleavage site of the precursor as outlined: mRC1 precursor residue Lys 80 is substituted with any of a residue selected from the group Arg, His, Cys, Met, Phe, Tyr, Trp, Pro, Gly, Ala, Val, Ile, Leu, Ser. Thr, Asp, Glu, Gln, Asn, and most preferably Arg.

A preferred mammalian prohormone convertase 2 (mPC2) precursor mutant comprises a residue substitution for naturally occurring residues in the prohormone convertase cleavage site of the precursor as outlined. mPC2 precursor residue Lys 77 is substituted with any of a residue selected from the group Arg, His, Cys, Met, Phe, Tyr, Trp, Pro, Gly, Ala, Val, Ile, Leu, Ser, Thr, Asp, Glu, Gln, Asn, and most preferably Arg. mPC2 precursor residue Arg 78 is substituted with any of a residue selected from the group Lys, His, Cys, Met, Phe, Tyr, Trp, Pro, Gly, Ala, Val, Ile, Leu, Ser, Thr, Asp, Glu, Gln, Asn, and most preferably Ala. mPC2 precursor residue Arg 79 is substituted with any of a residue selected from the group Lys, His, Cys, Met, Phe, Tyr, Trp, Pro, Gly, Ala, Val, Ile, Leu, Ser, Thr, Asp, Glu, Gln, Asn, and most preferably Lys.

Insertion of DNA into a Cloning Vehicle

The cDNA or genomic DNA is inserted into a replicable vector for further cloning (amplification of the DNA) or for expression. Construction of suitable vectors containing the desired coding and control sequences employs standard recombinant techniques. Isolated plasmids or DNA fragments are cleaved, tailored, and religated to form the desired plasmid.

Many vectors are available, and selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence.

The preferred replicable vector is pRK5 or pRK7.

Signal Sequence Component

In general, the signal sequence may be a component of the vector, or it may be a part of the prohormone convertase DNA that is inserted into the vector. For example the native prohormone convertase DNA encodes a signal sequence at the amino terminus (5' end of the DNA) of the polypeptide that is cleaved during post-translational processing of the polypeptide to form the mature prohormone convertase polypeptide. Included within the scope of this invention are polypeptides with the native signal sequence deleted and replaced with a heterologous signal sequence. The heterologous signal sequence selected should be one that is recognized and processed (i.e. cleaved by a signal peptide) by the host cell. In mammalian cell expression the native signal sequence is generally satisfactory, although other mammalian signal sequences may be suitable.

Origin of Replication Component

Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even through it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of the prohormone convertase subunit DNA.

Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media.

One example of a selection scheme utilizes a drug to arrest growth of a host cell. Those cells that are successfully transformed with a heterologous gene express of protein conferring drug resistance and thus survive the selection regimen. Examples of such dominant selection use the drugs neomycin (Southern et al., *J. Molec. Appl. Genet.,* 1: 327 [1982]), mycophenolic acid (Mulligan et al., *Science,* 209: 1422 [1980]) or hygromycin (Sugden et al., *Mol. Cell, Biol.,* 5: 410–413 [1985]). The three examples given above employ bacterial genes under eukaryotic control to convey resistance to the appropriate drug G418 or neomycin (geneticin), xgpt (mycophenolic acid), or hygromycin, respectively.

An example of suitable selectable markers for mammalian cells are those that enable the identification of cells component to take up the prohormone convertase nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the polypeptide of interest. Amplification is the process by which genes in greater demand for the production of a protein critical for growth are reiterated in tandem within the chromosome of successive generations of recombinant cells. Increased quantities of the polypeptide of interest are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA,* 77: 4216 [1980]. The transformed cells are then exposed of increased levels of methotrexate. This leads to the synthesis of multiple copies of the DHFR gene, and, concomitantly, multiple copies of other DNA comprising the expression vectors, such as the DNA encoding the prohormone convertase. This amplification technique can be used with any otherwise suitable host, e.g., 293 or CHO cells, ATTC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding the polypeptide of interest, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

Promoter Component

Expression and cloning vectors usually contain a promoter that is recognized by the host organism and is operably linked to the nucleic acid encoding the polypeptide of interest. Promoters are untranslated sequences located upstream (5') to the start codon of a structural gene (generally within about 100 to 1000 bp) that control the transcription and translation of a particular nucleic acid sequence, such as that encoding a prohormone convertase, to which they are operably linked. Such promoters typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the polypeptide of interest by removing the promoter from the source DNA by restriction enzyme digestion and inserting the isolated promoter sequence into the vector. Both the native promoter sequence and many heterologous promoters may be used to direct amplification and/or expression of the polypeptide of interest. However, heterologous promoters are preferred, as they generally permit grater transcription and high yields of expressed polypeptide of interest as compared to the native prohormone convertase promoter.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal or addition of the poly A tail to the 3' end of the coding sequence. All of these sequences are suitably inserted into mammalian expression vectors.

Polypeptide transcription from vectors in mammalian host cells is controlled by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat-shock promoters, and from the prompter normally associated with the polypeptide of interest, provided such promoters are compatible with the host cell systems.

The early and late promoters of the SV40 virus are conveniently obtained as an SV40 restriction fragment that also contains the SV40 viral origin of replication. Fiers et al., *Nature,* 273:113 (1978); Mulligan and Berg, *Science,* 209: 1422–1427 (1980); Pavlakis et al., *Proc. Natl. Acad. Sci. USA,* 78: 7398–402 (1981). The immediate early promoter of the human cytomegalovirus is conveniently obtained as a HindIII E restriction fragment. Greenaway et al., *Gene,* 18: 355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature,* 295: 503–508 (1982) on expressing cDNA encoding immune interferon in monkey cells;, Reyes et al., *Nature,* 297: 598–601 (1982) on expression of human-interferon cDNA in mouse cells under the control of a thymidine kinase promoter from herpes simplex virus, Canaani and Berg, *Proc. Natl, Acad. Sci. USA,* 79: 5166–5170 (1982) on expression of the human interferon 1 gene in cultured mouse and rabbit cells, and Gorman et al., *Proc. Natl. Acad. Sci. USA.* 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Enhancer Element Component

Transcription of a DNA encoding the polypeptide of interest of this invention by higher eukaryotes is often increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins et al., *Proc. Natl. Acad. Sci. USA,* 78: 993 [1981]) and 3' (Lusky et al., *Mol. Cell Biol.,* 3: 1108 [1983]) to the transcription unit, within an intron (Banerji et al., *Cell,* 33: 729 [1983]) as well as within the coding sequence itself (Osborne et al., Mol. Cell Biol, 4: 1293 [1984]). Many enhancer sequences are now known from mammalian genes (globin, elastase, albumin, a-fetoprotein and insulin). Typically, however, one will use an enhancer from a eukaryotic cell virus. Examples includes the SV40 enhancer on the late side of the replication origin (bp 100–270), the cytomegalovirus early promoter enhancer, the polyoma enhancer on the late side of the replication origin, and adenovirus enhancers. See also Yaniv, *Nature,* 297: 17–18 (1982) on enhancing elements for activation of eukaryotic promoters. The enhancer may be spliced into the vector at a position 5' or 3' to the desired DNA, but is preferably located at a site 5' from the promoter.

Transcription Termination Component

Expression vectors used in eukaryotic host cells (insect, plant, animal, human, or mammalian cells) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the prohormone convertase. The 3' untranslated regions also include transcription termination sites.

Construction of suitable vectors containing one or more of the above listed components and including the desired coding and controls sequences employs standard ligation techniques. Isolated plasmids or nucleic acid fragments are cleaved, tailored, and religated in the form desired to generated the plasmids required.

Particularly useful in the practice of this invention are expression vectors that provide for the transient expression in mammalian cells of DNA encoding the polypeptide of interest. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying polypeptide analogs and variants that have desired activity.

Other methods, vectors, and host cells suitable for adaptation to the synthesis of the prophormone convertase and other polypeptides of this invention in recombinant mammalian cell culture are described in Gething et al., *Nature,* 293: 620–625 (1981); Mantel et al., *Nature,* 281: 40–46 [1979]; Levinson et al., EP 117,060; and EP 117,058. A particularly useful plasmid for mammalian cell culture expression of the prohormone convertase subunit is pRK5 (EP pub. no. 307,247) or pSV16B.

Selection and Transformation of Host Cells

Suitable host cells for cloning or expressing the vectors herein are the higher eukaryote cells described above. Suitable host cells for the expression of glycosylated polypeptide are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. However, interest has been greatest in vertegrate cells, and propagation of vertebrate cells in culture [tissue culture) has become a routine procedure in recent years (*Tissue Culture,* Academic Press, Kruse and Patterson, editors (1973)]. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.,* 36: 59 [1977]); baby hamster kidney cells (BHK, ATCC CCL 10); Chinese hamster ovary cells/-DHFR (CHO, Urlaub and Chasin, *Proc. Natl. Acad. Sci. USA,* 77: 4216 [1980]); mouse sertoli cells (TM4, Mather, *Biol. Reprod.,* 23: 243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383: 44–68 [1982]); MRC 5 cells; FS4 cells; and a human hepatoma cell line (Hep G2). Preferred host cells are human embryonic kidney 293 and Chinese hamster ovary cells.

Host cells are transfected and preferably transformed with the above-described expression or cloning vectors of this invention and cultured in conventional nutrient media modified as appropriate for inducing promoters, selecting transformants, or amplifying the genes encoding the desired sequences.

It is further envisioned that the cells comprising nucleic acid encoding the polypeptide of interest of this invention may be produced by homologous recombination, or with recombinant production methods utilizing controls elements introduced into cells already containing nucleic acid encoding the polypeptide of interest currently in use in the field. For example, a powerful promoter/enhancer element, a suppressor, or an exogenous transcription modulatory element is inserted in the genome of the intended host cell in proximity and orientation sufficient to influence the transcription of nucleic acid encoding a desired prohormone convertase. The control element does not encode the prohormone convertase of this invention, but affects the prohormone convertase nucleic acid which is present in the host cell genome. One next screens for cells making the prohormone convertase of this invention, or increased or decreased levels o expression, as desired.

Mammalian cells may be stably transformed using any acceptable vector known to transform a particular cell type. A preferred vector is the pRK5 used in the present invention with 293 human kidney cell. For example, the mammalian cells are transformed to produce a prohormone convertase and these cells are then used to produce properly processed hormone by transforming them to express a prohormone. Among the preferred prohormones are those that when processed result in hormones containing two or more polypeptide chains. Preferred two chain hormones are relaxin and insulin.

Culturing the host cells

Prokaryotic cells used to produce the polypeptide of this invention are cultured in suitable media as described generally in Sambrook et al., supra.

The mammalian host cells used to produce the polypeptides of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DEMEM], Sigma) are suitable for culturing the host cells. In addition, any of the media described in Ham and Wallace, *Meth. Enz.,* 58: 46 (1979), Barnes and Sato, *Anal. Biochem.,* 102: 255 (1980), U.S. Pat. No. 4,767,704; 4,657,866; 4,927, 762; or 4,560,655; WO 90/03430; WO 87/00195; U.S. Pat. No. Re. 30,985; or U.S. Pat. No. 5,122,469, issued Jun. 16, 1992 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentration in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The foregoing written specification is considered to be sufficient to enable one skilled in the art to practice the invention. Various modifications of the invention in addition to those shown and described herein will become apparent to these skilled in the art from the foregoing description and fall within the stops of the appended claims. The following examples are intended to illustrate the best mode now known for practicing the invention, but the invention is not to be considered limited to these examples.

EXAMPLE 1

Cloning of Murine Prohormone Convertases Type 1 (mPC1) and Type 2 (mPC2)

The mouse pituitary tumor cell line, AtT20, was used as the source for candidate prohormone convertase mRNA's. The AtT-20 cell line was obtained from the American Type Culture Collection (Rockville, Md.). Cells were grown in Dulbecco's modified Eagle's medium (DMEM) containing 10% fetal calf serum. Total RNA was prepared from confluent cells (Maniatis 1983) and cDNA was generated by incubation of 5 ug total RNA with 400 U Moloney murine leukemia virus reverse transcriptase (GIBCO-BRL), 2.5 mg GeneAmp 10 X reaction buffer (Perkin Elmer-Cetus), 20 U RNasin ribonuclease inhibitor (Promega), 400 nM dNTPs, 0.5 mg oligo-dT (United States Biochemical), 1.4 mM $MgCl_2$, 10 mM DTT; all in a total volume of 25 uL for 1 hour at 37 degrees C.

Amplification using a degenerate polymerase chain reaction (PCR) of candidate prohormone convertase targets was carried out in the same reaction tube by adding 50 pmol each of forward and reverse MOPAC PCR primers, 0.02 mmol dNTPs, with an additional 7.5 mL 10X reaction buffer plus 5 U Taq DNA polymerase. The primer sequences were based on the conserved aspartate and serine catalytic residues of KEX2, PC2, Proprotease B, and subtilisin BPN as described in Smeekens, et al (*The Journal of Biological Chemistry* Vol 265, pp. 2997–3000 [1990]). The forward primer used was: 5'GCAAAATCTAGA(C/T)(G/T)GCIAT(C/T)GTIGA(C/T)GA(G/T)GGI3' (SEQ ID NO:5) and the reverse primer was: 5'AAGCATGAGCTCIGG(A/G)GC(A/G)GC(A/G)GCIGAICC3' (SEQ ID NO:6). Thirty cycles of degenerate PCR were done, each consisting of denaturation (1 min, 94 degrees C.), primer annealing (2 min. 48 degrees C. for the first 5 cycles; 2 min at 55 degrees C. thereafter), and primer extension (3 min. 72 degrees C.). The products from the PCR reaction were electrophorested in a 2.5% NuSieve-GTG low melting agarose gel (RMC). Biscrete bands of approximately 600 bp were excised and subcloned into pUC118 for DNA sequence analysis. Partial mPC1 and mPC2 sequences were derived by this procedure.

A cDNA pool was prepared as a source of template for the cloning of full length sequences of the candidate PC enzymes (Frohman 1988; Innis 1990). Mouse AtT-20 total RNA (5 mg) was heated for 3 min at 65° C. and immediately chilled on ice. The denatured RNA was added together with 200 U reverse transcriptase to a first strand cDNA synthesis reaction containing 4 mL 5X H-RT buffer (GIBCO-BRL), 10 mM DTT, 1 mM dNTPs, 20 U RNasin, and 2.5 pmol $R_o R_i$-d(T)$_{17}$ adapter primer; 5'GATATCACTCAGATCGATGAATTCGAGCTC(T)17 3' (SEQ ID NO:7) all in a final volume of 20 uL. The mixture was incubated for 1 hour at 37 degrees C. and diluted to 1 mL with Tris/EDTA. Aliquots (5–10 uL) of the cDNA pool were used for amplification of unknown 3' and 5' regions by RACE-PCR (rapid amplificaiton of cDNA ends, Frohman 1988; Innis 1990) using a combination of gene-specific PCR primers (for mRC1 they were: 3'RACE primer 5'AAGCTTTTCTAGAGGATCCCTCTGGTGGATTTGG3' (SEQ ID NO:8) and 5'RACE primer 5'AAGCTTGAATTCTCCAACCCCACACTTGTG3'(SEQ ID NO:9) and the inner adapter $R_i$ PCR primer 5'AGATC-GATGAATTCGAGCTC 3'(SEQ ID NO:10). Final construction of the full length mPC1 and mPC2 cDNAs was though the technique of recombinant PCR (Innis 1990). All PCR cloning reactions were carried out with Vent DNA polymerase (New England Biolabs) to minimize the introduction of mismatched bases during amplification of template.

All mPC clones were sequenced with the Sequenase 2.0 kit from USB and cloned into PUC118 (Vieira, et al *Methods Enzymology* 153 [1987]).

EXAMPLE 2

Relaxin Production in Transfected Cells

Construction of relaxin and prohormone convertase expression vectors

The cDNA clone of the preprorelaxin gene, pCIS.Rx, provided the coding sequence of the human preprorelaxin. The pCIS mammalian expression vector is described in (Gorman *DNA Prot Eng Tech* 2:3–10, 1990). The cDNA encoding H2 preprorelaxin was excised from the cloning vector as described in Hudson, P et al., *The EMBO Journal* 3, 2333–2339, [1984] by using a complete Hpa II digest followed by a Hinf I partial digest. pCIS.Rx was digested by restriction endonucleases XBA I and ECO RI to excise the coding region of preprorelaxin. pRK7 was digested by restriction endonucleases XBA I and ECO RI. The resultant XBA I/ECO RI human preprorelaxin coding region was ligated into the XBA I/ECO RI digested pRK7 yielding the final preprorelaxin mammalian expression vector, pRK.Rx.

The cDNA clone of the mPC1 gene, PUC118.mPC1 from example 1, provided the coding sequence of the mPC1 for construction of plasmids to direct the expression of mPC1 in transfected mammalian cells. PUC118.mPC1 is digested with restriction endonucleases SAC I and ECO RI. pRK7 is digested with restriction endonucleases SAC I and ECO RI. The resultant SAC I/ECO RI mPC1 coding region is ligated into the SAC I/ECO RI digested pRK7 to yield the final mPC1 mammalian expression vector, pRK.mPC1.

The cDNA clone of the mPC2 gene, PUC118.mPC2 from example 1, provided the coding sequence of the mPC2 for construction of plasmids to direct the expression of mPC2 in transfected mammalian cells. PUC118.mPC2 is digested with restriction endonucleases XBA I and ECO RI. pRK7 is digested with restriction endonuclease XBA I and ECO RI. The resultant XBA I/ECO RI mPC2 coding region is ligated into the XBA I/ECO RI digested pRK7 to yield the final mPC2 mammalian expression vector, pRK.mPC2.

The cDNA clone of the KEX2 gene, pYEp24.pJ28 (Julius, et al, Cell vol 37, p 1075 [1984]) provided the coding sequence of the KEX2 gene for construction of the final KEX2 mammalian expression plasmid. Vector pYEp24.pJ28 was digested with restriction endonuclease Eco RI and run on an Agarose gel. A 3.3 kb fragment containing the coding region was isolated. pRK5 was digested with restriction endonuclease Eco RI, and then treated with bacterial alkaline phosphate (BAP). The Eco RI digested, BAP treated pRK5 was run on an agarose gel and a 4.7 kb fragment was isolated, The 3.3 kb fragment of pYEp24.pJ28 was ligated to the 4.7 kb fragment of pRK5 to form vector pRK.KEX.RI. pRK.KEX.RI was digested with restriction nuclease Dde I, then treated with Klenow, and further digested with restriction endonuclease Hind III. The Dde I/Hind III treated pRK.KEX.RI was run on a polyacrylamide gel and a 425bp fragment was isolated. pRK5 was digested with restriction endonuclease Sma I/Hind III, then treated with BAP, run on an agarose gel and a 4.7 kb fragment was isolated. The 4.7 kb fragment of pRK5 was ligated to the 425 bp fragment of pRK.KEX.RI to form vector pRK5.5'KEX. pRK5.5'KEX was digested with Hind III and treated with BAP. A 2 kb Hind III fragment encoding the 3' end of KEX2 was derived from vector pYEp24.pJ28 and was ligated to the Hind III/BAP treated vector pRK5.5'KEX forming the final KEX mammalian expression vector pRK.KEX2 which directs the expression of KEX2 in transfected mammalian cells.

Transient transfection of relaxin in human kidney 293 cells.

Human kidney 293 cells were subjected to transient transfection by the method of Gorman (Gorman *DNA Prot Eng Tech* 2:3–10, 1990). Expression vector containing prorelaxin cDNA, pRK.Rx, (10 ug) was transfected into 293 cells alone (100 mm dish), or together with an equal amount of expression vectors for mPC1 (pRK.mPC1), mPC2 (pRK.mPC2) or kex2 (pRK.kex2) cDNAs.

Stable transfection of relaxin in Human Kidney 293 Cells

General aspects of mammalian cell host system transformations have been described by Axel in U.S. 4,399,216 issued Aug. 16, 1983. The preferred method for stable transformation of a mammalian cell of the present invention is the calcium phosphate precipitation method described in sections 16.30–16.37 of Sambrook et al, supra. The preferred host cell is the human embryonic kidney line (293) or Chinese hamster ovary cells/-DHFR(CHO). The preferred media contains the antibiotic neomycin or geneticin.

Characterization of Processed Relaxin Immunoaffinity purification

Following transfection, culture medium was removed and replaced by 2 mL DMEM (minus cysteine and methionine) containing 200 uCi each of 35S-cysteine and 35S-methionine (Amersham). After a 3 hr incubation, the supernatant was collected and cells were washed with PBS. Cells were lysed with 1 mL lysis buffer (150 mM NaCl, 1% NP-40, 50 mM Tris-HCl pH 8.0). Both supernatant and whole-cell lysate were analyzed by immunoprecipitation.

Supernatants (500 uL) and whole-cell lysates (250 uL) from the transfections were mixed with 5 mg of anti-relaxin monoclonal antibody (MabR1x6) for an overnight incubation, with gentle rocking at 4 degrees C. Antibody-antigen complexes were absorbed onto protein A-Sepharose CL4B beads (Pharmacia-LKB) at 4 degrees C. for 1 hour. The beads were briefly centrifuged and gently washed three times with lysis buffer. Liquid was aspirated off and 50 mL 2xtricine/SDS sample buffer (25% glycerol, 8% SDS, 1.5% Serva Blue G, 0.9 M Tis.HCl pH 8.45) was added to the beads. Samples were heated for 10 min at 85 degrees C. and 10 uL aliquots were applied to pre-cast tricine/SDS 10–20% polyacrylamide gradient gels (Novex). Following electrophoresis, gels were fixed, soaked in Ampligy (Amersham), dried and exposed to X-ray film at –80 degree C.

Following transfection of 293 cells with the expression plasmid for prorelaxin, pRK.Rx, only the precursor prorelaxin immunoprecipitated from cell lysates or cell supernatants. The prorelaxin bands at about 6.0 KD on a 10–20% polyacrylamide gradient gel.

Co-transfection of 293 cells with the expression plasmid for prorelaxin, pRK.Rx, and pRK.mPC2, which directs expression of the mouse mPC2 cDNA, yields only the precursor prorelaxin, indicating that mPC2 is not involved in processing native prorelaxin in this system.

Co-expression of prorelaxin and mPC1 cDNA's or prorelaxin and KEX2 yielded mature, bonafide relaxin, which bands at about 3.0 KD on a 10–20% polyacrylamide gradient gel.

Reverse phase HPLC and mass spectrometry analysis

For preparative analysis of cell-secreted protein, three 10 cm dishes of confluent cells were transfected with substrate proH2Relaxin alone, or with a combination of proH2Relaxin (wild-type or mutant) and processing enzyme cDNAs, A total of 30 uL of supernatant was collected from each transfection and passed twice over a small (300 uL) column of anti-relaxin monoclonal antibody linked to Sepharose-CL4B for immunoaffinity purification. The column was washed with PBS and no-specifically absorbed material was removed by a 1 M NaCl in PBS wash, followed by 2 M guanidine.HCl in 1.0 mM Tris.HCl pH 7.5. Antibody-bound protein was eluted with a small volume of 4 M guanidine.HCl/Tris.HCl.

The immunoaffinity column eluant was applied without further purification to a 2×100 mm, RP-C4 reverse phase HPLC column (Synchrom). Material was eluted by application of a linear gradient of acetonitrile in 0.1% Trifluoroacetic acid from 20% (0–5 min) to 60% (5–45 min). The flow rate was held at 0.5 mL/min and the absorbance at the column outlet was monitored at 214 nm. Eluants from major peaks of absorbance were collected for analysis by mass spectrometry (FIG. 8).

The intact molecular weights of prorelaxin and processed relaxin were measured by electrospray ionization mass spectrometry. Micromolar solutions (1–10 pmol/ul) of protein in aqueous acetonitrile (50/50, v/v) with 1% acetic acid were infused at 1.5 ul/min into a SCIEX API III mass spectrometer. The quadrupole mass spectrometer was operated with the Ionspray articulated nebulizer (SCIEX, Thornhill, Canada) at 4600 V, the interface plate at 600 V, and the orifice at 100–120V.

Data were collected every 0.1 v with the quadrupole scanning from 600–2200 u in 32 seconds. Molecular weights of the individual A and B chains were determined by fast atom bombardment (FAB) mass spectrometry following on-probe reduction as described by Stults et al.(*Biomed Environ Mass Spectrom* 19:655–664 {1991}).

Transfection of pRK.Rx alone resulted in the secretion of prorelaxin as the major product. This species had an HPLC elution time of 29 minutes. Co-transfection of pRK.Rx with either pRK.MPC1 or pRK.KEX2 generated a major species that gave an HPLC retention time of 17 minutes. This retention time was very similar to that observed for authentic mature relaxin purified from human corpus luteum.

Co-transfection major peaks eluting from the column were collected for analysis by mass spectrometry. Electrospray measurements generated mass values consistent with authentic mature relaxin. This was confirmed further by fast atom bombardment analysis of reduced 5963 Da species. Two peaks of 2657 and 3313 mass units were obtained, exactly corresponding to the predicted values for reduced relaxin A and B chains, respectively. Material from the 5963 Da relaxin was subjected to several rounds of N-terminal peptide sequencing in a gas phase sequencer. No sequence was obtained for the A-chain as expected due to the pyroglutamyl residue that blocks its N-terminus. All amino acids detected were from the B chain and had a peptide sequence consistent with correct removal of the 24 amino acid signal sequence that precedes the B chain. Additionally, the mature B-chain terminates with a serine residue at its C-terminus suggesting that carboxypeptidase activity present in the 293 cells removed the residual basic residues, KR, which remain following cleavage at the B-chain/C-peptide junction.

EXAMPLE 3

Human Relaxin Mutants and PC Specificity

Prohormone convertase substrate specificity is exemplified by processing of human prorelaxin mutants. A series of mutant prorelaxin cDNAs were made in which basic residues thought to be required for processing were replaced with alanine. Two dibasic residues, KR, are located at the B-chain/C-peptide junction and both are required for processing, When either of these basic amino acids is replaced by alanine, unprocessed prorelaxin is secreted from the 293 cells. There is no indication of intermediate proteins indicative of a partially processed precursor, which might have resulted from partial cleavage at the C-peptide/A-chain junction.

Site-directed mutagenesis of prorelaxin

Site-directed mutagenesis was performed on the relaxin mammalian expression vector, pRK.Rx, by the method of Kunkel (Kunkel 1987) with some minor modifications. Transformation-competent ($CaCl_2$) CJ236 strain of E. Coli was used as the bacterial host for the synthesis of uracil-containing template phagemid DNA, and T4 enzyme, The oligonucleotide extension reaction was performed in a 10 uL volume for an initial period of 15 min at room temperature, followed by a 75 min incubation at 37 degrees C. The reaction was terminated by the addition of Tris/EDTA buffer to a final volume of 50 uL. A 10 uL aliquot was used to transform an ung$^+$ strain of E. coli, MM299, for selection against uracil-containing wild-type template DNA. This strain was also used to produce single strand DNA for use in sequencing analysis by the chain termination method (Sequenase kit, United States Biochemical).

Identification of prohormone convertase substrate specificity.

Prorelaxin alanine mutations of the basic residues K and R were constructed to define murine prohormone convertase 1 specificity. FIG. 11. The following mutations were tested for substrate specificity to murine prohormone convertase 1: 1.4, 2.4, 3.2, 4.3, 7.2 and 8.6. The relaxin (Rx) mutants have the following sequence in the prohormone convertase cleavage site.

```
C-chain/A-chain junction mutants
Native Rx  H   S   R   K   K   R   Q   (SEQ ID NO:48)
           CAT TCT CGA AAA AAG AGA     (SEQ ID NO:11)
           CAA Rx 1.4     H   S   V   K   K   R   Q   (SEQ ID NO:49)
           CAT TCT GTA AAA AAG AGA     (SEQ ID NO:12)
           CAA Rx 2.4     H   S   R   A   K   R   Q   (SEQ ID NO:50)
           CAT TCT AGA GCA AAG AGA     (SEQ ID NO:13)
           CAA Rx 3.2     H   S   R   K   A   R   Q   (SEQ ID NO:51)
           CAT TCT AGA AAA GCA AGA     (SEQ ID NO:14)
           CAA Rx 4.3     H   S   R   K   R   A   Q   (SEQ ID NO:52)
           CAT TCT AGA AAA AGA GCA     (SEQ ID NO:15)
           CAA B-chain/C-chain junction mutants
Native Rx  T   W   S   K   R   S   L   (SEQ ID NO:53)
           ACC TGG AGC AAA AGG TCT     (SEQ ID NO:16)
           CTG Rx7.2      T   W   S   A   R   S   L   (SEQ ID NO:54)
           ACC TGG AGC GCT AGG TCT     (SEQ ID NO:17)
           CTG Rx8.6      T   W   S   K   A   S   L   (SEQ ID NO:55)
           ACC TGG AGC AAA GCT TCT     (SEQ ID NO:18)
           CTG
```

FIG. 9 illustrates murine prohormone convertase 1 processing of these mutants. Mutants 1.4 and 2.4 are processed the same as wild-type and mutant 3.2 is partially processed. Mutant 4.3 doesn't appear to be processed and mutants 7.2 and 8.6 are not processed. Disrupting the B-C chain junction at either the position mutated at mutants 7.2 or 8.6 prevents any cleavage of prorelaxin. The C-A chain is probably not available for cleavage by murine prohormone convertase 1 until the B-C chain junction is cleaved. This data supports a progressive cleavage mechanism involving cleavage of this upstream site first. The B-C chain site requires both basic residues. Mutants 3.2 and 4.3 point out that while basic residues are required (as seen with 7.2 and 8.6) they are not sufficient, Both mutants 3.2 and 4.3 have intact KR sites and mutant 3.2 is not cleaved as well as wild-type and mutant 4.3 is not cleaved by murine prohormone convertase 1.

Murine prohormone convertase 2 does not cleave the wildtype prorelaxin. Murine prohormone convertase 2 does not cleave any of the prorelaxin mutants with the exception of 4.3 where there is some processing. This suggests that there is a difference in the specificity of cleavage for murine prohormone convertase 1 and murine prohormone convertase 2 which is defined by sequences other than the dibasic residues. Non-substrate proteins can be made to be substrates by appropriate mutagenesis. Mutant 7.2 is not cleaved by murine prohormone convertase 2. Mutation of an upstream site in prorelaxin prevents downstream cleavage illustrating the presence of progressive cleavage of prorelaxin.

EXAMPLE 4

Construction of Proinsulin Mutants and Insulin Expression in Transfected 293 Cells The cDNA clone of the human preproinsulin gene, pSVEHIGDHFR, described in Australian patent 616,201 issued Feb. 18, 1992, provided the coding sequence of the human preproinsulin gene for the final mammalian expression vector. Aliquots (5–10 uL) of pSVEHIGDHFR were used for amplification of the coding region by RACE-PCR (rapid amplification of cDNA ends, Frohman 1988; Innis 1990) using a combination of gene-specific PCR primers: for the 5' end they were CAT AAG CTT ACC ATG GCC CTG TGG ATG CGC (SEQ ID NO:18) (sequence given 5'to 3') and for the 3' end they were CAT TCT AGA CTA GTT GCA GTA GTT CTC CAG (SEQ ID NO:19) (sequence given 5' to 3'). All PCR cloning reactions were carried out with Vent DNA polymerase (New England Biolabs) to minimize the introduction of mismatched bases during amplification of template. All proinsulin clones were sequenced with the Sequenase 2.0 kit from USB and cloned into restriction digested pRK5. The final preproinsulin mammalian vector is pRK.proins.

A human proinsulin mutant having a non-naturally occurring prohormone convertase cleavage site is constructed by mutating the human proinsulin cDNA, pRK.proins, encoding the naturally occurring basic cleavage site at the B-chain/C-peptide junction (KTRR) (SEQ ID NO:20) and/or A-chain/C-peptide junction (LQKR) (SEQ ID NO:21) by site-directed mutagenesis (Kunkel 1987). The following proinsulin variants were constructed: proins.RTKR.Ip (SEQ ID NO:22), proins.RQKR.IIP (SEQ ID NO:23), proins.RK-TKR.Ip (SEQ ID NO:24), The following double proinsulin variants were constructed: proins.KR.Ip/RQKR.IIp (SEQ ID NO:23), and proins.RTKR.Ip (SEQ ID NO:22)/RQKR.IIp (SEQ ID NO:23). Ip is the Type I enzyme cleavage site and IIp is the Type II enzyme cleavage site.

Primers used in proinsulin mutant construction were the following:

```
PROINS.RTKR.Ip    CTCTGCCTCCCGCTTGGTCCTGGGTGTGTAG
                  (SEQ ID NO:25)

PROINS.RQKR.IIp   CACGCTTCTGCCGGGATCCCTC
                  (SEQ ID NO:26)

PROINS.KTKR.Ip    CTCTGCCTCCCGCTTGGTCTTCGGTGTGTAG
                  (SEQ ID NO:27)
```

The sequences are listed in 5'→3' orientation.

The double proinsulin mutant prions.KR.Ip/RQKR.IIp (SEQ ID NO:23) changes the native human proinsulin residue Arg 31 to Lys 31 at the Type I enzyme cleavage site, and proinsulin residue Leu 62 is changed to Arg 62 at the Type II enzyme cleavage site.

The double proinsulin mutant proins RTKR.Ip (SEQ ID NO:22)/RQKR.Tlp (SEQ ID NO:23) changes the native human proinsulin residue Lys 29 to Arg 29 at the Type I enzyme cleavage site, residue Arg 31 to Lys 31 at the Type I enzyme cleavage site and proinsulin residue Leu 62 is changed to Arg 62 at the Type 11 enzyme cleavage site.

All mutants were screened through the primer regions with the Sequenase 2.0 kit from USB.

DNA from all proinsulin mutants and naturally occurring proinsulin was CsCl banded and used for 293 cell transient transfection by the method of Gorman (Gorman *DNA Prot Eng Tech* 2:3–10, 1990. The next day, cells were labeled with 35S Met and 35S Cys (200 uCi/ml) and labeled for 4–6 hours.

Immunoaffinity purification

Supernatants (500 uL) or whole-cell lysates (500 uL) from the transfections were mixed with 4 ul of Conc. Guinea Pig Anti-Human Insulin Lot I01, from Biomeda for an overnight incubation, with gentle rocking at 4 degrees C. Protein A Sepharose (CL4B-Pharmacia 17-0963-03) was prepared by washing 5 mls of Protein A Sepharose with NP40 lysis buffer. The wash procedure was repeated 4 times. After the last wash was aspirated, enough buffer was added to provide a 25% v/v slurry of Protein A Sepharose-C14B. 100 ul 25% protein A slurry was added to each overnight sample containing the Conc. Guinea Pig Anti-Human Insulin Lot I01, from Biomeda. Incubate 1 hour at 4 degrees with rocking. Centrifuge 15 seconds, aspirate supernatant into waste, and wash 3 times with NP 40 lysis buffer. Aspirate buffer. Add 30 ul 2x Tricine-SDS sample buffer to each sample tube. Heat 100 degrees for 10 minutes and apply 10 uL aliquots to pre-cast tricine/SDS 16% polyacrylamide gradient gels (Novex). Following electrophoresis, gels were fixed, soaked in Ampligy (Amersham), dried and exposed to X-ray film at −80 degree C.

Gel results

Transfections using native human proinsulin DNA resulted in a prominent protein band at 6.5 KD and a faint band at 3.4 KD. Transfections using the DNA of proinsulin variant proins.RTKR.Ip (SEQ ID NO:22)/RQKR.IIp (SEQ ID NO:23), resulted in protein bands at 3.4 KD and 2.35 KD where authentic insulin B and A chains, respectively, run on 16% tricine/SDS polyacrylamide gradient gels (NOVEX).

Transfections using the DNA of proinsulin mutants, proins.RQKR.IIp (SEQ ID NO:23) or double mutant proins.KR.Ip/RQKR.IIp (SEQ ID NO:23), resulted in two bands, one band at about 6.0 KD representing the B-chain/C-peptide intermediate band and one band at 2.35 KD representing the insulin A-chain.

Transfections using the DNA of proinsulin variant, proins.RTKR.Ip (SEQ ID NO:22), resulted in two bands, one band running slightly below the B-chain/C-peptide intermediate band representing the C-peptide/A-chain intermediate band and one band at 3.4 KD representing the insulin B-chain.

Transfections using the DNA of proinsulin mutant, proins.KTKR.Ip (SEQ ID NO:24) resulted in one prominent band at 6.5 KD and a faint band at 3.4 KD.

EXAMPLE 5

Construction of Prohormone Convertase Mutants

Prohormone convertase precursor residues involved in processing of the precursor form of the prohormone convertase to the bioactive form of the prohormone convertase are mutated such that the prohormone convertase precursor is processed by the prohormone convertase naturally occurring in the human kidney 293 cell.

Site-directed mutagenesis of the mammalian expression vector, pRK.mPC1 or mammalian expression vector, pRK.mPC2 is by the method of Kunkel (Kunkel 1987). The following primers were used in the Prohormone Convertase precursor mutant construction:

mPC1 primer GAT ATG AAG AGC AGA TCT TTT GGA CCT CCG AGG ATG (SEQ ID NO:28)
mPC2 primer CTT ATG GTG TAA GCT TCG TTT TGC TCT GGC CTT TGC AAG (SEQ ID NO:29) where primers are given in a 5' to 3' direction.

The PC1 primer results in a mammalian prohormone convertase 1 mutant having the native residue ARG.80 mutated to LYS.80.

The PC2 primer results in a prohormone convertase mutant having the native mammalian prohormone convertase 2 residues LYS.77 ARG.78 ARG.79 mutated to ARG.77 ALA.78 LYS.79

All mutants were screened through the primer regions with the Sequenase 2.0 kit from USB.

EXAMPLE 6

Processing of NGF, BNDF and NT-3 Mutants by mPC 1 and 2

To elucidate the role of the precursor in the processing of the neurotrophic factors, chimeric pRK5 expression vectors were constructed to contain the precursor of NGF, NT-3, or BDNF linked to the mature portion of NGF or the NT-3 precursor linked to the mature portion of BDNF. The entire PCR amplified region of each chimera containing the NGF mature sequence was found to be identical to the published sequences for each precursor portion and for the mature NGF with the exception of a silent point mutation in codon #403 in pRK5.BDNFNGF. Plasmid vector pRK5 was used in all constructions.

Nerve Growth Factor (NGF), Neurotrophic Factor 3 (NT-3), or Brain Derived Neurotrophic Factor (BDNF)

Nerve Growth Factor (NGF), Neurotrophic Factor 3 (NT-3), or Brain Derived Neurotrophic Factor (BDNF) cDNA were inserted into the cloning linker of pRK5 producing pRK5.NGF, pRK5.BDNF, and pRK5.NT-3. Plasmid DNA was transformed into *E. coli* 294 cells and cultured to saturation in 1 liter of Super Broth (12% tryptone in H2O, 24% yeast extract in H2O, 0.5% glycerol, 70 mM K$_2$HPO$_4$), 25 mM KH$_2$PO$_4$). The plasmid DNA was isolated by alkaline lysis and purified via cesium chloride double banding according to the procedures in Sambrook et al. (1989).

pRK.NT3NGF plasmid construction

DNA encoding prepro NT-3 was spliced to the DNA encoding the mature portion of NGF using a polymerase chain reaction (PCR) (Saiki et al., 1985, Mullis et al. 1986). 0.5 μg of both pRK5.NT3 and pRK5.NGF were linearized with Hind III. The precursor portion of NT3 was amplified using primers a and b while the mature portion of NGF was amplified using the c and d primers as shown in Table 1.

with Sst II and Hind III. Digestion products were electrophoresed on a 1% NuSieve gel. The 533 base pair fragment was cut out of the gel and used in the ligation reactions described below to generate the pRK5.NT3NGF fusion plasmid.

Plasmid pRK5.NT3 was digested to completion with HindIII and Eco RI in one reaction and Eco RI and Sst II in a second reaction. Reaction products were electrophoresed on a 1% NuSieve gel. The 4681 and 337 base pair bands were cut out of the gel, melted, and ligated together with the melted 533 base pair fusion product described above according to standard protocol. (Maniatis, 1989). Ligation products

| PRIMER | SEQUENCE 5'-->3' | LOCATION/strand |
|---|---|---|
| a | TACAACTCACCGCGGGTCCTG<br>1247–1267 NT3/S | (SEQ ID NO:30) |
| b | AAGATGGGATGGGATGATGACCGTTTCCGCCTTGATGT<br>1349–1366 NT3/AS<br>1407–1426 NGF/AS | (SEQ ID NO:31) |
| c | ACATCACGGCGGAAACGGTCATCATCCCATCCCATCTT<br>1349–1366 NT3/S<br>1407–1426 NGF/S | (SEQ ID NO:32) |
| d | GATATAAGCTTGAGAGTGTAGAAGGGGC<br>1794–1810 NGF/AS | (SEQ ID NO:33) |

The location of priming within each plasmid is listed as well as the strandedness ("S" indicates sense primers and "AS" indicates antisense primers). PCR was performed on a Thermal Cycler 460 (Perkin-Elmer Cetus) under the following conditions: 100 ML reaction volumes, 50 pmol primers, 200 μM dNTP's, 10 mM b-mercaptoethanol, 16.6 mM (NH$_4$)$_2$SO$_4$, 67 nM Tris-HCl pH 8.8, 6.7 mM MgCl$_2$, 6.7 mM EDTA, and 0.15 mg/ml BSA. The reaction cycle consisted of denaturation at 94 degrees C. for 1 min, annealing at 55 degrees C. for 1 min, and elongation at 72 degrees C. for 3 min. After 35 cycles, aliquots of PCR reactions 1 and 2 were purified on an 8% acrylamide gel. Bands of 119 base pairs for the NT3 precursor and 414 base pairs for NGF mature were cut out and the DNA was recovered via electroelution as previously described (Maniatis et al. 1982).

Purified products from reactions 1 and 2 were spliced together in PCR reaction 3 using the a and d primers under the same amplification conditions. (Both a and d primers contain a restriction site that will be used for cloning hack into the pRK vector.)

Final PCR reaction products were phenol/chloroform extracted, ethanol precipitated, and digested to completion were melted for 5 minutes at 65 degrees C., diluted with 100 μl 10 mM MgC$_2$, and transformed into *E. coli* 299 cells. After picking colonies and screening them via restriction endonuclease digestion, single stranded DNA was prepared and sequenced through the entire PCR fusion area as previously stated.

pRK5.BDNFNGF plasmid construction

The BDNF precursor was fused to mature NGF in a similar manner as above with the exception that the fusion area was created in just one PCR reaction. 0.5 Mg of Hind III linearized pRK5.BDNF and pRK5.NGF DNA was amplified in one reaction containing all four primers: a,b,c, and d (Table 2). All other conditions of the amplification were as stated above. The PCR products were phenol/chloroform extracted, ethanol precipitated and digested to completion with Bst BI and Hind III. Digestion products were electrophoresed on a 1% NuSieve gel and the 650 base pair fusion band was cut out and saved for the ligation below.

x Primers used in pRK5.BDNFNGF construction are shown below:

| PRIMER | SEQUENCE 5'-->3' | LOCATION/STRAND |
|---|---|---|
| a | GGCTTGACATCATTGGCTGACACTTTCGAACACATGATAG<br>1332–1371 BDNF/S | (SEQ ID NO:34) |
| b | AAGATGGGATGGGATGATGAGCGCCGGACCCTCATGGACAT<br>1533–1553 BDNF/AS<br>1407–1426 NGF/AS | (SEQ ID NO:35) |
| c | ATGTCCATGAGGGTCCGGCGCTCATCATCCCATCCCATCTT<br>1533–1553 BDNF/S<br>1407–1533 NGF/S | (SEQ ID NO:36) |

-continued

| PRIMER SEQUENCE 5'-->3' | LOCATION/STRAND |
|---|---|
| d   GATATAAGCTTGAGAGTGTAGAAGGGGC<br>     1794–1810 NGF/AS | (SEQ ID NO:37) |

The location of priming within each plasmid is listed as well as the strandedness ("S" indicates sense primers and "AS" indicates antisense primers).

Plasmid pRK5.BDNFNGF was constructed by digesting pRK5.BDNF to completion with Hind III and Bst BI. The products were electrophoresed on a 1% NuSieve gel. The 5181 base pair band was cut out, melted, and ligated to the melted 650 bp PCR fusion band. Ligation products were transformed, screened, and sequenced through the PCR region as stated above.

DNA for all of the above constructs was prepared via cesium chloride banding as stated earlier.

pRK5.NT3BDNF Plasmid Construction

Plasmid pRK5.NT-3 and pRK5.BDNF were digested to completion with Esp I and Kpn I. Digestion products were electrophoresed on a 1% NuSieve gel. The 4810 and 944 base pair fragments were cut out of the gel and ligated together. The missing 126 base pair region containing the 3' end of the NT-3 precursor and the 5' end of the BDNF mature was prepared using synthetic DNA oligonucleotides. Six overlapping primers (sense and anti-sense, Table 3) were ligated together in one reaction according to standard protocol. The ligation products were then digested with Esp I to generate the 126 base pair fusion fragment. Plasmid pRK5.NTBD was digested to completion with Esp I and ligated to the 126 base pair fragment. Following screening, pRK5.NT3BDNF was sequenced throughout the entire 126 basepair fusion area.

Primers used in NT3BDNF Synthetic Fusion Area are shown below.

Kunkel mutagenesis

To control for variation in the 5'portion of each gene within the vector and to optimize conditions for translation of the neurotrophic mRNA's, an 'ACC' translation consensus sequence was added to the 5' ends of the cDNA inserts and extra base pairs of 5' sequence originally cloned into pRK5.BDNF (including two ATG sites) and pRK5.NGF was removed. Kunkel Mutagenesis was performed on plasmids pRK5.NGF, pRK5.NT-3, pRK5.BDNF, pRK5.NT3NGF and pRK5.BDNFNGF. 2 µg plasmid DNA was transformed into $CaCl_2$ competent *E. coli* strain CJ236. Single stranded uracil containing template DNA was prepared according to Sambrook et al. (1989) with the exception that after PEG precipitation, the pellet was resuspended in 100 µL TE, extracted once with 50 µL phenol/chloroform (1:1), and twice with 500 µL chloroform. After ethanol precipitation, the pellet was resuspended in 45 µL $dH_2O$ and spun-dialysed through a Sepharose CL-6B (Pharmacia/LKB) column. 100 pmol synthetic oligonucleotide primers containing the 5' ACC (Table 4) were phosphorylated with T4 polynucleotide kinase. Mutagenesis was performed using the Muta-Gene Phagemid in vitro Mutagenesis kit (BioRad) according to manufacturer's instructions. The products were transformed into *E. coli* 299 cells and resulting colonies were picked and screened. Single stranded DNA was prepared for sequencing (Sambrook et al., 1989) with the following modifications: precipitation of the phagemid particles was at 4 degrees C. followed by resuspension in 0.3 M NaOAc/1 mM EDTA. DNA was extracted with a 2X volume of phenol/chloroform. The final pellet was resuspended in 50 µL $dH_2O$. Single-

| Primer Sequence 5'-->3 ' | |
|---|---|
| 1s   TGAGCGACAGCACCCCCTTGGAGCCCCCGCCCTTGTATCTCATGGAGGATT | (SEQ ID NO:38) |
| 1a   TCAGCTCCCCTCGTCGGGCGGGGTCCGAGTGCCGTTTCCGCCGTGATGTTC | (SEQ ID NO:39) |
| 2s   ACGTGGGCAGCCCCGTGGTGGCGAACAGAACATCACGGCGGAAACGGC | (SEQ ID NO:40) |
| 2a   TGTTCGCCACCACGGGGCTGCCCACGTAATCCTCCATGAGATACAAGG | (SEQ ID NO:41) |
| 3s   ACTCGGACCCCGCCCGACGAGGGGAGC | (SEQ ID NO:42) |
| 3a   GCGGGGGCTCCAAGGGGGTGCTGTCGC | (SEQ ID NO:43) |

The "s" following the number of the plasmid indicates a sense strand plasmid and the "a" indicates an anti-sense strand. The primers were constructed to overlap each other when ligated together.

stranded plasmid DNA was sequenced through the priming area with the Sequenase Version 2.0 Sequencing Kit (USB) according to manufacturer's instructions.

TABLE 4

Primers (antisense) used in 5'Kunkel Mutagenesis

| Primer | Sequence 5'-->3' | |
|---|---|---|
| NGF | 5'GTAGAACAACATGGACATGGTGGCAATATTGTCGAC TCTGGAGTCGACCTGCAG | (SEQ ID NO:44) |
| NT3. | 5'CACATAAAACAAGATGGACATGGTCTTGTTCACCTGTA GGATCCCCGG | (SEQ ID NO:45) |
| BDNF | 5'AGTAAGGAAAAGGATGGTCATGGTGGAGGTCGA CAAGCTTGAGAATTCAATCG | (SEQ ID NO:46) |

The altered restriction sites used for screening purposes are underlined.

Cell Culture—ELISA

Plasmids were prepared for transfection via cesium chloride double banding. Both the original plasmids and the 5' end mutagenized plasmids pRK5.NGF, pRK5.NT3NGF, and pRK5.BDNFNGF were transfected along with an hGH control plasmid into the human kidney cell line (293) using the calcium phosphate precipitation method (Gorman et al. 1990). 36 hours post-transfection the supernatants were assayed for NGF and hGH (as a control) expression with the enzyme linked immunosorbant assay (ELISA). ELISA's were performed by Immunoassay Services, Genentech, Inc. Supernatants of all construct transfections were also assured to have bioactivity by their effects on dorsal root ganglia and sympathetic neurons.

Cell culture—radioactive protein labelling

Plasmids pRK5.NGF, pRK5.NT-3, pRK5.BDNF, pRK5.NT3NGF, pRK5.BDNFNGF and pRK5.NT3BDNF were transfected into the human kidney cell line (293). 24 hours post transfection, the cells were washed with PBS and labelled for 12–14 hours with [$^{35}$S]-methionine and [$^{35}$S]-cysteine at 200 μCi/ml in cysteine/methionine minus DMEM media. Selected plates of cells were labelled with either [$^{35}$S]-cysteine alone, or [$^{35}$S]-methionine alone in cysteine minus media, or methionine minus media, respectively. The radioactive supernatants were collected and either concentrated 5–10 fold in a Centricon-10 (Amicon) according to manufacturer's instructions or immunoprecipitated along with cell lysates as stated below. One-fifth of each concentrated sample was loaded on a precast 16% Tris-glycine, SDS-PAGE denaturing reducing mini-protein gel (1.5 mm) and electrophoresed according to manufacturer's directions.(Novex). The gels were fixed with Amplify (Amersham) as suggested in the instructions. Fixed, dried gels were exposed to film at −70 degree C. for 8 to 24 hours.

Cell lysates were collected by washing the cells with PBS and lysing with triton lysis buffer. (1% triton, 5 mm HEPES pH 7.2). Cell debris was removed by centrifugation. Lysates and supernatants were immunoprecipitated as follows.

Rabbit anti-NGF and goat anti-hGH antibodies were provided by Immunoassay Services, Genentech, Inc. One half of each supernatant and lysate was immunoprecipitated with rabbit anti-NGF antibodies alone. The other half, serving as a transfection control, was co-immunoprecipitated with the rabbit anti-NGF and goat anti-hGH antibodies.

[$^{35}$S]-labelled supernatants and lysates were preincubated with 100 μL 10% Pansorbin cells (*Staphylococcus aureus*) in phosphate buffered saline (Calbiochem) for 30 to 60 minutes at 4 degrees C. with rotation. Cells were removed by centrifugation and the supernatants were incubated as above with saturating levels of rabbit anti-NGF antibodies or rabbit anti-NGF and goat anti-hGH antibodies. 120 μL 10% Pansorbin cells were added to the mixture and incubated for 1 hour at 4 degrees C. with rotation. Each tube was centrifuged for 2 minutes in a microcentrifuge. Supernatants were removed and the pellets were washed once with Buffer #1 (1M NaCl, 0.05 M Tris pH 6.8 in water), twice with Buffer #2 (1M Tris-pH 8.8, 0.2M NaCl, 1% NP40, 0.3% SDS), and once with cold dH$_2$O. Washed pellets were resuspended in 40 μL 2X Tris-Glycine SDS loading buffer. 20 μL was loaded on a pre-cast 16% Tris-glycine SDS reducing mini-protein gel (1.5 mm) and electrophoresed according to manufacturer's directions.(Novex). The gels were fixed with En$^3$Hance (Dupont) as suggested with the exception that the final wash in water included 5% glycerol to avoid gel cracking.

Fixed, dried gels were exposed to film at −70 degrees C. for 9–66 hours.

Effects of precursor on NGF expression

The effects of the 5' mutations on secreted NGF levels were determined by three hGH controlled experiments performed in duplicate. In these experiments, the hGH controlled for potential differences due to transfection efficiencies. For example, in any one experiment, NGF and hGH expression varied with each plate. Since each NGF expression value was compared only to the hGH expression in the same plate, relative comparisons could be made.

The results of the 5' changed plasmids (pRK5.NGF 5'ACC, pRK5.NT3NGF5'ACC, and pRK5.BDNFNGF 5' ACC) are summarized in Table 5. The chimeric proteins were compared to the wildtype NGF expression level which was set at 100%. Though there seems to be about a 2-fold difference in the levels of NGF production from pRK5.NGF and pRK5.NT3NGF, the production levels from pRK5.BDNFNGF have dropped about 50-fold.

TABLE 5

Effects of Precursor on Expression.

| Plasmid | NGF/hGH | Average | % of NGF Expression |
|---|---|---|---|
| pRK5.NGF5'ACC | 0.194 | 0.258 | 100 |
|  | 0.215 |  |  |
|  | 0.328 |  |  |
|  | 0.286 |  |  |
|  | 0.266 |  |  |
|  | 0.264 |  |  |
| pRK5.NT3NGF5'ACC | 0.105 | 0.147 | 57 |
|  | 0.169 |  |  |
|  | 0.163 |  |  |
|  | 0.149 |  |  |
|  | 0.148 |  |  |
| pRK5.BDNFNGF5'ACC | 0.007 | 0.006 | 2 |
|  | 0.007 |  |  |
|  | 0.006 |  |  |

TABLE 5-continued

Effects of Precursor on Expression.

| Plasmid | NGF/hGH | Average | % of NGF Expression |
|---|---|---|---|
| | 0.006 | | |
| | 0.005 | | |
| | 0.004 | | |

Since it is in its normal form (wildtype), pRK5. NGF5'ACC was given the value of 100%. The two chimeras were then compared as a percentage of this value in the last column.

There are similarities and differences in the amino acid sequences of NGF, NT-3 and BDNF. Most apparently, the mature protein factors are quite homologous (>50%) especially when compared to the precursor portions of each preproprotein. (~20% homology).

Some major differences are observed when comparing the three precursors. First, NGF and NT-3 contain the dibasic pair Lys-Arg at the primary processing site while BDNF contains an Arg-Arg pair. Secondly, only NGF and NT3 contain upstream dibasic sites (Arg-Arg); NGF has two sites whereas NT-3 has only one and BDNF does not have any. Cell culture with proteases Kex2, mPC1, and mP C2

Plasmids pRK5.BDNF and pRK5.NT-3 were transfected as above with the exception that an additional 3 μg of expression plasmid pRK.Kex2, pRK.mPC1, or pRK.mPC2 DNA per plate (100 mm) was added to the transfection mixture. Given the difference in the dibasic cleavage pattern with each precursor, the effects of the enzymes, Kex2, mPC1 and mPC2 on NT-3 and BDNF were examined.

Kex2 cleaved the upstream Arg-Arg site in NT-3, but was unable to process the BDNF upstream region because there is no such site.

mPC1 and mPC2 have no additional effect on the processing of NT-3 or BDNF in the 293 cells.

EXAMPLE 7

Construction of Proinsulin B10 Histidine to Aspartic Acid Mutant and Insulin Expression in Transfected 293 Cells.

The cDNA clone of the human preproinsulin gene, pSVEHIGDHFR, described in Australian patent 616,201 issued Feb. 18, 1992, provided the coding sequence of the human preproinsulin gene for the final mammalian expression vector. A second source of the human preproinsulin gene, pH13 (Sures et al. *Science* 208:57–59 [1980] has also been used in experiments to provide the coding sequence of human proinsulin. Aliquots (5–10 μL) of pSVEHIGDHFR were used for amplification of the coding region by RACE-PCR (rapid amplification of cDNA ends, Frohman 1988; Innis 1990) using a combination of gene-specific PCR primers: for the 5' end they were CAT AAG CTT ACC ATG GCC CTG TGG ATG CGC (SEQ ID NO:55) (sequence given 5' to 3').and for the 3' end they were CAT TCT AGA CTA GTT GCA GTA GTT CTC CAG (SEQ ID NO:56) (sequence given 5' to 3'). All PCR cloning reactions were carried out with Vent DNA polymerase (New England Biolabs) to minimize the introduction of mismatched bases during amplification of template. All proinsulin clones were sequenced with the Sequenase 2.0 kit from USB and cloned into restriction digested pRK5. The final preproinsulin mammalian vector is pRK7.proins.

A human proinsulin mutant having a non-naturally occurring prohormone convertase cleavage site is constructed by mutating the human proinsulin cDNA, pRK.proins, encoding the naturally occurring basic cleavage site at the B-chain/C-peptide junction (KTRR) (SEQ ID NO:20) and A-chain/C-peptide junction (LQKR) (SEQ ID NO:21) by site-directed mutagenesis (Kunkel Supra). The double proinsulin variant, proins.RTKR(SEQ ID NO:22).Ip/RQKR (SEQ ID NO:23).IIp, was constructed. Ip is the Type I enzyme cleavage site and IIp is the Type II enzyme cleavage site. Primers used in construction of the proinsulin mutant, proins.RTKR(SEQ ID NO:22).Ip/RQKR(SEQ ID NO:23) .IIp, are described in example 4. The double proinsulin mutant proins RTKR(SEQ ID NO:22).Ip/RQKR(SEQ ID NO:23).IIp changes the native human proinsulin residue Lys 29 to Arg 29 at the Type I enzyme cleavage site, residue Arg 31 to Lys 31 at the Type I enzyme cleavage site and proinsulin residue Leu 62 is changed to Arg 62 at the Type II enzyme cleavage site. Other proinsulin mutants, proins.RTKR(SEQ ID NO:22),Ip, proins.RQKR(SEQ ID NO:23).IIp, proins.KR.Ip/RQKR(SEQ ID NO:23).IIp, and proins.KTKR(SEQ ID NO:24).Ip were constructed as in example 4. All mutants were screened through the primer regions with the Sequenase 2.0 kit from USB.

Proinsulin, pRK7.proins, and the proinsulin mutant, proins.RTKR(SEQ ID NO:22).Ip/RQKR(SEQ ID NO:23) .IIp, were then mutagenized by the site-directed mutagenesis of Kunkel et al.(*Methods Enzymol.* vol.154, pg. 367–382 [1987]) to yield pRK7.proins.BIOH>D, proinsulin having the histidine at position 10 in the B-chain replaced with an aspartic acid, and the proinsulin mutant, proins.RTKR(SEQ ID NO:22).Ip/RQKR(SEQ ID NO:23).IIp.BIOH>D having the histidine at position 10 in the B-chain replaced with an aspartic acid. The primer used in the Kunkel et al. Supra. method was GC-TTC-CAC-CAG-GTC-GGA-TCC-GCA-CAG-GTG (SEQ ID NO:57), with the sequence given in a 5' to 3' direction. All mutants were screened through the primer regions with the Sequenase 2.0 kit from USB.

DNA from the proinsulin mutants, proins.RTKR(SEQ ID NO:22).Ip/RQKR(SEQ ID NO:23).IIp, proins.RTKR(SEQ ID NO:22).Ip/RQKR(SEQ ID NO:23).IIp.B10H>D, pRK7.proins.B10H>D, and proinsulin, pRK7.proins. was CsCl banded and used for human embryonic kidney cell line 293 (ATCC CRL 1573) transient transfection by the method of Gorman, (Gorman *DNA Prot Eng Tech* 2:3–10, 1990). Cells were labelled as described by Gorman, Supra and cells and lysates were analyzed for insulin-like proteins. Protein-A sepharose immunoprecipitation was performed by the method of Harlow and Lane (from *Antibodies: A Laboratory Manual*, pub. Cold Spring Harbor Laboratory, chapter 11, pp. 421–470 [1988]) on both supernatant and lysate samples using concentrated guinea pig anti-human insulin antibodies (Biomeda I 01). Immunoprecipitation products were resuspended in either 2X Tris-Glycine Sample Buffer (from Novex)/8M urea plus b-mercaptoethanol or 2X Tricine buffer plus b-mercaptoethanol, heated for 5 minutes at 100° C., spun briefly, and run reduced on 18% Tris-glycine SDS or 16% Tricine gels, respectively, according to manufacturer's directions (Novex). The gels were fixed (10% acetic acid, 25% isopropanol, 65% water), and soaked with Amplify (Amersham) as suggested in the instructions. Fixed, dried gels were exposed to film at −70° C. for 1 to 4 days.

DNA from the proinsulin mutants was used for transient transfection by the method of Gorman Supra and twelve to sixteen hours post transfection, the transfection media was replaced with serum free media and secretion products were collected for 36–56 hours. Processed insulin was measured in the collected supernatants by radioimmunoassay (RIA)

using the Equate® RIA INSULIN, kit from Binax, Inc. according to the provided instructions.

To detect the bioactivity and specific activity of proinsulin or mutant proinsulin, secretion products were measured by quantitating the increase in tyrosine phosphorylation of the beta chain of the insulin receptor in 293 cells. 293 cells were plated in 24-well Costar plates in F12-DMEM medium containing serum (10%)(50,000 cells per well) and allowed to attach overnight. Cells were transferred into medium without serum for 8–16 hours. Serum free media was aspirated and cells were stimulated with 1 mL of various concentrations of wildtype bovine insulin (Novo Industri A/S) or mutant insulin from conditioned supernatants. After a 10–15 minute incubation at 37° C., the reaction was stopped by the addition of 100 μL 2X Tris-Glycine sample buffer (from Novex) plus b-mercaptoethanol (50 μl per mL of sample buffer). The samples were vortexed vigorously, heated for 5 minutes at 100° C. and 20 μL was electrophoresed on an 8% Tris-Glycine SDS gel (Novex). After electrophoresis, tyrosine phosphorylation of the b chain of the insulin receptor was detected and quantitated by immunoblotting with anti-phosphotyrosine antibodies followed by scanning densitometry as described by Holmes et al. *Science* 256:1205–1210 [1992]).

NIH 3T3 HIR3.5 cells (Whitaker et al. *PNAS USA*, 84: 5237–5249 [1987]) overexpressing the human insulin receptor were incubated in serum free medium with various concentrations of unlabelled wildtype insulin or insulin mutant and a constant amount of $^{125}$I-labelled Insulin (Amersham) for 16 hours at 4°C. Unbound ligand was removed and cells were washed with ice cold medium. The amount of radioactivity bound was determined after sulubilizing the cells with 0.1 N NaOH containing SDS (0.1%). Relative binding of wildtype insulin and the insulin mutants was determined using a non-linear regression program.

Determination of insulin receptor binding was determined by the following method: Human kidney cells (293) or 3T3 cells overexpressing the human insulin receptor, Whitaker et al. Supra were plated at about 100,000 cell per well dishes.

One to two days after plating, the cells were washed in PBS and starved for 8–16 hours in binding buffer (F12/DMEM (50/50); 2 mM Gln; 10 mM HEPES; 1 mg/ml BSA; penicillin and streptomycin (Gibco 600-5140 Ag 100 units/ml). Cells were placed on ice and washed twice with cold binding buffer. 480 μl of non-radioactive insulin ligand (mutants or standards) in triplicate were placed in each well followed by 20 μl (50,000–100,000 cpm/well) $^{125}$I-labelled insulin (at tyrosine-A14) (Amersham). Cells were incubated at 4° C. for 14–16 hours with gentle rocking. The media was removed and cells were washed twice with cold binding buffer. The amount of radioactivity bound was determined after solubilizing the cells with 0.1N NaOH containing SDS (0.1%). A standard curve was generated using 0 to 1000 nM human insulin standards (USP) or bovine standards (Novo Industri A/S). Relative binding of the insulin mutants was determined using a non-linear binding regression program.

RESULTS
RIA Results In 293

| smpl | dil. | CPM | conc (uU) | construct | ng/mL |
|---|---|---|---|---|---|
| A | 1:5 | 1111 | GTS* | PRK7.proins | — |
| A | 1:10 | 2111 | 1500–3000 | PRK7.proins | >63 |
| A | 1:20 | LOST | 2750 | PRK7.proins | >63 |
| B | 1:5 | LOST | — | PRK7.proins | — |
| B | 1:10 | 2326 | 1500–3000 | PRK7.proins | >63 |
| B | 1:50 | 3589 | 1500 | PRK7.proins | 63 |
| C | 1:2 | 1472 | GTS | pRK7.proins.1* | — |
| C | 1:5 | 2770 | 675 | pRK7.proins.1 | 27 |
| C | 1:10 | 4464 | 600 | pRK7.proins.1 | 27 |
| D | 1:2 | 1405 | GTS | pRK7.proins.1 | — |
| D | 1:5 | LOST | — | pRK7.proins.1 | — |
| D | 1:10 | 4215 | 650 | pRK7.proins.1 | 27 |
| E | 1:10 | LOST | — | pRK7.proins.2* | — |
| E | 1:100 | 2311 | >15,000 | pRK7.proins.2 | >625 |
| E | 1:500 | LOST | — | pRK7.proins.2 | — |
| E | 1:1000 | 6596 | 20,000 | pRK7.proins.2 | 833 |
| F | 1:10 | 495 | GTS | pRK7.proins.2 | — |
| F | 1:100 | 1471 | GTS | pRK7.proins.2 | — |
| F | 1:500 | 5011 | 25,000 | pRK7.proins.2 | 1041 |
| F | 1:1000 | 5552 | 35,000 | pRK7.proins.2 | 1458 |
| G | 1:10 | LOST | — | pRK7.proins.3* | — |
| G | 1:100 | 5548 | 3500 | pRK7.proins.3 | 146 |
| G | 1:500 | 7023 | 5000 | pRK7.proins.3 | 208 |
| G | 1:1000 | 7055 | 8000 | pRK7.proins.3 | 333 |
| H | 1:10 | 2021 | — | pRK7.proins.3 | — |
| H | 1:100 | LOST | — | pRK7.proins.3 | — |
| H | 1:500 | 6828 | 7500 | pRK7.proins.3 | 312 |
| H | 1:1000 | 7255 | 7000 | pRK7.proins.3 | 291 |
| I | no dil | LOST | — | control | — |
| I | 1:5 | LOST | — | control | — |
| J | no dil | LOST | — | control | — |
| J | 1:5 | 7600 | LTS* | control | — |

*pRK7.proins.1 is proins.RTKR.Ip/RQKR.IIp
*pRK7.proins.2 is proins.B10 H>D.
*pRK7.proins.3 is proins.RTKR.Ip/RQKR.IIp.B10H>D.
*GTS is greater than standard
*LTS is less than standard RIA Results In 293

| smpl | dil. | CPM | conc (uU) | construct | ng/ml |
|---|---|---|---|---|---|
| 1 | 1:10 | 1200 | 3000 | PRK7.proins | 125 |
| i | 1:50 | 2750 | 2750 | PRK7.proins | 115 |
| 2 | 1:10 | lost | — | PRK7.proins | — |
| 2 | 1:50 | lost | — | PRK7.proins | — |
| 3 | no dil | 1522 | 145 | PRK7.proins.1* | 6 |
| 3 | 1:3 | 2668 | 180 | PRK7.proins.1 | 7.5 |
| 3 | 1:6 | lost | — | PRK7.proins.1 | — |
| 4 | no dil | 1581 | 135 | PRK7.proins.1 | 5 |
| 4 | 1:3 | 2951 | 156 | PRK7.proins.1 | 6.5 |
| 4 | 1:6 | 4046 | 210? | PRK7.proins.1 | 8.7 |
| 5 | 1:10 | 542 | GTS* | PRK7.proins.2* | — |
| 5 | 1:50 | 1327 | 13,500 | PRK7.proins.2 | 560 |
| 5 | 1:100 | 1582 | 20,000 | PRK7.proins.2 | 833 |
| 6 | 1:10 | 667 | GTS | PRK7.proins.2 | — |
| 6 | 1:50 | 1448 | 12,500 | PRK7.proins.2 | 520 |
| 6 | 1:100 | 1470 | 22,000 | PRK7.proins.2 | 916 |
| 7 | 1:10 | 366 | GTS | PRK7.proins.3* | — |
| 7 | 1:50 | 876 | GTS | PRK7.proins.3 | — |
| 7 | 1:100 | 1176 | GTS | PRK7.proins.3 | >1125 |
| 8 | 1:10 | 467 | GTS | PRK7.proins.3 | — |
| 8 | 1:50 | 931 | GTS | PRK7.proins.3 | — |
| 8 | 1:100 | 1038 | GTS | PRK7.proins.3 | >1125 |
| 9 | no dil | 713 | GTS | PRK7.proins.4* | — |
| 9 | 1:3 | 927 | GTS | PRK7.proins.4 | — |
| 9 | 1:6 | 1475 | 840 | PRK7.proins.4 | 35 |
| 10 | no dil | 416 | GTS | PRK7.proins.4 | — |
| 10 | 1:3 | 1079 | GTS | PRK7.proins.4 | — |
| 10 | 1:6 | 1435 | 840 | PRK7.proins.4 | 35 |
| 11 | no dil | 1297 | 245 | PRK7.proins.5* | 10–11 |
| 11 | 1:3 | 2686 | 195 | PRK7.proins.5 | 10–11 |

-continued

RIA Results In 293

| smpl | dil. | CPM | conc (uU) | construct | ng/ml |
| --- | --- | --- | --- | --- | --- |
| 11 | 1:6 | 3615 | 270 | PRK7.proins.5 | 10–11 |
| 12 | no dil | lost | — | PRK7.proins.5 | 10–11 |
| 12 | 1:3 | 1486 | 435 | PRK7.proins.5 | 10–11 |
| 12 | 1:6 | 3807 | 270 | PRK7.proins.5 | 10–11 |
| 13 | no dil | 840 | GTS | PRK7.proins.6* | — |
| 13 | 1:3 | 776 | GTS | PRK7.proins.6 | — |
| 13 | 1:6 | 2468 | 420 | PRK7.proins.6 | 17.5 |
| 14 | no dil | 740 | GTS | PRK7.proins.6 | — |
| 14 | 1:3 | 1217 | — | PRK7.proins.6 | — |
| 14 | 1:6 | 2368 | 420 | PRK7.proins.6 | 17.5 |
| 15 | 1:5 | 931 | GTS | PRK7.proins.7* | — |
| 15 | 1:10 | 1672 | 2100 | PRK7.proins.7 | 8.8 |
| 16 | all | 5800 | LTS* | control | 0 |

*PRK7.proins.1 is proins.RTKR.Ip/RQKR.IIp
*PRK7.proins.2 is proins.B10 H>D.
*PRK7.proins.3 is proins.RTKR.Ip/RQKR.IIp.B10 H>D.
*PRK7.proins.4 is proins.RTKR.Ip
*PRK7.proins.5 is proins.RQKR.IIp
*PRK7.proins.6 is proins.KR.Ip/RQKR.IIp
*PRK7.proins.7 is proins.KTKR.Ip
*GTS is greater than standard
*LTS is less than standard Expression of proinsulin Following transfection with an expression vector carrying the wildtype proinsulin cDNA, 293 HEK cells synthesize and secrete uncleaved proinsulin with a molecular weight of 6.5 kD. Unprocessed, [$^{35}$S]-labelled proinsulin is immunoprecipitated from both the cell lysate and the media using an insulin specific antibody. The unprocessed material migrates with the 6.5 kD molecular marker. Mature insulin, when reduced, migrates similarly to the A and B chains at 2.35 and 3.4 kD when compared to the two bands of the molecular weight protein standards.

Expression of Proinsulin Mutants

Proins.RTKR.Ip/RQKR.IIp is processed into products that co-migrate with the A and B chains of insulin as well as processing intermediates. When proins.RTKR.Ip or proins.RQKR.IIp, representing a mutant cleavage site at the B-/C-chain junction or the A-/C-chain junction respectively, are transfected, only one of the mature chains was detected along with intermediates. When the mutant cleavage site is at the A-/C-chain junction, the A chain is detected along with a slower migrating band consistent with the B-C intermediate. When the mutant cleavage site is at the B-/C-chain junction, the B chain is detected along with a faster migrating band consistent with the A-C intermediate. Intermediates disappear when the amount of 293 homologous-cell enzyme that recognizes the mutant cleavage sites is increased by cotransfection with an expression vector expressing the 293 homologous-cell enzyme. Proins.KTKR.Ip was resistant to cleavage by the 293 cell enzyme.

Detection of Bioactivity

When mature, active insulin binds to the A-chain of the insulin receptor outside the cell, tyrosine residues on the B-chain of the insulin receptor are autophosphorylated (Kasuga et al., *Science*, 215:185–186 [1982]) Therefore, insulin bioactivity was assayed by measuring the ability of the B-chain of the insulin receptor to become autophosphorylated. Phosphorylation of the B-chain can be visually observed on an immunoblot. Upon stimulation with increasing concentrations of bovine insulin, the B-chain is increasingly observed at a mass of 96 kD by probing with antiphosphotyrosine antibodies. A similar increase in B-chain phosphorylation is detected by stimulation with various concentrations of the insulin mutants, proins.RTKR.Ip/RQKR.IIp and proins.RTKR.Ip/RQKR.IIp.B10 H>D.

Relative Specific Activity and Insulin Binding Studies

Relative specific activity was determined by quantitating the amount of phosphorylation stimulated by each insulin mutant compared to insulin standards. Both the proins.RTKR.Ip/RQKR.IIp and proins.RTKR.Ip/RQKR.IIp.B10 H>D have similar activity to the bovine insulin standards within experimental error. Insulin receptor binding studies indicated similar binding affinities to the wildtype insulin standards with both the proins.RTKR.Ip/RQKR.IIp and proins.RTKR.Ip/RQKR.IIp.B10 H>D insulin mutants.

B10 H>D Insulin Mutants

The relative amount of secretion products detected from proins.RTKR.Ip/RQKR.IIp.B10 H>D is greatly increased as compared to proins.RTKR.Ip/RQKR.IIp which lacks the B10 His to Asp change. When quantitated by RIA, the increase in the amount of processed insulin ranges from 10–40 fold depending on transfection efficiency. In addition to an increase in the accumulation of active insulin due to proins.RTKR.Ip/RQKR.IIp.B10 H>D, there is an increase in the accumulation of processing intermediates with the B10H>D mutant in the wildtype proinsulin background. Transfection with wildtype proinsulin does not yield insulin A and B chains; however, transfection with proin.B10H>D does yield detectable insulin A and B chain.

The proins.RTKR.Ip/RQKR.IIpB10 H>D and proins.RTKR.Ip/RQKR.IIp have the same specific activity as measured by B-chain phosphorylation and the same capacity for binding to the insulin receptor. The B10H>D mutation appears to be more resistant to intracellular proteases as well whether this mutation occurs in the wildtype proinsulin or within the proins.RTKR.Ip/RQKR.IIp mutation.

EXAMPLE 8

The following example illustrates the use of host cells, mouse myoblasts, comprised of DNA encoding a proinsulin mutant and a glucose response element in gene therapy. The use of muscle myoblasts in gene therapy is described in WO 90/15863, published Dec. 27, 1990.

Construction of a retroviral vector

The general procedure for plasmid construction and DNA preparation are as described by Maniatis, et al. (*Molecular Cloning: A Laboratory Manual,* Cold Spring Harbor Laboratory, Cold Spring Harbor, N.Y., USA [1982]).

To construct the retroviral vector used to genetically engineer mouse myoblasts to produce proinsulin in response to glucose, cDNA encoding proin.RTKR.Ip/RQKR.IIp or proin.RTKR.Ip/RQKR.IIP B10H>D and the activating sequence of the glucose response element (between −2080 and −3200 bp) of the L-type pyruvate kinase (Cuif et al., Supra and Tani et al., *Biohem.Biophys.Res.Commun.* vol. 143, pg.431–438 [1987]) are placed into the pB2 retroviral vector (laboratory of Molecular Hematology, NIH). The pB2 viral vector construction is described in WO 90/131, pg. 9–10, published Jun. 28, 1990. The resultant retroviral vector, pRV.proin.RTKR.Ip/RQKR.IIp or pRV.proin.RTKR.Ip/RQKR.IIp B10H>D further comprises the SV40-neomycin resistance fragment for purposes of selection. The ligation of the SV40-neomycin resistance fragment into the pB2 vector is described in WO 90/06997, published Jun. 28, 1990.

Host cells of the present invention not comprised of naturally occurring nucleic acid encoding a functional facilitative glucose transporter (GLUT) and glucokinase, will further comprise non-naturally occurring nucleic acid encoding a GLUT, preferably GLUT 2 or GLUT 4, and glucokinase.

The host cell may further be comprised of non-naturally occurring nucleic acid encoding a host cell processing enzyme.

The recombinant retroviral vectors pRV.proin.RTKR.Ip/RQKR.IIP or pRV.proin.RTKR.Ip/RQKR.IIP B10H>D are each separately transfected into retroviral vector packaging cell lines, either the amphotropic packaging lines, PA12 (Science vol. 225:630 [1984]), the PA317 line (*Mol. Cell. Biol.* vol.6 pg. 2895 [1986]), or the φ-CRIP packaging cell line that produces replication-incompetent virus with an amphotropic host range, allowing infection of mouse and human cell lines that are recombination resistant (Dhawan, et al., *Science* vol. 254 pg 1509–1512 [1991]). Supernatant from the retroviral producer cells is collected, filtered and concentrated by centrifugation.

Cells of the C2C12 mouse myogenic line (Yaffe et al., *Nature* vol. 270, pg. 725 [1977] and Blau et al., *Science* vol. 230, pg. 758 [1985]) are infected with a retroviral proinsulin construct.

The highest producing proinsulin myoblast cells are selected for injection into the hind limbs of the transgenic mouse model for insulin dependent diabetes Stewart et al., from *Cytokine Interactions and Their Control. Proceedings of the First Jenner Symposium* ed.Baxter et al., pub. John Wiley and Sons, New York pg. 93–104 [1991].

References

Barr P J Mammalian subtilisins: the Long-sought dibasic processing endoproteases. Cell 66:1–3 (1991)

Barr P J, Mason O B, Landsberg K E, Wong P A, Kiefer M C, Brake A J cDNA and gene structure for a human subtilisin-like protease with cleavage specificity for paired basic amino acid residues. DNA Cell Biol 10:319–328 (1991)

Bathurst I C, Brennan S O, Carrell R W, Cousens L S, Brake A J, Barr P J yeast KEX2 protease has the properties of a human proalbumin converting enzyme. Science 235:348–350 (1986)

Benjannet S, Rondeau N, Day R, Chrétien M, Seidah N G PC1 and PC2 are proprotein convertases capable of cleaving proopiomelanocortin at distinct pairs of basic residues. Proc Natl Acad Sci USA 88:3564–3568 (1991)

Brennan S O, Peach R J, Bathurst I C Specificity of yeast kex2 protease for variant human proalbumins is identical to the in vivo specificity of the hepatic proalbumin convertase. J Biol Chem 265:21494–21497 (1990)

Bresnahan P A, Leduc R, Thomas L, Thorner J, Gibson H L, Brake A J, Barr P J, Thomas G Human fur gene encodes a yeast kex2-like endoprotease that cleaves pro-b-NGF in vivo. J Cell Biol 111:2851–2859 (1990)

Chung K-N, Walter P, Aponte G W, Moore H-PH Molecular sorting in the secretory pathway. Science 243:192–197 (1989)

Davidson H W, Rhodes C J, Hutton J C Intraorganellar calcium and pH control proinsulin cleavage in the pancreatic b cell via two distinct site-specific endopeptidases. Nature 333:93–96 (1988)

Docherty K, Steiner D F Post-translational proteolysis in polypeptide hormone biosynthesis. Annu Rev Physiol 44:625–638 (1982)

Douglass J, Civelli O, Herbert E Polyprotein gene expression: Generation of diversity of neuroendocrine peptides. Annu Rev Biochem 53:665–715 (1984)

Foster D C, Holly R D, Sprecher C A, Walker K M, Kumar A A Endoproteolytic processing of the human protein C precursor by the yeast kex2 endopeptidase coexpressed in mammalian cells. Biochemistry 30:367–372 (1991)

Fricker L D, Das B, Angeletti R H Identification of the pH-dependent membrane anchor of carboxypeptidase E. J Biol Chem 265:2476–2482 (1990)

Frohman M A, Dish M K, Martin G R Rapid production of full-length cDNAs from rare transcripts: amplification using a single gene-specific oligonucleotide primer. Proc Natl Acad Sci USA 85:8998–9002 (1988)

Fuller R S, Brake A, Thorner J Yeast prohormone processing enzyme (KEX2 gene product) is a $Ca^{2+}$-dependent serine protease. Proc Natl Acad Sci USA 86:1434–1438 (1989)

Fuller R S, Brake A J, Thorner J Intracellular targeting and structural conservation of a prohormone-processing endoprotease. Science 246:482–486 (1989)

Germain D, Zollinger L, Racine C, Gossard F, Dignard D, Thomas D Y, Crine P, Boileau G The yeast kex2 -processing endoprotease is active in the Golgi apparatus of transfected NIH 3T3 fibroblasts. Mol Endocrinol 4:1572–1579 (1990)

Girgis S I, Alevizaki M, Denny P, Ferrier G J M, Legon S Generation of DNA probes for peptides with highly degenerate codons using mixed primer PCR, Nucleic Acids Res 16:10371 (1988)

Gorman C M, Gies D, McCray G, Huang M The human cytomegalovirus major immediate early promoter can be transactivated by adenovirus early proteins. Virology 171:377–385 (1989)

Gorman C M, Gies D R, McCray G Transient production of proteins using an adenovirus transformed cell line. DNA Prot Eng Tech 2:3–10 (1990)

Gumbinger B, Kelly R B Two distinct intracellular pathways transport secretory and membrane glycoproteins to the surface of pituitary tumour cells. Cell 28:51–59 (1982)

Hansell D J, Bryant-Greenwood G D, Greenwood F C Expression of the human relaxin H1 gene in the decidua, trophoblast and prostate. J Clin Endocrinol Metabol 72:899–904 (1991)

Hatsuzawa K, Hosaka M, Nakagawa T, Nagase M, Shoda A, Murakami K, Nakayama K Structure and expression of mouse furin, a yeast Kex2-related protease. J Biol Chem 265:22075–22078 (1990)

Hudson P, John M, Crawford R, Haralambidis J, Scanlon D, Gorman J, Tregear G, Shine J, Niall H 1984 Relaxin gene expression in human ovaries and the predicted structure of a human preprorelaxin by analysis of cDNA clones. EMBO J 3:2333–2339

Innis M A, Gelfand D H, Sninsky J J, White T J PCR Protocols—A guide to Methods and Applications. Academic Press Inc., San Diego, Calif. (1990)

Julius D, Blair L, Brake A, Sprague G, Thorner J Yeast a factor is processed from a larger precursor polypeptide: the essential role of a membrane-bound dipeptidyl aminopeptidase. Cell 32:839–852 (1983)

Julius D, Brake A, Blair L, Kunisawa R, Thorner J Isolation of the putative structural gene for the lysine-arginine-cleaving endopeptidase required for processing of yeast prepro-a-factor. Cell 37:1075–1089 (1984)

Kunkel T A, Roberts J D, Zakour R A Rapid and efficient site-specific mutagenesis without phenotypic selection. Methods Enzymol 154:367–382 (1987)

Lee C C, Wu X, Gibbs R A, Cook R G, Muzny D M, Caskey C T Generation of cDNA probes directed by amino acid sequence: cloning of urate oxidase. Science 239:1288–1291 (1988)

Loh Y P, Brownstein M J, Gainer H Proteolysis in neuropeptide processing and other neural functions. Annu Rev Neurosci 7:189–222 (1984)

Mains R E, Dickerson I M, May V, Stoffers D A, Perkins S N, Ouafik L H, Husten E J, Eipper B A Cellular and molecular aspects of peptide hormone biosynthesis. Front Neuroendocrinol 11:52–89 (1990)

Maniatis T, Fritch E F, Sambrook J Molecular Cloning—A Laboratory Manual, ed 3. Cold Spring Harbor Laboratory, Cold Spring Harbor (1982)

Moore H-P, Gumbinger B, Kelly R B Chloroquine diverts ACTH from a regulated to a constitutive pathway in AtT-20 cells. Nature 302:434–436 (1983)

Nishi M, Chan C J, Naganatus S, Bell G I, Steiner D F Conservation of the sequence of islet amyloid polypeptide in five mammals is consistent with its putative role as an islet hormone. Proc Natl Acad Sci USA 86:5738–5742 (1989)

Redding K, Holcomb C, Fuller R S Immunolocalisation of kex2 protease identifies a putative late Golgi compartment in the yeast *Saccharomyces cerevisiae*. J Cell Biol 113:527–538 (1991)

Seidah N G, Gaspar L, Mion P, Marcinkiewicz M, Mbikay M, Chrétien M cDNA sequence of two distinct pituitary proteins homologous to kex2 and furin gene products: tissue-specific mRNAs encoding candidates for prohormone processing proteinases.DNA and Cell Biol 9:415–424 (1990)

Seidah N G, Marcinkiewicz M, Benjannet S, Gaspar L, Beaubien G, Mattei M G, Lazure C, Mbikay M, Chrétien M Cloning and primary sequence of a mouse candidate prohormone convertase PC1 homologous to PC2, furin, and kex2: distinct chromosomal localization and messenger RNA distribution in brain and pituitary compared to PC2. Mol Endocrinol 5:111–122 (1991)

Sherwood O D Relaxin. In: Knobil E, Neill J (eds) The Physiology of Reproduction. Raven Press, New York, pp 585–673 (1988)

Smeekens S P, Avruch A S, LaMendola J, Chan S J, Steiner D F Identification of a cDNA encoding a second putative prohormone convertase related to PC2 in AtT-20 cells and islets of Langerhans. Proc Natl Acad Sci USA 88:340–344 (1991)

Smeekens S P, Steiner D F Identification of a human insulinoma cDNA encoding a novel mammalian protein structurally related to the yeast dibasic processing protease kex2. J Biol Chem 265:2997–3000 (1990)

Stults J T, Bourell J H, Canova-Davis E, Ling V T, Laramee G R, Winslow J W, Griffin P R, Rinderknecht E, Vandlen R L Structural Characterization by mass spectrometry of native and recombinant human relaxin. Biomed Environ Mass Spectrom 19:655–664 (1991)

Thomas G, Thorne B A, Thomas L, Allen R G, Hruby D E, Fuller R, Thorner J Yeast KEX2 endopeptidase correctly cleaves a neuroendocrine prohormone in mammalian cells. Science 241:226–230 (1988)

Thomas L, Leduc R, Thorne B, Smeekens S P, Steiner D F, Thomas G Kex2-like endoproteases PC2 and PC3 accurately cleave a model prohormone in mammalian cells: evidence for a common core of neuroendocrine processing enzymes.Proc Natl Acad Sci USA 88:5297–5301 (1991)

Van den Ven J M, Voorberg J, Fontijn R, Pannekoek H, van den Ouweland A M V, van Duijnhoven H L P, Roebroek A J M, Siezen R J Furin is a subtilisin-like proprotein processing enzyme in higher eukaryotes. Molec Biol Reports 14:265–275 (1990)

Wise R J, Barr P J, Wong P A, Kiefer M C, Brake A J, Kaufman R J Expression of a human proprotein processing enzyme: correct cleavage of the von Willebrand factor precursor at a paired basic amino acid site. Proc Natl Acad Sci USA 87:9378–9382 (1990)

Zollinger L, Racine C, Crine P, Boileau G, Germain D, Thomas D Y, Gossard F, Intracellular proteolytic processing of proopiomelanocortin in heterologous COS-1 cells by the yeast KEX2 endoprotease. Biochem Cell Biol 68:635–640 (1990)

Angeletti, R. H.; Hermodson, M. A.; Bradshaw, R. A. Amino acid sequences of mouse 2.5S nerve growth factor. II. Isolation and characterization of the thermolytic and peptic peptides and the complete covalent structure. Biochemistry 12:100–115 (1973).

Bathurst, I. C.; Brennan, S. O.; Carrell, R. W.; Cousens, L. S.; Brake, A. J.; Barr, P. J. Yeast KEX2 protease has the properties of a human proalbumin converting enzyme. Science 235:348–350 (1987).

Benjannet, S.; Rondeau, N.: Day, R.; Chretien, M.; Seidah, N. PC1 and PC2 are proprotein convertases capable of cleaving proopiomelanocortin at distinct pairs of basic residues. Proc. Natl. Acad. Sci. USA 88:3564–3568 (1991)

Bennett, H. P. J. Biosynthetic fate of the amino-terminal fragment of pro-opiomelanocortin within the intermediate lobe of the mouse pituitary. Peptides 7:615–622 (1987)

Benore-Parsons, M.; Seidah, N. G.; Wennogle, L. P. Substrate phosphorylation can inhibit proteolysis by trypsin-like enzymes. Arch. Biochem. Biophys. 272:274–280 (1989)

Berger, E. A.; Shooter, E. M. Evidence for pro-b-nerve growth factor, a biosynthetic precursor to b-nerve growth factor. Proc. Natl. Acad. Sci. USA 74:3647–3651 (1977)

Bresnahan, P. A.; Leduc, R.; Thomas, L.; Thorner, J.; Gibson, H. L.; Brake, A. J.; Barr, P. J.; Thomas, G. Human fur gene encodes a yeast Kex2-like endoprotease that cleaves pro b-NGF in vivo. J. Cell Biol. 111:2851–2859 (1990)

Cohen, S. Purification of a nerve-growth promoting protein from the mouse salivary gland and its neuro-cytotoxic antiserum. Proc. Natl. Acad. Sci. USA 46:302–311 (1960)

Dickerson, I. M.; Mains, R. E. Cell-type specific post-translational processing of peptides by different pituitary cell lines. Endocrinology 127:133–140 (1990).

Docherty, K.; Steiner D. F. Post-translational proteolysis of polypeptide hormone biosynthesis. Annu. Rev. Physiol. 44:625–638 (1982).

Douglass, J.; Civelli, O.; Herbert, E. Polyprotein gene expression: generation of diversity of neuroendocrine peptides. Ann. Rev. Biochem. 53:665–715 (1984)

Ernfors, P.; Ibañez, C. F.; Ebendal, T.; Olson, L.; Persson, H. Molecular cloning and neurotrophic activities of a protein with structural similarities to nerve growth factor: developmental and topographical expression in the brain. Proc. Natl. Acad. Sci. USA 87:5454–5458 (1990)

Fuller, R. S.; Brake, A. J.; Thorner, J. Intracellular targeting and structural conservation of a prohormone-processing endoprotease. Science 246:482–486; 1989.

Furie, B.; Furie, B. C. The molecular basis of blood coagulation. Cell 53:505–518 (1988).

Germain, D.; Zollingert, L.; Racine, C.; Gossard, F.; Dignard, D.; Thomas, D. Y.; Crine, P.; Boileau, G. The yeast KEX-2-processing endoprotease is active in the Golgi apparatus of transfected NIH 3T3 fibroblasts. Mol. Endo. 4:1572–1579 (1990)

Gorin, P. D.; Johnson, E. M. Experimental autoimmune mode of nerve growth factor deprivation: effects on developing peripheral sympathetic and sensory nerves. Proc. Natl. Acad. Sci. USA 76:5382–5386 (1979).

Gorman, C. M.; Gies, D. R.; McCray, G. Transient production of proteins using an adenovirus transformed cell line. DNA and Prot. Eng.Tech. 2:3–10 (1990)

Gray, A. M.; Mason, A. J. Requirement for activin A and transforming growth factor-b 1 pro-regions in homodimer assembly. Science 247:1328–1330 (1990).

Gross, D. J.; Vill-Komaroff, L.; Kahn, C. R.; Weir, G. C.; Halban, P. A. Deletion of a highly conserved tetrapeptide sequence of the proinsulin connecting peptide (C-peptide) inhibits proinsulin to insulin conversion by transfected pituitary corticotroph (AtT20) cells. J. Biol. Chem. 264:21486–21490 (1989).

Hamburger, V. The journey of a neuroembryologist. Annu. Rev. Neurosci. 12:1–12; 1989.

Hatsuzawa, K.; Hosaka, M.; Nakagawa, T.; Nagase, M.; Shoda, A.; Murakami, K.; Nakayama, K. Structure and expression of mouse furin, a yeast Kex-2-related protease. J. of Biol. Chem. 265:22075–22078 (1990).

Hohn, A.; Leibrock, J.; Bailey, K.; Barde Y. Identification and characterization of a novel member of the nerve growth factor/brain-derived neurotrophic factor family. Nature 344:339–341 (1990)

Jones, K. R.; Reichardt, L. F. Molecular cloning of a human gene that is a member of the nerve growth factor family. Proc. Natl. Acad. Sci. USA 87:8060–8064 (1990).

Julius, D.; Brake, A.; Blair, L.; Kunisawa, R.; Thorner, J. Isolation of the putative structural gene for the lysine-arginine-cleaving endopeptidase required for processing of yeast prepro-a-factor. Cell 37:1075–1089 (1984).

Kozak, M. Point mutations define a sequence flanking the AUG initiator codon that modulates translation by eukaryotic ribosomes. Cell 44:283–292 (1986)

Lazure, C.; Seidah, N. C.; Pelaprat, D.; Chretien, M. Proteases and posttranslational processing of prohormones: a review. Can. J. Cell. Biol. 61:501–515 (1983).

Leibrock, J.; Lottspeich, F.; Hohn, A.; Hofer, M.; Hengerer, B.; Masiakowski, P.; Thoenen H.; Barde, Y. Molecular cloning and expression of brain-derived neurotrophic factor. Nature 341:149–152 (1989).

Levi-Montalcini, R.; Booker B. Destruction of the sympathetic ganglia in mammals by an antiserum to the nerve growth factor protein. Proc. Natl. Acad. Sci. USA 46:384–390 (1960)

Liu, C.; Simonsen, C. C.; Levinson, A. D. Initiation of translation at internal AUG codons in mammalian cells. Nature 309:82–85 (1984)

Mains, R. E.; Dickerson, I. M.; May, V.; Stoffers, D. A.; Perkins, S. N.; Ouafic, L.; Husten, E. J.; Eipper, B. Cellular and molecular aspects of peptide hormone biosynthesis. Front Neuroendocrinol. 11:52–89 (1990)

Maisonpierre, P. C.; Belluscio, L.; Friedman, B.; Alderson, R. F.; Wiegand, S. J.; Furth, M. E.; Lindsay, R. M.; Yancopoulos, G. D. NT-3, BDNF, and NGF in the developing rat nervous system: parallel as well as reciprocal patterns of expression. Neuron 5:501–509 (1990b).

Maisonpierre, P. C.; Belluscio, L.; Squinto, S.; Ip, N. Y.; Furth, M. E.; Lindsay, R. M.; Yancopoulos, G. D. Neurotrophin-3: a neurotrophic factor related to NGF and BDNF. Science 247:1446–1451 (1990a).

Maniatis, T.; Fritsch, E. F.; Sambrook, J. Molecular cloning—a laboratory manual. Cold Spring Harbor: Cold Spring Harbor Laboratory Press; 1982)

Mullis, K.; Faloona, F.; Scharf, S.; Saiki, R.; Horn, G.; Erlich, H. Specific enzymatic amplification of DNA in vitro: the polymerase chain reaction. Cold Spring Harbor Symp. Quant. Biol. 51:335–350 (1986).

Pan, L. C.; Price, P. A. The propeptide of rat bone g-carboxyglutamic acid protein shares homology with other vitamin K-dependent protein precursors. Proc. Natl. Acad. Sci. USA 82:6109–6113 (1985).

Powell, S. K.; Orci, L.; Craik, C. S.; Moore, H. H. Efficient targeting to storage granules of human proinsulins with altered propeptide domain. J. Cell Biol. 106:1843–185 (1988)

Rice, C. M.; Aebersold, R.; Teplow, D. B.; Pata, J.; Bell, J. R.; Vorndan, A. V.; Trent, D. W.; Brandriss, M. W.; Schlesinger, J. J.; Strauss, J. H. Partial n-terminal amino acid sequences of three nonstructural proteins of two flaviviruses. Virology 151:1–9 (1986).

Rice, C. M.; Lenches, E. M.; Eddy, S. R.; Shin, S. J.; Sheets, R. J.; Strauss, J. H. Nucleotide sequence of yelow fever virus: implications for flavivirus gene expression and evolution. Science 229:726–733 (1985)

Rosenthal, A.; Goeddel, D. V.; Nguyen, T.; Lewis, M.; Shih, A.; Laramee, G. R.; Nikolics, K.; Winslow J. W. Primary structure and biological activity of a novel human neurotrophic factor. Neuron 4:767–773 (1990).

Saiki, R. K.; Sccharf, S.; Faloona, F.; Mullis, K. B.; Horn, G. T.; Erlich, H. A.; Arnheim, N. Enzymatic amplification of b-globin genomic sequences and restriction site analysis for diagnosis of Sickle Cell Anemia. Science 230:1350–1354 (1985).

Sambrook, J.; Fritsch, E. F.; Maniatis, T. Molecular cloning—a laboratory manual. 2nd ed. Cold Spring Harbor: Cold Spring Harbor Laboratory Press (1989).

Scott, J.; Selby, M.; Urdea, M.; Quiroga, M; Bell, G. I.; Rutter, W. J. Isolation and nucleotide sequence of a cDNA encoding the precursor of mouse nerve growth factor. Nature 302:538–540 (1983)

Seidah, N. G.; Gaspar, L.; Mion, P.; Marcinkiewicz, M.; Mbikay, M.; Chrétien, M. cDNA sequence of two distinct pituitary proteins homologous to Kex2 and furin gene products: Tissue-specific mRNAs encoding candidates for prohormone processing proteinases. DNA and Cell Biol. 9:415–424 (1990)

Seidah, N. G.; Marcinkiewicz, M.; Benjannet, S.; Gaspar, L.; Beaubien, G.; Mattei, M. G.; Lazure, C.; Mbikay, M.; Chrétien, M. Cloning and primary sequence of a mouse candidate prohormone convertase PC1 homologous to PC2, furin, and Kex2: Distinct chromosomal localization and messenger RNA distribution in brain and pituitary compared to PC2. Mol. Endo. 5:111–122 (1991).

Selby, M. J.; Edwards, R. H.; Rutter, W. J. Cobra nerve growth factor: structure and evolutionary comparison. J. Neurosci. Res. 18:293–298 (1987)

Sevarino, K. A.; Stork, P.; Ventimiglia, R.; Mandel, G.; Goodman, R. H. Amino-terminal sequences of prosomatostatin direct intracellular targeting but not processing specificity. Cell 57:11–19 (1989).

Smeekens, S. P.; Avruch, A. S.; LaMendola, J.; Chan, S. J.; Steiner, D. F. Identification of a cDNA encoding a second putative prohormone convertase related to PC2 in AtT20 cells and islets of Langerhans. Proc. Natl. Acad. Sci. USA 88:340–344 (1991).

Snider, W. D.; Johnson, E. M. Neurotrophic molecules. Ann. Neurol. 26:489–506 (1989).

Steiner, D. F. Proteolytic processing of secretory proteins. Schmitt, F. O.; Bird, S. J.; Bloom, F. E., eds. Molecular Genetic Neuroscience. New York: Raven Press; 149–160 (1982).

Thomas G.; Thorne, B. A.; Thomas, L.; Allen, R. G.; Hruby, D. E.; Fuller, R.; Thorner, J. Yeast KEX2 endopeptidase correctly cleaves a neuroendocrine prohormone in mammalian cells. Science 241:226–241 (1988).

Thomas, G.; Thorne, B. A.; Thomas, L.; Allen, R. G.; Hruby, D. E.; Fuller, R.; Thorner, J. Yeast KEX2 endopeptidase correctly cleaves a neuroendocrine prohormone in mammalian cells. Science 241:226–230 (1988).

Thomas, L.; LeDuc, R.; Thorne, B.; Smeekens, S.; Steiner, D; Thomas, G. Kex2-like endoproteases PC2 and PC3 accurately cleave a model prohormone in mammalian cells: Evidence for a common core of neuroendocrine processing enzymes. Proc. natl. Acad. Sci. USA 88:5297–5301 (1991).

Thorne, B. A.; Thomas, G. An in vivo characterization of the cleavage site specificity of the insulin cell prohormone processing enzymes. J. Biol. Chem. 265:8436–8443 (1990).

Van den Ouweland, A. M. W.; Van Duijnhoven, H. L. P.; Keizer, G. D.; Dorssers, L. C. J.; Van de Ven, W. J. M. Structural homology between the human fur gene product and the subtilisin-like protease encoded by yeast KEX2. Nucleic Acids Res. 18:664 (1990).

Wise, R. J.; Pittman, D. D.; Handin, R. I.; Kaufman, R. J.; Orkin, S. H. The propeptide of von Willebrand factor independently mediates the assemble of von Willebrand multimers. Cell 52:229–236 (1988).

Yoshimasa, Y.; Paul, J. I.; Whittaker, J.; Steiner, D. F. Effects of amino acid replacements within the tetrabasic cleavage site on the processing of the human insulin receptor precursor expressed in Chinese hamster ovary cells. J. Biol. Chem. 265:17230–17237.(1990)

We claim:

1. An engineered animal host cell that is not naturally capable of forming secretory granules, comprising a nucleic acid encoding a glucose transporter protein, a nucleic acid encoding a glucokinase, and a nucleic acid encoding a variant proinsulin, the variant proinsulin having a non-naturally occurring cleavage site, the cleavage site being recognizable by an engineered host cell processing enzyme that cleaves the variant proinsulin at the non-naturally occurring cleavage site to produce an active insulin in the host cell.

2. The engineered host cell of claim 1 wherein said engineered host cell processing enzyme is furin.

3. The engineered host cell of claim 1 wherein said host cell is a muscle myoblast cell.

4. The engineered host cell of claim 1 wherein said nucleic acid encoding said variant proinsulin is methylated.

5. A method for culturing an animal host cell capable of producing insulin from variant proinsulin, comprising culturing an animal host cell not naturally capable of forming secretory granules, said host cell comprising nucleic acid encoding a variant proinsulin having a non-naturally occurring cleavage site, said cleavage site being recognizable by a host cell processing enzyme, under conditions wherein the variant proinsulin is expressed and cleaved at the non-naturally occurring cleavage site by the host cell processing enzyme to produce an active insulin in the host cell.

6. A method for culturing an insulin-dependent animal host cell, comprising culturing an animal host cell that is dependent on insulin and that is not naturally capable of forming secretory granules, wherein the host cell comprises a nucleic acid encoding a variant proinsulin, wherein the variant proinsulin contains a non-naturally occurring cleavage site, and wherein the non-naturally occurring cleavage site is recognizable by a first enzyme in the host cell, under conditions in a cell culture wherein the variant proinsulin is expressed and cleaved at the non-naturally occurring cleavage site by the first enzyme, thereby producing an active insulin.

7. The method of claim 6, wherein the cleavage site recognizable by the first enzyme is a prohormone convertase cleavage site.

8. The method of claim 7, wherein the prohormone convertase cleavage site is ZXZR (SEQ ID NO:47), wherein Z is LYS or ARG; X is any amino acid; and R is ARG.

9. The method of claim 6 wherein the host cell is mammalian.

10. The method of claim 9 wherein the host cell is a chinese hamster ovary cell.

11. The method of claim 6 further comprising introducing into the host cell a nucleic acid encoding a selectable gene.

12. The method of claim 6 wherein the nucleic acid encoding the variant proinsulin is operably linked to a promoter.

13. The method of claim 12 wherein the promoter is inducible.

14. The method of claim 6 wherein the nucleic acid encoding the variant proinsulin is proins.RTKR(SEQ ID NO:22).Ip/RQKR(SEQ ID NO:23).IIp.

15. The method of claim 6 wherein the nucleic acid encoding the variant proinsulin is proins.RTKR(SEQ ID NO:22).Ip/RQKR(SEQ ID NO:23).IIp.B10H>D.

16. The method of claim 6 comprising the additional steps:
   a) further introducing into the host cell a nucleic acid encoding a desired polypeptide; and
   b) culturing the host cell under conditions wherein the desired polypeptide is expressed.

17. The method of claim 16 wherein the desired polypeptide is selected from the group consisting of: relaxin, insulin-like growth factor I and II, growth hormone; factor VIII; factor IX; tumor necrosis factor-alpha and -beta; tissue factor protein; inhibin; activin; vascular endothelial growth factor; thrombopoietin; nerve growth factor; platelet-derived growth factor; fibroblast growth factor; epidermal growth factor; transforming growth factor; insulin-like growth factor-I and -II; interferon; GM-CSF; G-CSF; interleukins; decay accelerating factor; and atrial natriuretic peptides A, B and C.

18. The method of claim 16 further comprising recovering the desired polypeptide.

19. The method of claim 16 wherein the desired polypeptide is expressed in the form of a precursor that has a cleavage site that is recognizable by a second enzyme in the host cell which is the same as or different from the first enzyme, and wherein the desired polypeptide precursor is cleaved at its cleavage site by the second enzyme, thereby producing the desired polypeptide.

20. An animal host cell dependent on insulin, wherein the host cell is not naturally capable of forming secretory granules and comprises a nucleic acid encoding a variant proinsulin, wherein the variant proinsulin contains a non-naturally occurring cleavage site recognizable by an enzyme in the host cell that cleaves the variant proinsulin at the non-naturally occurring cleavage site to produce an active insulin in the host cell.

21. The method of claim 6, wherein the host cell comprises a heterologous nucleic acid encoding the first enzyme and is cultured under conditions wherein the first enzyme is expressed.

22. The method of claim 6 wherein the first enzyme is endogenous to the host cell.

23. The host cell of claim 20, wherein the host cell comprises a heterologous nucleic acid encoding the enzyme.

24. The host cell of claim 20, wherein the enzyme is endogenous to the host cell.

* * * * *

UNITED STATES PATENT AND TRADEMARK OFFICE
CERTIFICATE OF CORRECTION

PATENT NO. : 6,348,327 B1
DATED : February 19, 2002
INVENTOR(S) : Gorman et al.

It is certified that error appears in the above-identified patent and that said Letters Patent is hereby corrected as shown below:

Title page,
Item [56], OTHER PUBLICATIONS,
Under the reference "Davidson et al." "Intraorganellar calcium ...", "*Nature* 533:93-96" should read -- *Nature* 333:93-96 --
Under the reference "Loh et al." "Purification and...", "*J. Biol. Chem.* 280(12):7194-9205" should read -- *J. Biol. Chem.* 260(12):7194-9205 --
Under the reference "Noel et al." "Investigation of...", "*Molecular Endocrinology* 6(3):404-413" should read -- *Molecular Endocrinology* 5(3):404-413 --
Under the reference "Noel et al." "Expression of porcine...", "*J. Bio Chem.* 280(4):1876-1881" should read -- *J. Biol. Chem.* 260(4):1876-1881 --
Under the reference "Barr" "Mammalian subtilisins...", "*Cell* 88:1-3" should read -- *Cell* 66:1-3 --
Under the reference "Yoshimasa et al." "Effects of amino acid...", "*J. Biol. Chem.* 286(28):17230-17237" should read -- *J. Biol. Chem.* 265(28):17230-17237 --
Under the reference "Smeekens and Steiner et al." "Identification of a...", "*J. Biol. Chem.* 265(6):2977-3000" should read -- *J. Biol. Chem.* 265(8):2977-3000 --
Under the reference "Zhu et al." "Kex2-dependent processing...", "*Molecular Microbiol.* 8(4):511-520" should read -- *Molecular Microbiol.* 6(4):511-520 --
Under the reference "Brenner et al." "Structural and enzymatic", "*Proc. Natl. Acad. Sci. USA* 86:922-926" should read -- *Proc. Natl. Acad. Sci. USA* 89:922-926 --
Under the reference "Hosaka et al." "Arg-X-Lys/Arg-Arg Motif...", "*J. Biol. Chem.* 265(19):12127-12130" should read -- *J. Biol. Chem.* 266(19):12127-12130 --
Under the reference "Matsuzawa et al." "Structure and expression..." "Matsuzawa" should read -- Hatsuzawa --
Under the reference "Mansell DJ, et al.", "Expression of the human...", "Mansell" should read -- Hansell --
Under the reference "Mudson P, John M. et al.", "Relaxin gene expression...", "Mudson" should read -- Hudson --
Under the reference "Lee CC et al.," "Generation of cDNA probes...", "*Science* 238:1288-1291" should read -- *Science* 239:1288-1291 --
Under the reference "Stults JT et al". "Structural Characterization...", "*Biomed Environ Mass Spectrum* 18:655-664" should read -- *Biomed Environ Mass Spectrum* 19:655-664 --
Under the reference "Zollinger L. et al.", "Intracellular proteolytic...", "*Biochem Cell Biol* 88:635-640" should read -- *Biochem Cell Biol* 68:635-640 --
Under the reference "Saiki, RK et al.", "Enzymatic amplification...", "*Science* 236:1350-135" should read -- *Science* 230:1350-1354 --
Under the reference "Johnson, I. S.", "Human insulin from recombinant...", "*Science*, 218:632-637" should read -- *Science*, 219:632-637 --

UNITED STATES PATENT AND TRADEMARK OFFICE
CERTIFICATE OF CORRECTION

PATENT NO. : 6,348,327 B1
DATED : February 19, 2002
INVENTOR(S) : Gorman et al.

It is certified that error appears in the above-identified patent and that said Letters Patent is hereby corrected as shown below:

OTHER PUBLICATIONS, cont'd,
Under the reference "Rinderknecht, et al.", "The Amino Acid Sequence...", "*Journal of Biological Chemistry* 263(8):2769-2776" should read -- *Journal of Biological Chemistry* 253(8):2769-2776 --
Under the reference "Rinderknecht, et al.", "Primary structure of human...", "*FEBS Letters* 88(2):283-286" should read -- *FEBS Letters* 89(2):283-286 --
Under the reference "Jansen, et al.", "Sequence of cDNA encoding...", "*Nature* 308:609-611" should read -- *Nature* 306:609-611 --
Under the reference "Jansen, et al.", "Nucleotide sequences of cDNAs...", "*FEBS Letters* 178(2):243-246" should read -- *FEBS Letters* 179(2):243-246 --
Under the reference "Felgner et al.", "Gene therapeutics", "*Nature*, 348:351-352" should read -- Nature, 349:351-352 --
Under the reference "Barsoum", "Laboratory Methods Introduction...", "*DNA and Cell Biology* 8(4):293-300" should read -- *DNA and Cell Biology* 9(4):293-300 --
Under the reference "Miller et al.", "Redesign of Retrovirus Packaging...", "*Mol. Cell. Biol.* 8(8):2895-2902" should read -- *Mol. Cell. Biol.* 6(8):2895-2902 --
Under the reference "Dhawan et al.", "Systemic delivery of human...", "*Science* 264:1509-1512" should read -- *Science* 254:1509-1512 --

Signed and Sealed this

Eighth Day of July, 2003

JAMES E. ROGAN
*Director of the United States Patent and Trademark Office*

SEQUENCE LISTING (1) GENERAL INFORMATION:

(iii) NUMBER OF SEQUENCES: 57

(2) INFORMATION FOR SEQ ID NO: 1:

(i) SEQUENCE CHARACTERISTICS:
        (A) LENGTH: 2355 base pairs
        (B) TYPE: Nucleic Acid
        (C) STRANDEDNESS: Single
        (D) TOPOLOGY: Linear (xi) SEQUENCE DESCRIPTION: SEQ ID NO: 1:

```
TCTAGATCTA GCTGGTGTGT CTCTGATCTT GCTTCTTTTC TCCCAGCCCT          50

TCCTACTTGT GTGAGAACAA GGTTTTGAGC CATGGAGCAA AGAGGTTGGA         100

CTCTGCAGTG TACTGCTTTC GCCTTCTTTT GCGTTTGGTG TGCACTAAGC         150

AGTGTAAAAG CAAAGAGGCA GTTTGTTAAT GAATGGGCGG CGGAGATCCC         200

CGGAGGGCAA GAAGCTGCCT CTGCCATCGC CGAAGAACTG GGGTATGACC         250

TTTTGGGTCA GATTGGATCA CTTGAAAATC ACTATTTATT CAAACACAAA         300

AGCCATCCTC GGAGGTCCCG AAGAAGCGCT CTTCATATCA CTAAGAGGTT         350

ATCTGATGAT GATCGTGTGA CGTGGGCTGA ACAACAGTAT GAAAAAGAGA         400

GAAGTAAACG TTCAGTTCAA AAAGACTCAG CATTGGATCT CTTCAATGAT         450

CCAATGTGGA ATCAGCAGTG GTACTTGCAA GATACCAGAA TGACTGCAGC         500

TCTGCCCAAG CTGGACCTTC ATGTAATACC TGTTTGGGAA AAGGGTATTA         550

CTGGCAAAGG AGTTGTTATT ACTGTACTGG ATGATGGCTT GGAGTGGAAT         600

CACACAGACA TTTATGCCAA TTATGATCCA GAGGCTAGCT ATGATTTTAA         650

CGATAATGAT CATGATCCAT TTCCCCGATA TGATCTCACA AATGAAAACA         700

AACATGGAAC AAGATGTGCA GGTGAAATTG CCATGCAAGC AAATAATCAC         750

AAGTGTGGGG TTGGAGTTGC ATATAATTCC AAAGTTGGAG GCATAAGAAT         800

GCTGGATGGC ATTGTAACTG ATGCCATTGA GGCTAGTTCA ATTGGATTCA         850
```

| | |
|---|---|
| ACCCTGGCCA TGTGGATATT TACAGTGCAA GCTGGGGCCC TAATGATGAT | 900 |
| GGAAAAACTG TGGAGGGGCC TGGCAGACTA GCCCAGAAGG CATTTGAATA | 950 |
| TGGTGTCAAA CAGGGGAGAC AAGGGAAAGG CTCCATCTTT GTCTGGGCTT | 1000 |
| CAGGGAATGG GGGTCGTCAG GGAGATAACT GTGACTGTGA TGGCTACACA | 1050 |
| GACAGCATTT ACACCATCTC TATCAGCAGT GCCTCCCAGC AAGGCCTGTC | 1100 |
| ACCTTGGTAT GCAGAGAAGT GTTCTTCCAC ATTGGCTACC TCCTACAGCA | 1150 |
| GTGGTGATTA CACAGACCAG CGAATAACAA GCGCTGACCT GCACAATGAC | 1200 |
| TGCACAGAGA CCCACACAGG CACCTCGGCT TCAGCACCCC TGGCTGCTGG | 1250 |
| TATCTTTGCT CTGGCCTTGG AGGCAAACCC AAATCTTACC TGGAGAGATA | 1300 |
| TGCAGCATCT GGTTGTCTGG ACCTCTGAGT ACGACCCATT GGCCAGTAAC | 1350 |
| CCAGGTTGGA AAAGAATGG GGCAGGCTTG ATGGTGAACA GCCGATTTGG | 1400 |
| ATTTGGCTTG CTAAATGCCA AGCTCTGGT GGATTTGGCT GATCCTCGGA | 1450 |
| CCTGGAGAAA TGTGCCTGAG AAGAAAGAAT GTGTTGTAAA AGACAATAAC | 1500 |
| TTTGAGCCTA GAGCCCTGAA AGCTAATGGA GAAGTAATTG TTGAAATCCC | 1550 |
| AACAAGAGCT TGTGAAGGAC AAGAAAATGC TATCAAGTCT CTGGAACATG | 1600 |
| TGCAATTTGA AGCAACAATT GAATATTCTC GTAGAGGAGA CCTTCATGTC | 1650 |
| ACACTCACTT CTGCTGTTGG AACCAGCACT GTACTGTTGG CTGAAAGGGA | 1700 |
| AAGAGATACA TCCCCCAATG GCTTTAAGAA TTGGGACTTC ATGTCTGTTC | 1750 |
| ATACATGGGG AGAGAATCCT GTAGGCACCT GGACATTGAA AATTACAGAC | 1800 |
| ATGTCTGGAA GAATGCAAAA TGAAGGAAGG ATTGTGAACT GGAAGTTGAT | 1850 |
| TTTGCATGGG ACATCTTCTC AACCAGAGCA CATGAAGCAG CCCCGTGTGT | 1900 |
| ACACATCCTA CAATACAGTC CAGAATGACA GGAGAGGAGT GGAAAAGATG | 1950 |
| GTGAATGTTG TGGAGAAGCG GCCCACACAA AAGAGCCTGA ATGGCAATCT | 2000 |
| CCTGGTACCC AAAAACTCCA GCAGCAGCAA TGTGGAGGGT AGAAGGGATG | 2050 |
| AGCAGGTACA AGGAACTCCT TCAAAGGCCA TGCTGCGACT CCTACAAAGT | 2100 |
| GCTTTTAGCA AGAATGCACT TTCAAAACAA TCACCAAAGA AGTCTCCAAG | 2150 |
| TGCAAAGCTC AGCATCCCTT ATGAAAGTTT CTATGAAGCC TTGGAAAAGC | 2200 |
| TTAACAAGCC CTCCAAGCTT GAAGGCTCTG AAGACAGTCT GTACAGTGAC | 2250 |
| TATGTTGATG TATTCTATAA CACAAAACCT TATAAGCATA GAGATGACAG | 2300 |
| GCTGCTGCAA GCTCTCATGG ACATCCTAAA TGAGGAGAAT TAAAATAAGG | 2350 |
| AGCTC | 2355 |

(2) INFORMATION FOR SEQ ID NO: 2:

(i) SEQUENCE CHARACTERISTICS:
        (A) LENGTH: 2012 base pairs
        (B) TYPE: Nucleic Acid
        (C) STRANDEDNESS: Single
        (D) TOPOLOGY: Linear (xi) SEQUENCE DESCRIPTION: SEQ ID NO: 2:

| | |
|---|---|
| TCTAGATGCA TCTTCCCTCT TCGTCCCCTG CTCCACCACC CTGCGCGCCT | 50 |
| CACAGCCCCG CTTTTCACTC CCAAAGAAGG ATGGAGGGCG GTTGTGGATC | 100 |
| CCAGTGGAAG GCGGCCGGGT TCCTCTTCTG TGTGATGGTT TTTGCGTCTG | 150 |

-continued

| | |
|---|---|
| CCGAGAGACC CGTCTTCACG AATCATTTTC TTGTGGAGTT GCATAAAGAC | 200 |
| GGAGAGGAAG AGGCTCGCCA AGTTGCAGCA GAACACGGCT TTGGAGTCCG | 250 |
| AAAGCTCCCC TTTGCAGAAG GCCTGTATCA CTTTTATCAC AATGGGCTTG | 300 |
| CAAAGGCCAA AAGAAGACGC AGCCTACACC ATAAGCGGCA GCTAGAGAGA | 350 |
| GACCCCAGGA TAAAGATGGC GCTGCAACAA GAAGGATTTG ACCGTAAAAA | 400 |
| GAGAGGGTAC AGGGACATCA ATGAGATTGA CATCAACATG AATGATCCTC | 450 |
| TCTTTACAAA GCAATGGTAC CTGTTCAACA CTGGGCAAGC CGATGGAACT | 500 |
| CCTGGGCTAG ACTTGAACGT GGCCGAAGCC TGGGAGCTGG GATACACAGG | 550 |
| AAAAGGAGTG ACCATTGGAA TTATGGATGA TGGAATTGAC TATCTCCACC | 600 |
| CAGACCTGGC CTACAACTAC AACGCTGATG CAAGTTATGA CTTCAGCAGC | 650 |
| AATGACCCCT ACCCATACCC TCGATACACA GATGACTGGT TCAACAGCCA | 700 |
| TGGAACTAGG TGTGCAGGAG AAGTTTCTGC TGCAGCCAGC AACAATATCT | 750 |
| GTGGAGTCGG CGTAGCATAC AACTCCAAGG TGGCAGGGAT CCGGATGCTG | 800 |
| GACCAGCCCT TTATGACAGA CATCATCGAA GCCTCCTCCA TCAGCCACAT | 850 |
| GCCTCAACTG ATCGACATCT ACAGTGCAAG CTGGGGCCCC ACAGACAATG | 900 |
| GGAAGACGGT TGATGGGCCC CGAGAGCTCA CACTCCAGGC CATGGCTGAT | 950 |
| GGCGTGAACA AGGGCCGTGG GGGCAAAGGC AGCATCTATG TGTGGGCCTC | 1000 |
| TGGGGACGGT GGCAGCTACG ATGACTGCAA CTGTGACGGC TATGCTTCAA | 1050 |
| GCATGTGGAC CATCTCCATC AACTCAGCCA TCAATGATGG CAGGACTGCC | 1100 |
| TTGTATGATG AGAGTTGCTC TTCCACCTTA GCATCCACCT TCAGCAATGG | 1150 |
| GAGGAAGAGG AATCCTGAGG CTGGTGTGGC TACCACAGAC TTGTATGGCA | 1200 |
| ACTGTACTCT GAGACACTCT GGGACATCTG CAGCTGCTCC GGAGGCAGCT | 1250 |
| GGCGTGTTTG CATTAGCTTT GGAGGCTAAC CTGGATCTGA CCTGGAGAGA | 1300 |
| CATGCAACAT CTGACTGTGC TCACCTCCAA GCGGAACCAG CTTCATGATG | 1350 |
| AGGTTCATCA GTGGCGACGG AATGGGGTTG GCCTGGAATT TAATCACCTC | 1400 |
| TTTGGCTACG GAGTCCTTGA TGCAGGTGCC ATGGTGAAAA TGGCTAAAGA | 1450 |
| CTGGAAAACT GTTCCGGAGA GATTCCATTG TGTGGGAGGC TCTGTGCAGA | 1500 |
| ACCCTGAAAA AATACCACCC ACCGGCAAGC TGGTACTGAC CCTCAAAACA | 1550 |
| AATGCATGTG AGGGGAAGGA AAACTTCGTC CGCTACCTGG AGCACGTCCA | 1600 |
| AGCTGTCATC ACAGTCAACG CGACCAGGAG AGGAGACCTG AACATCAACA | 1650 |
| TGACCTCCCC AATGGGCACC AAGTCCATTT TGCTGAGCCG GCGTCCCAGA | 1700 |
| GACGACGACT CCAAGGTGGG CTTTGACAAG TGGCCTTTCA TGACCACCCA | 1750 |
| CACCTGGGGG GAGGATGCCC GAGGGACCTG GACCCTGGAG CTGGGGTTTG | 1800 |
| TGGGCAGTGC ACCACAGAAG GGGTTGCTGA AGGAATGGAC CCTGATGCTT | 1850 |
| CACGGCACAC AGAGCGCCCC ATACATCGAT CAGGTGGTGA GGGATTACCA | 1900 |
| GTCTAAGCTG GCCATGTCCA AGAAGCAGGA GCTGGAGGAA GAGCTGGATG | 1950 |
| AGGCTGTGGA GAGAAGCCTG CAAAGTATCC TGAGAAAGAA CTAGGGCCAC | 2000 |
| GCTTCCGAAT TC | 2012 |

(2) INFORMATION FOR SEQ ID NO: 3:

(i) SEQUENCE CHARACTERISTICS:
    (A) LENGTH: 753 amino acids
    (B) TYPE: Amino Acid
    (D) TOPOLOGY: Linear (xi) SEQUENCE DESCRIPTION: SEQ ID NO: 3:

```
Met Glu Gln Arg Gly Trp Thr Leu Gln Cys Thr Ala Phe Ala Phe
 1               5                  10                  15

Phe Cys Val Trp Cys Ala Leu Ser Ser Val Lys Ala Lys Arg Gln
                20                  25                  30

Phe Val Asn Glu Trp Ala Ala Glu Ile Pro Gly Gly Gln Glu Ala
                35                  40                  45

Ala Ser Ala Ile Ala Glu Glu Leu Gly Tyr Asp Leu Leu Gly Gln
                50                  55                  60

Ile Gly Ser Leu Glu Asn His Tyr Leu Phe Lys His Lys Ser His
                65                  70                  75

Pro Arg Arg Ser Arg Arg Ser Ala Leu His Ile Thr Lys Arg Leu
                80                  85                  90

Ser Asp Asp Asp Arg Val Thr Trp Ala Glu Gln Gln Tyr Glu Lys
                95                 100                 105

Glu Arg Ser Lys Arg Ser Val Gln Lys Asp Ser Ala Leu Asp Leu
               110                 115                 120

Phe Asn Asp Pro Met Trp Asn Gln Gln Trp Tyr Leu Gln Asp Thr
               125                 130                 135

Arg Met Thr Ala Ala Leu Pro Lys Leu Asp Leu His Val Ile Pro
               140                 145                 150

Val Trp Glu Lys Gly Ile Thr Gly Lys Gly Val Val Ile Thr Val
               155                 160                 165

Leu Asp Asp Gly Leu Glu Trp Asn His Thr Asp Ile Tyr Ala Asn
               170                 175                 180

Tyr Asp Pro Glu Ala Ser Tyr Asp Phe Asn Asp Asn Asp His Asp
               185                 190                 195

Pro Phe Pro Arg Tyr Asp Leu Thr Asn Glu Asn Lys His Gly Thr
               200                 205                 210

Arg Cys Ala Gly Glu Ile Ala Met Gln Ala Asn Asn His Lys Cys
               215                 220                 225

Gly Val Gly Val Ala Tyr Asn Ser Lys Val Gly Gly Ile Arg Met
               230                 235                 240

Leu Asp Gly Ile Val Thr Asp Ala Ile Glu Ala Ser Ser Ile Gly
               245                 250                 255

Phe Asn Pro Gly His Val Asp Ile Tyr Ser Ala Ser Trp Gly Pro
               260                 265                 270

Asn Asp Asp Gly Lys Thr Val Glu Gly Pro Gly Arg Leu Ala Gln
               275                 280                 285

Lys Ala Phe Glu Tyr Gly Val Lys Gln Gly Arg Gln Gly Lys Gly
               290                 295                 300

Ser Ile Phe Val Trp Ala Ser Gly Asn Gly Gly Arg Gln Gly Asp
               305                 310                 315

Asn Cys Asp Cys Asp Gly Tyr Thr Asp Ser Ile Tyr Thr Ile Ser
               320                 325                 330

Ile Ser Ser Ala Ser Gln Gln Gly Leu Ser Pro Trp Tyr Ala Glu
               335                 340                 345

Lys Cys Ser Ser Thr Leu Ala Thr Ser Tyr Ser Ser Gly Asp Tyr
               350                 355                 360
```

-continued

```
Thr Asp Gln Arg Ile Thr Ser Ala Asp Leu His Asn Asp Cys Thr
                365                 370                 375
Glu Thr His Thr Gly Thr Ser Ala Ser Ala Pro Leu Ala Ala Gly
            380                 385                 390
Ile Phe Ala Leu Ala Leu Glu Ala Asn Pro Asn Leu Thr Trp Arg
        395                 400                 405
Asp Met Gln His Leu Val Val Trp Thr Ser Glu Tyr Asp Pro Leu
    410                 415                 420
Ala Ser Asn Pro Gly Trp Lys Lys Asn Gly Ala Gly Leu Met Val
425                 430                 435
Asn Ser Arg Phe Gly Phe Gly Leu Leu Asn Ala Lys Ala Leu Val
                440                 445                 450
Asp Leu Ala Asp Pro Arg Thr Trp Arg Asn Val Pro Glu Lys Lys
            455                 460                 465
Glu Cys Val Val Lys Asp Asn Asn Phe Glu Pro Arg Ala Leu Lys
        470                 475                 480
Ala Asn Gly Glu Val Ile Val Glu Ile Pro Thr Arg Ala Cys Glu
    485                 490                 495
Gly Gln Glu Asn Ala Ile Lys Ser Leu Glu His Val Gln Phe Glu
500                 505                 510
Ala Thr Ile Glu Tyr Ser Arg Arg Gly Asp Leu His Val Thr Leu
                515                 520                 525
Thr Ser Ala Val Gly Thr Ser Thr Val Leu Leu Ala Glu Arg Glu
            530                 535                 540
Arg Asp Thr Ser Pro Asn Gly Phe Lys Asn Trp Asp Phe Met Ser
        545                 550                 555
Val His Thr Trp Gly Glu Asn Pro Val Gly Thr Trp Thr Leu Lys
    560                 565                 570
Ile Thr Asp Met Ser Gly Arg Met Gln Asn Glu Gly Arg Ile Val
575                 580                 585
Asn Trp Lys Leu Ile Leu His Gly Thr Ser Ser Gln Pro Glu His
                590                 595                 600
Met Lys Gln Pro Arg Val Tyr Thr Ser Tyr Asn Thr Val Gln Asn
            605                 610                 615
Asp Arg Arg Gly Val Glu Lys Met Val Asn Val Glu Lys Arg
        620                 625                 630
Pro Thr Gln Lys Ser Leu Asn Gly Asn Leu Leu Val Pro Lys Asn
    635                 640                 645
Ser Ser Ser Ser Asn Val Glu Gly Arg Arg Asp Glu Gln Val Gln
650                 655                 660
Gly Thr Pro Ser Lys Ala Met Leu Arg Leu Leu Gln Ser Ala Phe
                665                 670                 675
Ser Lys Asn Ala Leu Ser Lys Gln Ser Pro Lys Lys Ser Pro Ser
            680                 685                 690
Ala Lys Leu Ser Ile Pro Tyr Glu Ser Phe Tyr Glu Ala Leu Glu
        695                 700                 705
Lys Leu Asn Lys Pro Ser Lys Leu Glu Gly Ser Glu Asp Ser Leu
    710                 715                 720
Tyr Ser Asp Tyr Val Asp Val Phe Tyr Asn Thr Lys Pro Tyr Lys
725                 730                 735
His Arg Asp Asp Arg Leu Leu Gln Ala Leu Met Asp Ile Leu Asn
                740                 745                 750
Glu Glu Asn
```

-continued (2) INFORMATION FOR SEQ ID NO: 4:

(i) SEQUENCE CHARACTERISTICS:
        (A) LENGTH: 637 amino acids
        (B) TYPE: Amino Acid
        (D) TOPOLOGY: Linear (xi) SEQUENCE DESCRIPTION: SEQ ID NO: 4:

```
Met Glu Gly Gly Cys Gly Ser Gln Trp Lys Ala Ala Gly Phe Leu
 1               5                  10                  15

Phe Cys Val Met Val Phe Ala Ser Ala Glu Arg Pro Val Phe Thr
                20                  25                  30

Asn His Phe Leu Val Glu Leu His Lys Asp Gly Glu Glu Glu Ala
                35                  40                  45

Arg Gln Val Ala Ala Glu His Gly Phe Gly Val Arg Lys Leu Pro
                50                  55                  60

Phe Ala Glu Gly Leu Tyr His Phe Tyr His Asn Gly Leu Ala Lys
                65                  70                  75

Ala Lys Arg Arg Arg Ser Leu His Leu His Lys Arg Gln Leu Glu Arg
                80                  85                  90

Asp Pro Arg Ile Lys Met Ala Leu Gln Gln Glu Gly Phe Asp Arg
                95                 100                 105

Lys Lys Arg Gly Tyr Arg Asp Ile Asn Glu Ile Asp Ile Asn Met
               110                 115                 120

Asn Asp Pro Leu Phe Thr Lys Gln Trp Tyr Leu Phe Asn Thr Gly
               125                 130                 135

Gln Ala Asp Gly Thr Pro Gly Leu Asp Leu Asn Val Ala Glu Ala
               140                 145                 150

Trp Glu Leu Gly Tyr Thr Gly Lys Gly Val Thr Ile Gly Ile Met
               155                 160                 165

Asp Asp Gly Ile Asp Tyr Leu His Pro Asp Leu Ala Tyr Asn Tyr
               170                 175                 180

Asn Ala Asp Ala Ser Tyr Asp Phe Ser Ser Asn Asp Pro Tyr Pro
               185                 190                 195

Tyr Pro Arg Tyr Thr Asp Asp Trp Phe Asn Ser His Gly Thr Arg
               200                 205                 210

Cys Ala Gly Glu Val Ser Ala Ala Ala Ser Asn Asn Ile Cys Gly
               215                 220                 225

Val Gly Val Ala Tyr Asn Ser Lys Val Ala Gly Ile Arg Met Leu
               230                 235                 240

Asp Gln Pro Phe Met Thr Asp Ile Ile Glu Ala Ser Ser Ile Ser
               245                 250                 255

His Met Pro Gln Leu Ile Asp Ile Tyr Ser Ala Ser Trp Gly Pro
               260                 265                 270

Thr Asp Asn Gly Lys Thr Val Asp Gly Pro Arg Glu Leu Thr Leu
               275                 280                 285

Gln Ala Met Ala Asp Gly Val Asn Lys Gly Arg Gly Lys Gly
               290                 295                 300

Ser Ile Tyr Val Trp Ala Ser Gly Asp Gly Gly Ser Tyr Asp Asp
               305                 310                 315

Cys Asn Cys Asp Gly Tyr Ala Ser Ser Met Trp Thr Ile Ser Ile
               320                 325                 330

Asn Ser Ala Ile Asn Asp Gly Arg Thr Ala Leu Tyr Asp Glu Ser
               335                 340                 345
```

Cys Ser Ser Thr Leu Ala Ser Thr Phe Ser Asn Gly Arg Lys Arg
              350                 355                 360

Asn Pro Glu Ala Gly Val Ala Thr Thr Asp Leu Tyr Gly Asn Cys
              365                 370                 375

Thr Leu Arg His Ser Gly Thr Ser Ala Ala Pro Glu Ala Ala
              380                 385                 390

Gly Val Phe Ala Leu Ala Leu Glu Ala Asn Leu Asp Leu Thr Trp
              395                 400                 405

Arg Asp Met Gln His Leu Thr Val Leu Thr Ser Lys Arg Asn Gln
              410                 415                 420

Leu His Asp Glu Val His Gln Trp Arg Arg Asn Gly Val Gly Leu
              425                 430                 435

Glu Phe Asn His Leu Phe Gly Tyr Gly Val Leu Asp Ala Gly Ala
              440                 445                 450

Met Val Lys Met Ala Lys Asp Trp Lys Thr Val Pro Glu Arg Phe
              455                 460                 465

His Cys Val Gly Gly Ser Val Gln Asn Pro Glu Lys Ile Pro Pro
              470                 475                 480

Thr Gly Lys Leu Val Leu Thr Leu Lys Thr Asn Ala Cys Glu Gly
              485                 490                 495

Lys Glu Asn Phe Val Arg Tyr Leu Glu His Val Gln Ala Val Ile
              500                 505                 510

Thr Val Asn Ala Thr Arg Arg Gly Asp Leu Asn Ile Asn Met Thr
              515                 520                 525

Ser Pro Met Gly Thr Lys Ser Ile Leu Leu Ser Arg Arg Pro Arg
              530                 535                 540

Asp Asp Asp Ser Lys Val Gly Phe Asp Lys Trp Pro Phe Met Thr
              545                 550                 555

Thr His Thr Trp Gly Glu Asp Ala Arg Gly Thr Trp Thr Leu Glu
              560                 565                 570

Leu Gly Phe Val Gly Ser Ala Pro Gln Lys Gly Leu Leu Lys Glu
              575                 580                 585

Trp Thr Leu Met Leu His Gly Thr Gln Ser Ala Pro Tyr Ile Asp
              590                 595                 600

Gln Val Val Arg Asp Tyr Gln Ser Lys Leu Ala Met Ser Lys Lys
              605                 610                 615

Gln Glu Leu Glu Glu Leu Asp Glu Ala Val Glu Arg Ser Leu
              620                 625                 630

Gln Ser Ile Leu Arg Lys Asn
              635

(2) INFORMATION FOR SEQ ID NO: 5:

(i) SEQUENCE CHARACTERISTICS:
        (A) LENGTH: 32 base pairs
        (B) TYPE: Nucleic Acid
        (C) STRANDEDNESS: Single
        (D) TOPOLOGY: Linear (xi) SEQUENCE DESCRIPTION: SEQ ID NO: 5:

GCAAAATCTA GAYKGCNATY GTNGAYGAKG GN                                              32

(2) INFORMATION FOR SEQ ID NO: 6:

(i) SEQUENCE CHARACTERISTICS:
        (A) LENGTH: 30 base pairs (B) TYPE: Nucleic Acid
        (C) STRANDEDNESS: Single
        (D) TOPOLOGY: Linear (xi) SEQUENCE DESCRIPTION: SEQ ID NO: 6:

AAGCATGAGC TCNGGRGCRG CRGCNGANCC                                              30

(2) INFORMATION FOR SEQ ID NO: 7:

(i) SEQUENCE CHARACTERISTICS:
        (A) LENGTH: 30 base pairs
        (B) TYPE: Nucleic Acid
        (C) STRANDEDNESS: Single
        (D) TOPOLOGY: Linear (xi) SEQUENCE DESCRIPTION: SEQ ID NO: 7:

GATATCACTC AGATCGATGA ATTCGAGCTC                                              30

(2) INFORMATION FOR SEQ ID NO: 8:

(i) SEQUENCE CHARACTERISTICS:
        (A) LENGTH: 33 base pairs
        (B) TYPE: Nucleic Acid
        (C) STRANDEDNESS: Single
        (D) TOPOLOGY: Linear (xi) SEQUENCE DESCRIPTION: SEQ ID NO: 8:

AAGCTTTCTA GAGGATCCCT CTGGTGGATT TGG                                          33

(2) INFORMATION FOR SEQ ID NO: 9:

(i) SEQUENCE CHARACTERISTICS:
        (A) LENGTH: 30 base pairs
        (B) TYPE: Nucleic Acid
        (C) STRANDEDNESS: Single
        (D) TOPOLOGY: Linear (xi) SEQUENCE DESCRIPTION: SEQ ID NO: 9:

AAGCTTGAAT TCTCCAACCC CACACTTGTG                                              30

(2) INFORMATION FOR SEQ ID NO: 10:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO: 10:

AGATCGATGA ATTCGAGCTC                                                         20

(2) INFORMATION FOR SEQ ID NO: 11:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (xi) SEQUENCE DESCRIPTION: SEQ ID NO: 11:

CATTCTCGAA AAAAGAGACA A                                                       21

(2) INFORMATION FOR SEQ ID NO: 12:

(i) SEQUENCE CHARACTERISTICS:
        (A) LENGTH: 21 base pairs
        (B) TYPE: Nucleic Acid

```
        (C) STRANDEDNESS: Single
        (D) TOPOLOGY: Linear (xi) SEQUENCE DESCRIPTION: SEQ ID NO: 12:

CATTCTGTAA AAAAGAGACA A                                              21

(2) INFORMATION FOR SEQ ID NO: 13:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (xi) SEQUENCE DESCRIPTION: SEQ ID NO: 13:

CATTCTAGAG CAAAGAGACA A                                              21

(2) INFORMATION FOR SEQ ID NO: 14:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (xi) SEQUENCE DESCRIPTION: SEQ ID NO: 14:

CATTCTAGAA AAGCAAGACA A                                              21

(2) INFORMATION FOR SEQ ID NO: 15:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (xi) SEQUENCE DESCRIPTION: SEQ ID NO: 15:

CATTCTAGAA AAAGAGCACA A                                              21

(2) INFORMATION FOR SEQ ID NO: 16:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (xi) SEQUENCE DESCRIPTION: SEQ ID NO: 16:

ACCTGGAGCA AAGCTTCTCT G                                              21

(2) INFORMATION FOR SEQ ID NO: 17:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (xi) SEQUENCE DESCRIPTION: SEQ ID NO: 17:

ACCTGGAGCG CTAGGTCTCT G                                              21

(2) INFORMATION FOR SEQ ID NO: 18:

(i) SEQUENCE CHARACTERISTICS:
        (A) LENGTH: 30 base pairs
        (B) TYPE: Nucleic Acid
        (C) STRANDEDNESS: Single
```

(D) TOPOLOGY: Linear (xi) SEQUENCE DESCRIPTION: SEQ ID NO: 18:

CATAAGCTTA CCATGGCCCT GTGGATGCGC                                        30

(2) INFORMATION FOR SEQ ID NO: 19:

(i) SEQUENCE CHARACTERISTICS:
        (A) LENGTH: 30 base pairs
        (B) TYPE: Nucleic Acid
        (C) STRANDEDNESS: Single
        (D) TOPOLOGY: Linear (xi) SEQUENCE DESCRIPTION: SEQ ID NO: 19:

CATTCTAGAC TAGTTGCAGT AGTTCTCCAG                                         30

(2) INFORMATION FOR SEQ ID NO: 20:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO: 20:

Lys Thr Arg Arg
 1

(2) INFORMATION FOR SEQ ID NO: 21:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO: 21:

Leu Gln Lys Arg
 1

(2) INFORMATION FOR SEQ ID NO: 22:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO: 22:

Arg Thr Lys Arg
 1

(2) INFORMATION FOR SEQ ID NO: 23:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO: 23:

Arg Gln Lys Arg
 1

(2) INFORMATION FOR SEQ ID NO: 24:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO: 24:

Lys Thr Lys Arg
 1

(2) INFORMATION FOR SEQ ID NO: 25:

(i) SEQUENCE CHARACTERISTICS:
        (A) LENGTH: 31 base pairs
        (B) TYPE: Nucleic Acid
        (C) STRANDEDNESS: Single
        (D) TOPOLOGY: Linear (xi) SEQUENCE DESCRIPTION: SEQ ID NO: 25:

CTCTGCCTCC CGCTTGGTCC TGGGTGTGTA G                                    31

(2) INFORMATION FOR SEQ ID NO: 26:

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (xi) SEQUENCE DESCRIPTION: SEQ ID NO: 26:

CACGCTTCTG CCGGGATCCC TC                                              22

(2) INFORMATION FOR SEQ ID NO: 27:

(i) SEQUENCE CHARACTERISTICS:
        (A) LENGTH: 31 base pairs
        (B) TYPE: Nucleic Acid
        (C) STRANDEDNESS: Single
        (D) TOPOLOGY: Linear (xi) SEQUENCE DESCRIPTION: SEQ ID NO: 27:

CTCTGCCTCC CGCTTGGTCT TCGGTGTGTA G                                    31

(2) INFORMATION FOR SEQ ID NO: 28:

(i) SEQUENCE CHARACTERISTICS:
        (A) LENGTH: 36 base pairs
        (B) TYPE: Nucleic Acid
        (C) STRANDEDNESS: Single
        (D) TOPOLOGY: Linear (xi) SEQUENCE DESCRIPTION: SEQ ID NO: 28:

GATATGAAGA GCAGATCTTT TGGACCTCCG AGGATG                               36

(2) INFORMATION FOR SEQ ID NO: 29:

(i) SEQUENCE CHARACTERISTICS:
        (A) LENGTH: 39 base pairs
        (B) TYPE: Nucleic Acid
        (C) STRANDEDNESS: Single
        (D) TOPOLOGY: Linear (xi) SEQUENCE DESCRIPTION: SEQ ID NO: 29:

CTTATGGTGT AAGCTTCGTT TTGCTCTGGC CTTTGCAAG                            39

(2) INFORMATION FOR SEQ ID NO: 30:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (xi) SEQUENCE DESCRIPTION: SEQ ID NO: 30:

TACAACTCAC CGCGGGTCCT G                                    21

(2) INFORMATION FOR SEQ ID NO: 31:

(i) SEQUENCE CHARACTERISTICS:
        (A) LENGTH: 38 base pairs
        (B) TYPE: Nucleic Acid
        (C) STRANDEDNESS: Single
        (D) TOPOLOGY: Linear (xi) SEQUENCE DESCRIPTION: SEQ ID NO: 31:

AAGATGGGAT GGGATGATGA CCGTTTCCGC CTTGATGT                   38

(2) INFORMATION FOR SEQ ID NO: 32:

(i) SEQUENCE CHARACTERISTICS:
        (A) LENGTH: 38 base pairs
        (B) TYPE: Nucleic Acid
        (C) STRANDEDNESS: Single
        (D) TOPOLOGY: Linear (xi) SEQUENCE DESCRIPTION: SEQ ID NO: 32:

ACATCACGGC GGAAACGGTC ATCATCCCAT CCCATCTT                   38

(2) INFORMATION FOR SEQ ID NO: 33:

(i) SEQUENCE CHARACTERISTICS:
        (A) LENGTH: 28 base pairs
        (B) TYPE: Nucleic Acid
        (C) STRANDEDNESS: Single
        (D) TOPOLOGY: Linear (xi) SEQUENCE DESCRIPTION: SEQ ID NO: 33:

GATATAAGCT TGAGAGTGTA GAAGGGGC                              28

(2) INFORMATION FOR SEQ ID NO: 34:

(i) SEQUENCE CHARACTERISTICS:
        (A) LENGTH: 40 base pairs
        (B) TYPE: Nucleic Acid
        (C) STRANDEDNESS: Single
        (D) TOPOLOGY: Linear (xi) SEQUENCE DESCRIPTION: SEQ ID NO: 34:

GGCTTGACAT CATTGGCTGA CACTTTCGAA CACATGATAG                 40

(2) INFORMATION FOR SEQ ID NO: 35:

(i) SEQUENCE CHARACTERISTICS:
        (A) LENGTH: 41 base pairs
        (B) TYPE: Nucleic Acid
        (C) STRANDEDNESS: Single
        (D) TOPOLOGY: Linear (xi) SEQUENCE DESCRIPTION: SEQ ID NO: 35:

AAGATGGGAT GGGATGATGA GCGCCGGACC CTCATGGACA T               41

(2) INFORMATION FOR SEQ ID NO: 36:

(i) SEQUENCE CHARACTERISTICS:
        (A) LENGTH: 41 base pairs
        (B) TYPE: Nucleic Acid
        (C) STRANDEDNESS: Single
        (D) TOPOLOGY: Linear (xi) SEQUENCE DESCRIPTION: SEQ ID NO: 36:

```
ATGTCCATGA GGGTCCGGCG CTCATCATCC CATCCCATCT T                41
```

(2) INFORMATION FOR SEQ ID NO: 37:

(i) SEQUENCE CHARACTERISTICS:
        (A) LENGTH: 28 base pairs
        (B) TYPE: Nucleic Acid
        (C) STRANDEDNESS: Single
        (D) TOPOLOGY: Linear (xi) SEQUENCE DESCRIPTION: SEQ ID NO: 37:

```
GATATAAGCT TGAGAGTGTA GAAGGGGC                               28
```

(2) INFORMATION FOR SEQ ID NO: 38:

(i) SEQUENCE CHARACTERISTICS:
        (A) LENGTH: 51 base pairs
        (B) TYPE: Nucleic Acid
        (C) STRANDEDNESS: Single
        (D) TOPOLOGY: Linear (xi) SEQUENCE DESCRIPTION: SEQ ID NO: 38:

```
TGAGCGACAG CACCCCCTTG GAGCCCCGC CCTTGTATCT CATGGAGGAT         50
T                                                            51
```

(2) INFORMATION FOR SEQ ID NO: 39:

(i) SEQUENCE CHARACTERISTICS:
        (A) LENGTH: 51 base pairs
        (B) TYPE: Nucleic Acid
        (C) STRANDEDNESS: Single
        (D) TOPOLOGY: Linear (xi) SEQUENCE DESCRIPTION: SEQ ID NO: 39:

```
TCAGCTCCCC TCGTCGGGCG GGGTCCGAGT GCCGTTTCCG CCGTGATGTT        50
C                                                            51
```

(2) INFORMATION FOR SEQ ID NO: 40:

(i) SEQUENCE CHARACTERISTICS:
        (A) LENGTH: 48 base pairs
        (B) TYPE: Nucleic Acid
        (C) STRANDEDNESS: Single
        (D) TOPOLOGY: Linear (xi) SEQUENCE DESCRIPTION: SEQ ID NO: 40:

```
ACGTGGGCAG CCCCGTGGTG GCGAACAGAA CATCACGGCG GAAACGGC          48
```

(2) INFORMATION FOR SEQ ID NO: 41:

(i) SEQUENCE CHARACTERISTICS:
        (A) LENGTH: 48 base pairs
        (B) TYPE: Nucleic Acid
        (C) STRANDEDNESS: Single
        (D) TOPOLOGY: Linear (xi) SEQUENCE DESCRIPTION: SEQ ID NO: 41:

```
TGTTCGCCAC CACGGGGCTG CCCACGTAAT CCTCCATGAG ATACAAGG          48
```

(2) INFORMATION FOR SEQ ID NO: 42:

(i) SEQUENCE CHARACTERISTICS:
        (A) LENGTH: 26 base pairs
        (B) TYPE: Nucleic Acid
        (C) STRANDEDNESS: Single (D) TOPOLOGY: Linear (xi) SEQUENCE DESCRIPTION: SEQ ID NO: 42:

CTCGGACCCC GCCCGACGAG GGGAGC                                        26

(2) INFORMATION FOR SEQ ID NO: 43:

(i) SEQUENCE CHARACTERISTICS:
        (A) LENGTH: 27 base pairs
        (B) TYPE: Nucleic Acid
        (C) STRANDEDNESS: Single
        (D) TOPOLOGY: Linear (xi) SEQUENCE DESCRIPTION: SEQ ID NO: 43:

GCGGGGGCTC CAAGGGGTG CTGTCGC                                        27

(2) INFORMATION FOR SEQ ID NO: 44:

(i) SEQUENCE CHARACTERISTICS:
        (A) LENGTH: 54 base pairs
        (B) TYPE: Nucleic Acid
        (C) STRANDEDNESS: Single
        (D) TOPOLOGY: Linear (xi) SEQUENCE DESCRIPTION: SEQ ID NO: 44:

GTAGAACAAC ATGGACATGG TGGCAATATT GTCGACTCTG GAGTCGACCT              50

GCAG                                                                54

(2) INFORMATION FOR SEQ ID NO: 45:

(i) SEQUENCE CHARACTERISTICS:
        (A) LENGTH: 48 base pairs
        (B) TYPE: Nucleic Acid
        (C) STRANDEDNESS: Single
        (D) TOPOLOGY: Linear (xi) SEQUENCE DESCRIPTION: SEQ ID NO: 45:

CACATAAAAC AAGATGGACA TGGTCTTGTT CACCTGTAGG ATCCCCGG                48

(2) INFORMATION FOR SEQ ID NO: 46:

(i) SEQUENCE CHARACTERISTICS:
        (A) LENGTH: 53 base pairs
        (B) TYPE: Nucleic Acid
        (C) STRANDEDNESS: Single
        (D) TOPOLOGY: Linear (xi) SEQUENCE DESCRIPTION: SEQ ID NO: 46:

AGTAAGGAAA AGGATGGTCA TGGTGGAGGT CGACAAGCTT GAGAATTCAA              50

TCG                                                                 53

(2) INFORMATION FOR SEQ ID NO: 47:

(i) SEQUENCE CHARACTERISTICS:
        (A) LENGTH: 4 amino acids
        (B) TYPE: Amino Acid
        (D) TOPOLOGY: Linear (xi) SEQUENCE DESCRIPTION: SEQ ID NO: 47:

Xaa Xaa Xaa Arg
 1

(2) INFORMATION FOR SEQ ID NO: 48:

(i) SEQUENCE CHARACTERISTICS:

(A) LENGTH: 7 amino acids
                (B) TYPE: Amino Acid
                (D) TOPOLOGY: Linear (xi) SEQUENCE DESCRIPTION: SEQ ID NO: 48:

His Ser Arg Lys Lys Arg Gln
 1               5

(2) INFORMATION FOR SEQ ID NO: 49:

(i) SEQUENCE CHARACTERISTICS:
                (A) LENGTH: 7 amino acids
                (B) TYPE: Amino Acid
                (D) TOPOLOGY: Linear (xi) SEQUENCE DESCRIPTION: SEQ ID NO: 49:

His Ser Val Lys Lys Arg Gln
 1               5

(2) INFORMATION FOR SEQ ID NO: 50:

(i) SEQUENCE CHARACTERISTICS:
                (A) LENGTH: 7 amino acids
                (B) TYPE: Amino Acid
                (D) TOPOLOGY: Linear (xi) SEQUENCE DESCRIPTION: SEQ ID NO: 50:

His Ser Arg Ala Lys Arg Gln
 1               5

(2) INFORMATION FOR SEQ ID NO: 51:

(i) SEQUENCE CHARACTERISTICS:
                (A) LENGTH: 7 amino acids
                (B) TYPE: Amino Acid
                (D) TOPOLOGY: Linear (xi) SEQUENCE DESCRIPTION: SEQ ID NO: 51:

His Ser Arg Lys Ala Arg Gln
 1               5

(2) INFORMATION FOR SEQ ID NO: 52:

(i) SEQUENCE CHARACTERISTICS:
                (A) LENGTH: 7 amino acids
                (B) TYPE: Amino Acid
                (D) TOPOLOGY: Linear (xi) SEQUENCE DESCRIPTION: SEQ ID NO: 52:

His Ser Arg Lys Arg Ala Gln
 1               5

(2) INFORMATION FOR SEQ ID NO: 53:

(i) SEQUENCE CHARACTERISTICS:
                (A) LENGTH: 7 amino acids
                (B) TYPE: Amino Acid
                (D) TOPOLOGY: Linear (xi) SEQUENCE DESCRIPTION: SEQ ID NO: 53:

Thr Trp Ser Lys Ala Ser Gln
 1               5

(2) INFORMATION FOR SEQ ID NO: 54:

(i) SEQUENCE CHARACTERISTICS:
                (A) LENGTH: 7 amino acids

```
            (B) TYPE: Amino Acid
            (D) TOPOLOGY: Linear (xi) SEQUENCE DESCRIPTION: SEQ ID NO: 54:

Thr Trp Ser Ala Arg Ser Gln
  1               5

(2) INFORMATION FOR SEQ ID NO: 55:

(i) SEQUENCE CHARACTERISTICS:
            (A) LENGTH: 30 base pairs
            (B) TYPE: Nucleic Acid
            (C) STRANDEDNESS: Single
            (D) TOPOLOGY: Linear (xi) SEQUENCE DESCRIPTION: SEQ ID NO: 55:

CATAAGCTTA CCATGGCCCT GTGGATGCGC                                      30

(2) INFORMATION FOR SEQ ID NO: 56:

(i) SEQUENCE CHARACTERISTICS:
            (A) LENGTH: 30 base pairs
            (B) TYPE: Nucleic Acid
            (C) STRANDEDNESS: Single
            (D) TOPOLOGY: Linear (xi) SEQUENCE DESCRIPTION: SEQ ID NO: 56:

CATTCTAGAC TAGTTGCAGT AGTTCTCCAG                                      30

(2) INFORMATION FOR SEQ ID NO: 57:

(i) SEQUENCE CHARACTERISTICS:
            (A) LENGTH: 29 base pairs
            (B) TYPE: Nucleic Acid
            (C) STRANDEDNESS: Single
            (D) TOPOLOGY: Linear (xi) SEQUENCE DESCRIPTION: SEQ ID NO: 57:

GCTTCCACCA GGTCGGATCC GCACAGGTG                                       29
```